United States Patent [19]
Sohda et al.

[11] Patent Number: 6,046,189
[45] Date of Patent: Apr. 4, 2000

[54] THIENOPYRIDINE DERIVATIVES AND THEIR USE

[75] Inventors: Takashi Sohda, Takatsuki; Haruhiko Makino, Hyogo; Atsuo Baba, Ashiya, all of Japan

[73] Assignee: Takeda Chemical Industries, Ltd., Osaka, Japan

[21] Appl. No.: 08/860,452

[22] PCT Filed: Apr. 23, 1997

[86] PCT No.: PCT/JP97/01413

§ 371 Date: Jun. 26, 1997

§ 102(e) Date: Jun. 26, 1997

[87] PCT Pub. No.: WO97/40050

PCT Pub. Date: Oct. 30, 1997

[30] Foreign Application Priority Data

Apr. 25, 1996 [JP] Japan ..................... 8-105916
Apr. 25, 1996 [JP] Japan ..................... 8-105917

[51] Int. Cl.$^7$ .................. C07D 493/14; C07D 223/00; A61K 31/435; A61K 31/55
[52] U.S. Cl. .................. 514/212; 514/291; 540/484; 546/83
[58] Field of Search ............. 546/83; 514/291, 514/212; 540/484

[56] References Cited

FOREIGN PATENT DOCUMENTS

| | | |
|---|---|---|
| 49-18887 | 2/1974 | Japan . |
| 50-11398 | 4/1975 | Japan . |
| 51-43796 | 4/1976 | Japan . |
| 52-46095 | 4/1977 | Japan . |
| WO 96 14319 | 5/1996 | WIPO . |

OTHER PUBLICATIONS

Journal of Medicinal Chemistry, 1973, vol. 16, No. 3, pp. 214–219.
Journal of Medicinal Chemistry, 1974, vol. 17, No. 6, pp. 624–630.
Khim. Geterotsikl. Soedin., 1987, No. 1, pp. 124–128.
Bulletin of the Chemical Society of Japan, 1988, vol. 61, No. 12, pp. 4431–4433.
Chemical and Pharmaceutical Bulletin, 1992, vol. 40, No. 6, pp. 1376–1382.
Phosphorus, Sulfur, and Silicon and the Related Elements, 1992, vol. 73, pp. 127–135.
Chemical & Pharmaceutical Bulletin, 1988, vol. 36, No. 11, pp. 4389–4402.
Journal für praktische Chemie, Band 317, 1975, Heft 5, pp. 705–880.

*Primary Examiner*—Alan L. Rotman
*Attorney, Agent, or Firm*—Foley & Lardner

[57] ABSTRACT

There is disclosed a compound of the formula (A):

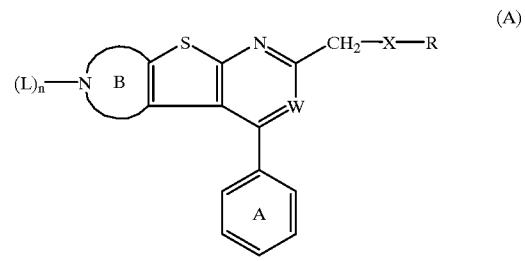

wherein W is C-G or C-G' (G is optionally esterified carboxyl; and G' is halogen); X is oxygen, optionally oxidized sulfur or —$(CH_2)_q$— (q is 0 to 5); R is optionally substituted amino or heterocyclic group; the ring B is optionally substituted nitrogen-containing 5- to 7-membered ring; L is hydrogen, optionally substituted hydrocarbon residue, optionally substituted acyl, optionally substituted carbamoyl, optionally substituted thiocarbamoyl or optionally substituted sulfonyl provided that, when W is C-G, L is hydrogen, optionally substituted acyl, optionally substituted carbamoyl, optionally substituted alkoxycarbonyl, optionally substituted thiocarbamoyl or optionally substituted sulfonyl; n is 0 or 1; the ring A may have a substituent. A process for producing the compound (A) and a pharmaceutical composition containing the compound (A) are also disclosed. The pharmaceutical composition is useful for an anti-inflammatory drug, particularly, a drug for preventing or treating arthritis, a drug for inhibiting bone resorption, immunosuppressant or the like.

17 Claims, No Drawings

THIENOPYRIDINE DERIVATIVES AND THEIR USE

FIELD OF THE INVENTION

The present invention relates to a new thienopyridine derivative useful as an anti-inflammatory drug, especially as a drug for treating arthritis, or a salt thereof. The thienopyridine derivative or a salt thereof also has bone resorption inhibitory activity and is useful as a drug for preventing and treating osteoporosis. In addition, the thienopyridine derivative or a salt thereof is useful, for example, as a drug for preventing and treating immune-related diseases, such as an immunosuppressant.

BACKGROUND OF THE INVENTION

Arthritis, an inflammatory disease of the joint, occurs in various forms such as rheumatoid arthritis and related diseases with joint inflammation.

Rheumatoid arthritis, also called chronic rheumatism, in particular, is a chronic multiple arthritis characterized by inflammatory changes in the synovial membrane of the articular capsule inner layer. Arthritic diseases like rheumatoid arthritis are progressive and cause joint disorders such as deformation and acampsia, often resulting in severe physical disorder due to a lack of effective treatment and subsequent deterioration.

Traditionally, these forms of arthritis have been chemotherapeutically treated with various drugs including steroids and other adrenocortical hormones (e.g., cortisone), non-steroidal anti-inflammatory drugs (e.g., aspirin, piroxicam, indomethacin), gold-containing drugs (e.g., aurothiomalate), antirheumatic drugs (e.g., chloroquine preparations, D-penicillamine), anti-gout drugs (e.g., colchicine) and immunosuppressors (e.g., cyclophosphamide, azathioprine, methotrexate, levamisole).

However, these drugs have drawbacks such as severe adverse reactions, adverse reactions hampering the drug's long-term use, a lack of efficacy and a failure to be effective against already-occurring arthritis.

Accordingly, there is a need for the development of a drug which exhibits excellent prophylactic/therapeutic action on arthritis with low toxicity in clinical situations.

Heretofore, various compounds have been synthesized as thieno[2,3-b]pyridine derivatives including those described in the Bulletin of the Chemical Society of Japan, Vol. 61, p. 4431 (1988), Chemical and Pharmaceutical Bulletin, Vol. 36, p. 4389 (1988), Phosphorus, Sulfur and Silicon, Vol. 73, p. 127 (1992), Chemical and Pharmaceutical Bulletin, Vol. 40, p. 1376 (1992) and Khim Geterotsikl Soedin, Vol. 1, p. 124 (1987). However, these compounds are limited to the structure in which the substituent at the 6-position in the thieno[2,3-b]pyridine skeleton is a methyl group. Also, no description of anti-inflammatory action, bone resorption inhibitory action or immunosuppressant action is given for these known thienopyridine derivatives.

OBJECTS OF THE INVENTION

One object of the present invention is to provide novel thienopyridine derivatives which have anti-inflammatory activity and useful, for example, as anti-inflammatory drugs, especially as drugs for treating arthritis, as well as which have bone resorption inhibitory activity and immunosuppressant activity and useful as drugs for inhibiting bone resorption and immunosuppressants, or salts thereof.

Another object of the present invention is to provide a pharmaceutical composition useful for treating inflammation, in particular, arthritis, for preventing or treating arthritis, for inhibiting bone resorption and immunosuppressant which comprising the novel thienopyridine derivative or a salt thereof as an effective component.

These objects as well as other objects and advantages of the present invention will become apparent to those skilled in the art from the following description.

SUMMARY OF THE INVENTION

The present inventors found that a novel thienopyridine derivative represented by the following formula (A) has antiarthritic activity and serves well as a joint destruction suppressor and also found that the thienopyridine derivative has bone resorption inhibitory activity which functions on a bone directly and serves well as a bone resorption inhibitory drug. In addition, the present inventors found that the thienopyridine derivative represented by the formula (A) is useful, for example, as a drug for preventing or treating immune-related diseases. The present inventors further made investigations based on these findings and completed the present invention.

That is, according to the present invention, there is provided a compound represented by the formula (A):

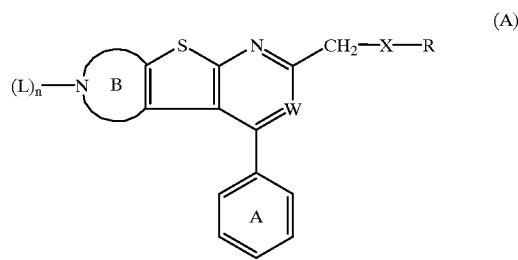

wherein W represents C-G or C-G' (G represents a carboxyl group which may be esterified; and G' represents a halogen atom); X represents an oxygen atom, a sulfur atom which may be oxidized or —(CH$_2$)$_q$— (q represents an integer from 0 to 5); R represents an optionally substituted amino group or an optionally substituted heterocyclic group; the ring B represents an optionally substituted nitrogen-containing 5- to 7-membered ring; L represents a hydrogen atom, an optionally substituted hydrocarbon residue, an optionally substituted acyl group, an optionally substituted carbamoyl group, an optionally substituted thiocarbamoyl group or an optionally substituted sulfonyl group, provided that, when W is C-G, L is a hydrogen atom, an optionally substituted acyl group, an optionally substituted carbamoyl group, an optionally substituted alkoxycarbonyl group, an optionally substituted thiocarbamoyl group or an optionally substituted sulfonyl group; n represents 0 or 1; and the ring A may have a substituent; or a salt thereof.

The present invention also provides a process for producing a compound of the formula (A) or a salt thereof and a pharmaceutical composition comprising as an effective component a compound of the formula (A) or a pharmaceutically acceptable salt thereof, in particular, a pharmaceutical composition for preventing or treating inflammation, a pharmaceutical composition for preventing or treating arthritis, a pharmaceutical composition for preventing or treating rheumatism, a pharmaceutical composition for preventing or treating chronic rheumatoid arthritis, a pharmaceutical composition having bone resorption inhibitory activity, a pharmaceutical composition for preventing or treating osteoporosis, a pharmaceutical composition having cytokine-production inhibitory activity, a pharmaceutical composition for preventing or treating autoimmune diseases, and a pharmaceutical composition for preventing rejection after organ transplantation.

DETAILED DESCRIPTION OF THE INVENTION

The compound of the formula (A) includes a compound represented by the formula (I) or (I'):

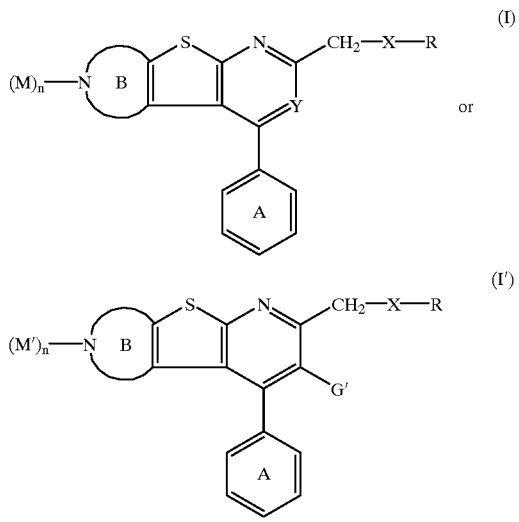

wherein Y represents C-G; M represents a hydrogen atom, an optionally substituted acyl group, an optionally substituted carbamoyl group, an optionally substituted alkoxycarbonyl group, an optionally substituted thiocarbamoyl group or an optionally substituted sulfonyl group; M' represents a hydrogen atom, an optionally substituted hydrocarbon residue, an optionally substituted acyl group, an optionally substituted carbamoyl group, an optionally substituted thiocarbamoyl group or an optionally substituted sulfonyl group; and the other symbols are as defined above.

That is, according to one aspect of the present invention, there is provided a compound represented by the formula (I), or a salt thereof.

In the compound of the formula (I), preferably, the optionally substituted amino group represented by R is —N($R^1$)($R^2$) (wherein $R^1$ and $R^2$ are the same or different and represent a hydrogen atom, an optionally substituted hydrocarbon residue, an optionally substituted acyl group, an optionally substituted sulfonyl group or an optionally substituted heterocyclic group, or $R^1$ and $R^2$ may bind to each other to form a nitrogen-containing 5 to 7 membered ring); and the optionally substituted heterocyclic group represented by R is an aromatic monocyclic heterocyclic group, an aromatic condensed heterocyclic group or a non-aromatic heterocyclic group.

More preferably, the optionally substituted hydrocarbon residue represented by $R^1$ or $R^2$ is an optionally substituted $C_{1-6}$ alkyl group and the optionally substituted heterocyclic group represented by $R^1$ or $R^2$ is an aromatic 5-membered heterocyclic group containing 2 to 3 hetero atoms; and the optionally substituted heterocyclic group represented by R is (i) a 5- to 7-membered heterocyclic group containing one sulfur atom, nitrogen atom or oxygen atom, (ii) a 5- or 6-membered heterocyclic group containing 2 to 4 nitrogen atoms, (iii) a 5- or 6-membered heterocyclic group containing 1 or 2 nitrogen atoms and one sulfur atom or oxygen atom, or (iv) one of the above 3 heterocyclic groups as condensed with a 6-membered ring containing 2 or fewer nitrogen atoms, a benzene ring or a 5-membered ring containing one sulfur atom.

Preferably, the optionally substituted 5- to 7-membered ring B is an optionally substituted 6-membered heterocyclic ring containing one nitrogen atom.

Preferably, the ring A may be substituted by a halogen atom, a nitro group, an optionally substituted alkyl group, an optionally substituted hydroxy group, an optionally substituted thiol group, an optionally substituted amino group, an optionally substituted acyl group, an optionally esterified carboxyl group or an optionally substituted aromatic ring group. More preferably, the substituent for the ring A is an $C_{1-6}$ alkoxy group or a hydroxy group.

Preferably, X is —($CH_2$)$_q$— (q represents an integer from 0 to 3), more preferably, q is 0.

Preferably, G is a $C_{1-6}$ alkoxycarbonyl group.

More specifically, in the above formula (I), the optionally substituted amino group represented by R is represented by —N($R^1$)($R^2$), wherein $R^1$ and $R^2$ are the same or different and each represents a hydrogen atom, an optionally substituted hydrocarbon residue, an optionally substituted acyl group, an optionally substituted sulfonyl group or an optionally substituted heterocyclic group, preferably, a hydrogen atom, an optionally substituted hydrocarbon residue or an optionally substituted heterocyclic group, or they may bind together to form a nitrogen-containing ring.

Examples of the optionally substituted hydrocarbon residue represented by $R^1$ or $R^2$ include aliphatic hydrocarbon residues, alicyclic hydrocarbon residues, alicyclic-aliphatic hydrocarbon residues, aromatic aliphatic hydrocarbon residues and aromatic hydrocarbon residues.

Examples of the aliphatic hydrocarbon residue include $C_{1-8}$ saturated aliphatic hydrocarbon residues (e.g., methyl, ethyl, propyl, isopropyl, butyl, isobutyl, sec-butyl, tert-butyl, pentyl, isopentyl, neopentyl, tert-pentyl, hexyl, isohexyl, heptyl and octyl) and $C_{2-8}$ unsaturated aliphatic hydrocarbon residues (e.g., vinyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, 1-heptenyl, 1-octenyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-heptynyl and 1-octynyl).

Examples of the alicyclic hydrocarbon residue include $C_{3-7}$ saturated alicyclic hydrocarbon residues (e.g., cyclopropyl, cyclobutyl, cyclopentyl, cyclohexyl and cycloheptyl) and $C_{5-7}$ unsaturated alicyclic hydrocarbon residues (e.g., 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl and 2,4-cycloheptadienyl).

Examples of the alicyclic-aliphatic hydrocarbon residue include groups resulting from binding of one of the above-described alicyclic hydrocarbon residues and one of the above-described aliphatic hydrocarbon residues, and having 4 to 9 carbon atoms (e.g., cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl and cycloheptylethyl).

Examples of the aromatic aliphatic hydrocarbon residue include $C_{7-9}$ phenylalkyls (e.g., benzyl, phenethyl, 1-phenylethyl, 3-phenylpropyl, 2-phenylpropyl and 1-phenylpropyl) and $C_{11-13}$ naphthylalkyls (e.g., α-naphthylmethyl, α-naphthylethyl, β-naphthylmethyl and β-naphthylethyl).

Examples of the aromatic hydrocarbon residue include phenyls and naphthyls (α-naphthyl and β-naphthyl).

Examples of the acyl group represented by $R^1$ and $R^2$ include (i) formyl and (ii) a group formed by binding a $C_{1-10}$ alkyl group, a $C_{2-10}$ alkenyl group, a $C_{2-10}$ alkynyl group or an aromatic group to a carbonyl group (e.g., acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl or nicotinoyl).

Examples of the sulfonyl group represented by $R^1$ and $R^2$ include a group formed by binding a $C_{1-10}$ alkyl group, a $C_{2-10}$ alkenyl group, a $C_{2-10}$ alkynyl group or an aromatic group to sulfonyl group (e.g., methanesulfonyl, ethanesulfonyl or benzensulfonyl).

Examples of the optionally substituted heterocyclic group represented by $R^1$ or $R^2$ include (i) 5- to 7-membered heterocyclic groups containing one sulfur atom, nitrogen atom or oxygen atom, (ii) 5- or 6-membered heterocyclic groups containing 2 to 4 nitrogen atoms, and (iii) 5- or 6-membered heterocyclic groups containing 1 or 2 nitrogen atoms and one sulfur atom or oxygen atom, and (iv) these heterocyclic groups may be condensed with a 6- membered ring containing 2 or fewer nitrogen atoms, a benzene ring or a 5-membered ring containing one sulfur atom.

Examples of the heterocyclic group of the optionally substituted heterocyclic group represented by $R^1$ or $R^2$ include aromatic mono-cyclic heterocyclic groups, aromatic condensed heterocyclic groups and non-aromatic heterocyclic groups.

Specific examples of the heterocyclic group of the optionally substituted heterocyclic groups represented by $R^1$ or $R^2$ include (i) aromatic monocyclic heterocyclic groups (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyrimidinyl, pyridazinyl, pyrazinyl and triazinyl), (ii) aromatic condensed heterocyclic groups (e.g., benzofuranyl, isobenzofuranyl, benzo[b]thienyl, indolyl, isoindolyl, 1H-indazolyl, benzimidazolyl, benzoxazolyl, 1,2-benzisothiazolyl, 1H-benzotriazolyl, quinolyl, isoquinolyl, cinnolinyl, quinazolinyl, quinoxalinyl, phthalazinyl, naphthylizinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl and 1,2,4-triazolo[4,3-b]pyridazinyl), and (iii) non-aromatic heterocyclic groups (e.g., oxylanyl, azetidinyl, oxetanyl, thietanyl, pyrrolidinyl, tetrahydrofuryl, thiolanyl, piperizinyl, tetrahydropyranyl, morpholinyl and thiomorpholinyl, piperazinyl).

$R^1$ and $R^2$ may bind to each other to form a ring, particularly a nitrogen-containing 5- to 7-membered ring. Examples of such —N($R^1$)($R^2$) include 1-pyrrolidinyl, 1-imidazolizinyl, 1-pyrazolizinyl, 1-piperidyl (piperidino), 1-piperazinyl, 4-morpholinyl (morpholino), 4-thiomorpholinyl, homopiperazin-1-yl, pyrazol-1-yl, imidazol-1-yl, 1,2,4-triazol-1-yl, 1,2,4-triazol-4-yl, 1,2,3-triazol-1-yl, 1,2,3-triazol-2-yl, tetrazol-1-yl, benzimidazol-1-yl, indol-1-yl and 1H-indazol-1-yl.

The hydrocarbon residue of the optionally substituted hydrocarbon residue represented by $R^1$ or $R^2$ is preferably a linear or branched $C_{1-6}$ alkyl, more preferably a $C_{1-4}$ linear or branched alkyl. Specifically, methyl, ethyl, propyl, isopropyl, butyl and the like are preferred.

When $R^1$ and $R^2$ bind to each other to form a nitrogen-containing ring, the —N($R^1$)($R^2$) is preferably 1,2,4-triazol-1-yl, imidazol-1-yl, morpholino (4-morpholinyl), piperidino (1-piperidyl), pyrrolidino or the like.

The hydrocarbon residue, acyl group, sulfonyl group and heterocyclic group represented by $R^1$ or $R^2$ may have at any possible positions on the chain or ring thereof 1 to 3 substituents.

Examples of the substituent on the hydrocarbon residue, acyl group, sulfonyl group and heterocyclic group represented by $R^1$ or $R^2$ include aliphatic chain hydrocarbon groups, alicyclic hydrocarbon groups, aryl groups, aromatic heterocyclic groups, non-aromatic heterocyclic groups, halogen atoms, optionally substituted amino groups, amidino groups, optionally substituted acyl groups, optionally substituted hydroxy groups, optionally substituted thiol groups, carboxyl groups that may be esterified or amidated, aralkyl groups (e.g., aryl $C_{1-6}$ alkyl groups), carbamoyl groups, N-mono-substitutional carbamoyl groups (e.g., methylcarbamoyl, ethylcarbamoyl and phenylcarbamoyl), N,N-di-substituted carbamoyl groups (e.g., N,N-dimethylcarbamoyl, N,N-di-ethyl-carbamoyl, piperidinocarbamoyl and morpholinocarbamoyl), sulfamoyl groups, N-mono-substitutional sulfamoyl groups (e.g., methylsulfamoyl, ethylsulfamoyl, phenylsulfamoyl and p-toluenesulfamoyl), N,N-di-substitutional sulfamoyl groups (e.g., N,N-dimethylsulfamoyl, N-methyl-N-phenylsulfamoyl, piperidinosulfamoyl and morpholinosulfamoyl), mercapto group, sulfo group, cyano group, azide group, nitro group and nitroso group.

Examples of the aliphatic chain hydrocarbon group as a substituent for the hydrocarbon residue, acyl group, sulfonyl group and heterocyclic group represented by $R^1$ or $R^2$ include linear or branched aliphatic hydrocarbon groups such as alkyl groups (preferably $C_{1-10}$ alkyl groups), alkenyl groups (preferably $C_{2-10}$ alkenyl groups) and alkynyl groups (preferably $C_{2-10}$ alkynyl groups). Examples of the preferred alkyl groups include methyl, ethyl, propyl, isopropyl, butyl, isobutyl, sec-butyl, tert-butyl, pentyl, isopentyl, neopentyl, tert-pentyl, 1-ethylpropyl, hexyl, isohexyl, 1,1-dimethylbutyl, 2,2-dimethylbutyl, 3,3-dimethylbutyl, 2-ethylbutyl, hexyl, pentyl, octyl, nonyl and decyl. Examples of the preferred alkenyl group include vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl. Examples of the preferred alkynyl group include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

Examples of the alicyclic hydrocarbon group as a substituent for the hydrocarbon residue, acyl group, sulfonyl group and heterocyclic group represented by $R^1$ or $R^2$ include saturated or unsaturated $C_{3-8}$ alicyclic hydrocarbon groups such as $C_{3-8}$ cycloalkyl groups, $C_{3-8}$ cycloalkenyl groups and $C_{4-8}$ cycloalkadienyl groups. Examples of the preferred $C_{3-8}$ cycloalkyl group include cyclopropyl, cyclobutyl, cyclopentyl, cyclohexyl, cycloheptyl, cyclooctyl, bicyclo[2.2.1]heptyl, bicyclo[2.2.2]octyl and bicyclo[3.2.1]octyl. Examples of the preferred $C_{3-8}$ cycloalkenyl group include 2-cyclopenten-1-yl, 3-cyclopenten-1-yl, 2-cyclohexen-1-yl and 3-cyclohexen-1-yl. Examples of the preferred $C_{4-8}$ cycloalkadienyl group include 2,4-cyclopentadien-1-yl, 2,4-cyclohexadien-1-yl and 2,5-cyclohexadien-1-yl.

Examples of the aryl group as a substituent for the hydrocarbon residue, acyl group, sulfonyl group and heterocyclic group represented by $R^1$ or $R^2$ include a monocyclic or condensed polycyclic aromatic hydrocarbon group. Examples of the preferred aryl group include phenyl, naphthyl, anthryl, phenanthryl and acenaphthylenyl, more preferably phenyl, 1-naphthyl and 2-naphthyl.

Examples of the preferred aromatic heterocyclic group as a substituent for the hydrocarbon residue, acyl group, sulfonyl group and heterocyclic group represented by $R^1$ or $R^2$ include aromatic monocyclic heterocyclic groups (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazol-yl, 1,3,4-thiadiazolyl, 1,2,3-triazolyl, 1,2,4-triazolyl, tetrazolyl, pyridyl, pyridazinyl, pyrimidinyl, pyrazinyl and triazinyl), and aromatic condensed heterocyclic groups (e.g., benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthylizinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl and 1,2,4-triazolo[4,3-b]pyridazinyl).

Examples of the preferred non-aromatic heterocyclic group as a substituent for the hydrocarbon residue, acyl group, sulfonyl group and heterocyclic group represented by $R^1$ or $R^2$ include oxylanyl, azetidinyl, oxetanyl, thietanyl, pyrrolidinyl, tetrahydrofuryl, thiolanyl, piperidyl, tetrahydropyranyl, morpholinyl, thiomorpholinyl and piperazinyl.

Examples of the halogen atom as a substituent for the hydrocarbon residue, acyl group, sulfonyl group and heterocyclic group represented by $R^1$ or $R^2$ include fluorine, chlorine, bromine and iodine, preferably, fluorine and chlorine.

Examples of the optionally substituted amino group as a substituent for the hydrocarbon residue, acyl group, sulfonyl group and heterocyclic group represented by $R^1$ or $R^2$ include unsubstituted amino group, N-monosubstituted amino groups and N,N-di-substituted amino groups. Examples of the substituted amino group include amino groups having 1 or 2 $C_{1-10}$ alkyl groups, $C_{2-10}$ alkenyl groups, $C_{2-10}$ alkynyl groups, aromatic groups, heterocyclic groups or $C_{1-10}$ acyl groups as the substituents (e.g., methylamino, dimethylamino, ethylamino, diethylamino, dibutylamino, diallylamino, cyclohexylamino, phenylamino, N-methyl-N-phenylamino, acetylamino, propionylamino, benzoylamino and nicotinoylamino).

Example of the acyl group as a substituent for the hydrocarbon residue, acyl group, sulfonyl group and heterocyclic group represented by $R^1$ or $R^2$ include (i) formyl and (ii) groups resulting from binding of a $C_{1-10}$ alkyl group, $C_{2-10}$ alkenyl group, $C_{2-10}$ alkynyl group or aromatic group to a carbonyl group (e.g., acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl and nicotinoyl).

Examples of the optionally substituted hydroxy group as a substituent for the hydrocarbon residue and heterocyclic group represented by $R^1$ or $R^2$ include unsubstituted hydroxy group and a hydroxy group having an appropriate substituent, particularly a substituent to be used as a hydroxy-protecting group, (e.g., alkoxy, alkenyloxy, alkynyloxy, aralkyloxy, acyloxy or aryloxy).

The alkoxy is preferably a $C_{1-10}$ alkoxy (e.g., methoxy, ethoxy, propoxy, isopropoxy, butoxy, isobutoxy, sec-butoxy, tert-butoxy, pentyloxy, isopentyloxy, neopentyloxy, hexyloxy, heptyloxy, nonyloxy, cyclobutoxy, cyclopentyloxy or cyclohexyloxy).

The alkenyloxy is preferably a $C_{2-10}$ alkenyloxy (e.g., allyloxy, crotyloxy, 2-pentenyloxy, 3-hexenyloxy, 2-cyclopentenylmethoxy or 2-cyclohexenylmethoxy).

The alkynyloxy is preferably a $C_{2-10}$ alkynyloxy (e.g., ethynyloxy or 2-propynyloxy).

The aralkyloxy is preferably, for example, a phenyl-$C_{1-4}$ alkyloxy (e.g., benzyloxy or phenethyloxy).

The acyloxy is preferably a $C_{2-4}$ alkanoyloxy (e.g., acetyloxy, propionyloxy, butyryloxy or isobutyryloxy), a $C_{3-4}$ alkenoyloxy or a $C_{3-4}$ alkynoyloxy.

The aryloxy is preferably, for example, phenoxy or 4-chlorophenoxy.

Examples, of the optionally substituted thiol group as a substituent for the hydrocarbon residue, acyl group, sulfonyl group and heterocyclic group represented by $R^1$ or $R^2$ include unsubstituted thiol group and thiol group having an appropriate substituent, particularly a substituent to be used as a thiol-protecting group (e.g., alkylthio, alkenylthio, alkynylthio, aralkylthio, acylthio or arylthio).

The alkylthio is preferably, for example, a $C_{1-10}$ alkylthio (e.g., methylthio, ethylthio, propylthio, isopropylthio, butylthio, isobutylthio, sec-butylthio, tert-butylthio, pentylthio, isopentylthio, neopentylthio, hexylthio, heptylthio, nonylthio, cyclobutylthio, cyclopentylthio or cyclohexylthio).

The alkenylthio is preferably, for example, a $C_{2-10}$ alkenylthio group (e.g., allylthio, crotylthio, 2-pentenylthio, 3-hexenylthio, 2-cyclopentenylmethylthio or 2-cyclohexenylmethylthio).

The alkynylthio is preferably, for example, a $C_{2-10}$ alkynylthio (e.g., ethynylthio or 2-propynylthio).

The aralkylthio is preferably, for example, phenyl-$C_{1-4}$ alkylthios (e.g., benzylthio or phenethylthio).

The acylthio is preferably, for example, a $C_{2-4}$ alkanoylthio (e.g., acetylthio, propionylthio, butyrylthio or isobutyrylthio).

The arylthio is preferably, for example, phenylthio or 4-chlorophenylthio.

Examples of the optionally esterified carboxyl group as a substituent for the hydrocarbon residue, acyl group, sulfonyl group and heterocyclic group represented by $R^1$ or $R^2$ include carboxyl group and alkyloxycarbonyl groups, alkenyloxycarbonyl groups, alkynyloxycarbonyl groups, aralkyloxycarbonyl groups, acyloxycarbonyl groups and aryloxycarbonyl groups.

Examples of the alkyl group of the alkyloxycarbonyl group include $C_{1-6}$ alkyl groups (e.g., methyl, ethyl, propyl, isopropyl, butyl, isobutyl, sec-butyl and tert-butyl).

Examples of the alkenyl group of the alkenyloxycarbonyl group include $C_{2-6}$ alkenyl groups (e.g., vinyl, allyl, 1-propenyl, isopropenyl, 1-butenyl, 2-butenyl and 2-methylallyl).

Examples of the alkynyl group of the alkynyloxycarbonyl groups include $C_{2-6}$ alkynyl groups (e.g., ethynyl and 2-propynyl).

The aralkyl group of the aralkyloxycarbonyl groups is aryl-alkyl groups and examples of the aryl group of the aryl-alkyl group include phenyl and naphthyl which may be substituted with the same substituents as those of the aryl group as exemplified above with respect to the hydrocarbon residue represented by $R^1$ or $R^2$. The alkyl group of the arylalkyl group is preferably $C_{1-6}$ alkyl groups (e.g., methyl, ethyl, propyl and butyl). Preferred examples of the aralkyl groups, i.e., aryl-alkyl groups, include benzyl, phenethyl, 3-phenylpropyl, (1-naphthyl)methyl and (2-naphthyl)methyl, more preferably, benzyl and phenethyl.

Examples of the acyl group of the acyloxycarbonyl group include formyl, $C_{2-4}$ alkanoyl groups, $C_{3-4}$ alkenoyl groups and $C_{3-4}$ alkynoyl groups.

Examples of the aryl group of the aryloxycarbonyl group include phenyl and naphthyl.

The amidated carboxyl groups as a substituent for the hydrocarbon residue, acyl group, sulfonyl group and heterocyclic group represented by $R^1$ or $R^2$ include, for example, those represented by —CON($R^1$)($R^2$) ($R^1$ and $R^2$ are as defined above).

The above-described substituents on the hydrocarbon residue, acyl group, sulfonyl group and heterocyclic group represented by $R^1$ or $R^2$ may further have at any possible positions one or more, preferably 1 to 3 appropriate substituents. Examples of the substituents include those as exemplified above with respect to the substituents on the hydrocarbon residue, acyl group, sulfonyl group and heterocyclic group represented by $R^1$ or $R^2$, specifically $C_{1-10}$ alkyl groups, $C_{2-10}$ alkenyl groups, $C_{2-10}$ alkynyl groups, $C_{3-8}$ cycloalkyl groups, $C_{3-8}$ cycloalkenyl groups, $C_{4-8}$ cycloalkadienyl groups, aryl groups, aromatic heterocyclic groups, non-aromatic heterocyclic groups, aralkyl groups (e.g., aryl $C_{1-6}$ alkyl groups), amino group, N-mono-substituted amino groups, N,N-di-substituted amino groups, amidino groups, acyl groups, carbamoyl group, N-mono-substituted carbamoyl groups, (e.g., methylcarbamoyl, ethylcarbamoyl and phenylcarbamoyl), N,N-di-substituted carbamoyl groups (e.g., N,N-diethylcarbamoyl, piperidinocarbamoyl and morpholinocarbamoyl), sulfamoyl group, N-mono-substituted sulfamoyl groups (e.g., methylsulfamoyl, ethylsulfamoyl, phenylsulfamoyl and p-toluenesulfamoyl), N,N-di-substituted sulfamoyl groups (e.g., N,N-dimethyl-sulfamoyl, N-methyl-N-phenylsulfamoyl, piperidinosulfamoyl and morpholinosulfamoyl), carboxyl group, $C_{1-10}$ alkoxycarbonyl groups (e.g., methoxycarbonyl, ethoxycarbonyl, isopropoxycarbonyl, sec-butoxycarbonyl, isobutoxycarbonyl and tert-butoxycarbonyl), hydroxy group, $C_{1-10}$ alkoxy groups, $C_{2-10}$ alkenyloxy groups, $C_{3-7}$ cycloalkyloxy groups, aralkyloxy groups, aryloxy groups, mercapto group, $C_{1-10}$ alkylthio groups, aralkylthio groups, arylthio groups, sulfo group, cyano group, azide group, nitro group, nitroso group, and halogens.

Examples of the optionally substituted heterocyclic group represented by R in the above formula (I) include the same heterocyclic groups as those exemplified above with respect to $R^1$ or $R^2$.

Examples of the optionally substituted heterocyclic group represented by R include (i) 5- to 7-membered heterocyclic groups containing one sulfur atom, nitrogen atom or oxygen atom, (ii) 5- or 6-membered heterocyclic groups containing 2 to 4 nitrogen atoms, and (iii) 5- or 6-membered heterocyclic groups containing 1 or 2 nitrogen atoms and one sulfur atom or oxygen atom, and (iv) these heterocyclic groups may be condensed with a 6-membered ring containing 2 or fewer nitrogen atoms, a benzene ring or a 5-membered ring containing one sulfur atom.

These heterocyclic groups may have at any possible positions on the ring thereof 1 to 3 substituents. Examples of the substituents include the same groups as those exemplified above with respect to the substituent on the hydrocarbon residue and heterocyclic group represented by $R^1$ or $R^2$, specifically $C_{1-10}$ alkyl groups, $C_{2-10}$ alkenyl groups, $C_{2-10}$ alkynyl groups, $C_{3-8}$ cycloalkyl groups, $C_{3-8}$ cycloalkenyl groups, $C_{4-8}$ cycloalkadienyl groups, aryl groups, aromatic heterocyclic groups, non-aromatic heterocyclic groups, aralkyl groups (e.g., aryl $C_{1-6}$ alkyl groups), amino group, N-mono-substituted amino groups, N,N-di-substituted amino groups, amidino groups, acyl groups, carbamoyl group, N-mono-substituted carbamoyl groups, (e.g., methylcarbamoyl, ethylcarbamoyl and phenylcarbamoyl), N,N-di-substituted carbamoyl groups (e.g., N,N-dimethylcarbamoyl, N,N-diethylcarbamoyl, piperidinocarbamoyl and morpholinocarbamoyl), sulfamoyl group, N-mono-substituted sulfamoyl groups (e.g., methylsulfamoyl, ethyl-sulfamoyl, phenylsulfamoyl and p-toluenesulfamoyl), N,N-di-substituted sulfamoyl groups (e.g., N,N-dimethyl-sulfamoyl, N-methyl-N-phenylsulfamoyl, piperidinosulfamoyl and morpholinosulfamoyl), carboxyl group, $C_{1-10}$ alkoxycarbonyl groups (e.g., methoxycarbonyl, ethoxycarbonyl, isopropoxycarbonyl, sec-butoxycarbonyl, isobutoxycarbonyl and tert-butoxycarbonyl), hydroxy group, $C_{1-10}$ alkoxy groups, $C_{2-10}$ alkenyloxy groups, $C_{3-7}$ cycloalkyloxy groups, aralkyloxy groups, aryloxy groups, mercapto group, $C_{1-10}$ alkylthio groups, aralkylthio groups, arylthio groups, sulfo group, cyano group, azide group, nitro group, nitroso group, and halogens.

These substituents on the heterocyclic groups may further have at any possible positions 1 or more, preferably 1 to 3 appropriate substituents. Examples of the substituents include the same groups as those exemplified above, specifically $C_{1-10}$ alkyl groups, $C_{2-10}$ alkenyl groups, $C_{2-10}$ alkynyl groups, $C_{3-7}$ cycloalkyl groups, $C_{3-7}$ cycloalkenyl groups, $C_{4-8}$ cycloalkadienyl groups, aryl groups, aromatic heterocyclic groups, non-aromatic heterocyclic groups, aralkyl groups (e.g., aryl $C_{1-6}$ alkyl groups), amino group, N-mono-substituted amino groups, N,N-di-substituted amino groups, amidino groups, acyl groups, carbamoyl group, N-mono-substituted carbamoyl groups, N,N-di-substituted carbamoyl groups, sulfamoyl group, N-mono-substituted sulfamoyl groups, N,N-di-substituted sulfamoyl groups, carboxyl group, $C_{1-10}$ lower alkoxycarbonyl groups, hydroxy group, $C_{1-10}$ lower alkoxy groups, $C_{2-10}$ lower alkenyloxy groups, $C_{3-7}$ cycloalkyloxy groups, aralkyloxy groups, aryloxy groups, mercapto group, $C_{1-10}$ lower alkylthio groups, aralkylthio groups, arylthio groups, sulfo group, cyano group, azide group, nitro group, nitroso group and halogens.

Preferred examples of the optionally substituted heterocyclic group represented by R include 2-imidazolyl, 1,2,4-triazol-3-yl, 2-thiazolyl, 2-oxazolyl, 2-pyridyl, 3-pyridyl, 4-pyridyl and 2-benzimidazolyl.

In the above formula (I), X represents an oxygen atom, a sulfur atom which may be oxidized or —(CH2)q— (q represents an integer from 0 to 5, preferably an integer from 0 to 3). Examples of the optionally oxidized sulfur atom represented by X include thio group, sulfinyl group and sulfonyl group, preferably, thio group. Regarding the —(CH2)q— represented by X, q is preferably 0.

In the above formula (I), Y represents C-G (G represents a carboxyl group which may be esterified). The optionally esterified carboxyl group represented by G is that represented by the formula —COOR$^3$ (R$^3$ represents a hydrogen atom, an alkyl group, an aralkyl group or an aryl group).

Examples of the alkyl group represented by R$^3$ include $C_{1-6}$ alkyl groups (e.g., methyl, ethyl, propyl, isopropyl, butyl, isobutyl, sec-butyl and tert-butyl). The aralkyl group represented by R$^3$ is an alkyl group having an aryl group as a substituent (e.g., aryl $C_{1-6}$ alkyl groups). Examples of the aryl groups in the arylalkyl groups include phenyl and naphthyl. The aralkyl group represented by R$^3$ is preferably, for example, benzyl, phenethyl, 3-phenylpropyl, (1-naphthyl)methyl or (2-naphthyl)methyl.

Y is preferably C—COOR$^3$ (R$^3$ is a $C_{1-4}$ alkyl group), more preferably C—COOC$_2$H$_5$.

In the above formula (I), M represents a hydrogen atom, an optionally substituted acyl group, an optionally substituted carbamoyl group, an optionally substituted alkoxycarbonyl group, an optionally substituted thiocarbamoyl group or an optionally substituted sulfonyl group.

Examples of the optionally substituted acyl group represented by M include the same acyl groups as those exemplified above with respect to the substituents for the hydrocarbon residue, acyl group, sulfonyl group and heterocyclic group represented by R$^1$ or R$^2$, for example, acetyl, benzoyl or 4-chlorobenzoyl.

Examples of the optionally substituted carbamoyl group represented by M include those represented by R$^1$NHCO (R$^1$ is as defined above), for example, phenylcarbamoyl or methylcarbamoyl.

Examples of the optionally substituted alkoxycarbonyl represented by M include those represented by —COOR$^3$ (R$^3$ is as defined above), for example, ethoxycarbonyl or benzyloxycarbonyl.

Examples of the optionally substituted thiocarbamoyl group represented include those represented by R$^1$NHCS (R$^1$ is as defined above), for example, phenylthiocarbamoyl or methylthiocarbamoyl.

Examples of the optionally substituted sulfonyl group represented by M include those represented by R$^1$SO$_2$ (R$^1$ is as defined above), for example, benzenesulfonyl.

In the above formula (I), the ring B together with the carbon double bond of the adjacent thiophene ring forms an optionally substituted 5- to 7-membered ring containing a nitrogen atom, preferably an optionally substituted 6-membered ring containing a nitrogen atom. When the 6-membered ring containing a nitrogen atom represented by the ring B is a fully saturated 6-membered ring, n of the above formula (I) is 0 and, when it is a partially saturated 6-membered ring, n of the above formula (I) is 0 or 1. Specifically, preferred examples of the ring B and (M)n include the groups of the following formulas:

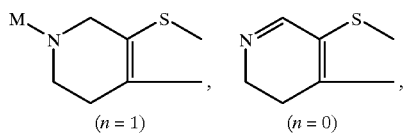

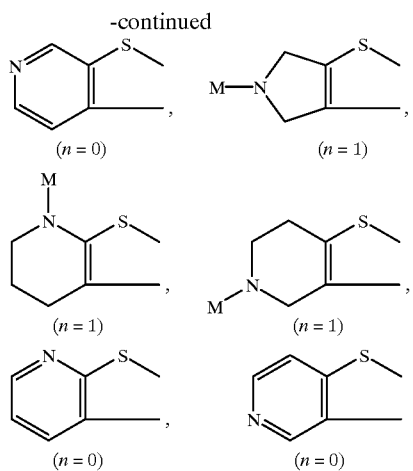

In the above formula (I), the ring A may have at any possible positions thereon 1 to 4, preferably 1 or 2 substituents, which may be the same or different. Examples of the substituents on the ring A include halogen atoms, nitro group, optionally substituted alkyl groups, optionally substituted hydroxy groups, optionally substituted thiol groups, optionally substituted amino groups, acyl groups, optionally esterified carboxyl groups and optionally substituted aromatic ring groups.

Examples of the halogens as the substituents on the ring A include fluorine, chlorine, bromine and iodine, preferably, fluorine and chlorine.

Examples of the optionally substituted alkyl groups as the substituents on the ring A include $C_{1-10}$ linear alkyl groups, $C_{3-10}$ branched alkyls or $C_{3-10}$ cyclic alkyls, including methyl, ethyl, propyl, isopropyl, butyl, isobutyl, sec-butyl, tert-butyl, pentyl, isopentyl, neopentyl, hexyl, heptyl, octyl, nonyl, decyl, cyclopropyl, cyclobutyl, cyclopentyl, cyclohexyl and cycloheptyl.

Examples of the optionally hydroxy groups as the substituents for the ring A include unsubstituted hydroxy group and hydroxy groups having an appropriate substituent, particularly a substituent to be used as a hydroxy-protecting group (e.g., alkoxy, alkenyloxy, alkynyloxy, aralkyloxy, acyloxy or aryloxy). The alkoxy group is preferably a $C_{1-10}$ alkoxy group (e.g., methoxy, ethoxy, propoxy, isopropoxy, butoxy, isobutoxy, sec-butoxy, tert-butoxy, pentyloxy, isopentyloxy, neopentyloxy, hexyloxy, heptyloxy, nonyloxy, cyclobutoxy, cyclopentyloxy or cyclohexyloxy). The alkenyloxy group is preferably a $C_{2-10}$ alkenyloxy group (e.g., allyloxy, crotyloxy, 2-pentenyloxy, 3-hexenyloxy, 2-cyclopentenylmethoxy or 2-cyclohexenylmethoxy). The alkynyloxy group is preferably a $C_{2-10}$ alkynyloxy group (e.g., ethynyloxy or 2-propynyloxy). The aralkyloxy group is, for example, a phenyl-$C_{1-4}$ alkyloxy group (e.g., benzyloxy or phenethyloxy). The acyloxy group is preferably a $C_{2-4}$ alkanoyloxy group (e.g., acetyloxy, propionyloxy, butyryloxy or isobutyryloxy). The aryloxy group is, for example, phenoxy or 4-chlorophenoxy.

Examples of the optionally substituted thiol groups as the substituents for the ring A include unsubstituted thiol group and thiol groups having an appropriate substituent, particularly a substituent to be used as a thiol-protecting group, (e.g., alkylthio, alkenylthio, alkynylthio, aralkylthio, acylthio or arylthio). The alkylthio group is preferably a $C_{1-10}$ alkylthio group (e.g., methylthio, ethylthio, propylthio, iso-propylthio, butylthio, isobutylthio, sec-butylthio, tert-butylthio, pentylthio, isopentylthio, neopentylthio, hexylthio, heptylthio, nonylthio, cyclobutylthio, cyclopentylthio or cyclohexylthio). The alkenylthio group is preferably a $C_{2-10}$ alkenylthio group (e.g., allylthio, crotylthio, 2-pentenylthio, 3-hexenylthio, 2-cyclopentenylmethoxy or 2-cyclohexenylmethoxy). The alkynylthio group is preferably a $C_{2-10}$ alkynylthio group (e.g., ethynylthio or 2-propynylthio). The aralkylthio group is, for example, phenyl-$C_{1-4}$ alkylthio group (e.g., benzylthio or phenethylthio). The acylthio group is preferably an alkanoylthio group having 2 to 4 carbon atoms (e.g., acetylthio, propionylthio, butyrylthio or isobutyrylthio). The arylthio is preferably, for example, phenylthio or 4-chlorophenylthio.

Examples of the optionally substituted amino groups as the substituents for the ring A include unsubstituted amino group and substituted amino groups, e.g., amino groups having 1 or 2 $C_{1-10}$ alkyl groups, $C_{2-10}$ alkenyl groups, $C_{2-10}$ alkynyl groups, aromatic groups, heterocyclic groups or $C_{1-10}$ acyl groups as substituents (e.g., methylamino, dimethylamino, ethylamino, diethylamino, dibutylamino, diallylamino, cyclohexylamino, phenylamino, N-methyl-N-phenylamino, acetylamino, propionylamino, benzoylamino or nicotinoylamino).

Examples of the acyl groups as the substituents for the ring A include formyl and groups resulting from binding of a $C_{1-10}$ alkyl, $C_{2-10}$ alkenyl, $C_{2-10}$ alkynyl or aromatic group to carbonyl group (e.g., acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl or nicotinoyl).

Examples of the optionally esterified carboxyl groups as the substituents for the ring A include, in addition to carboxyl group, alkyloxycarbonyl groups, alkenyloxycarbonyl groups, alkynyloxycarbonyl groups, aralkyloxycarbonyl groups, acyloxycarbonyl groups and aryloxycarbonyl groups. These are represented by the formula —$COOR^4$ ($R^4$ is a hydrogen atom, a $C_{1-6}$ alkyl group, an aryl $C_{1-6}$ alkyl group or an aryl group). The alkyl groups of the alkyloxy-carbonyl groups include $C_{1-6}$ alkyl groups (e.g., methyl, ethyl, propyl, isopropyl, butyl, isobutyl, sec-butyl and tert-butyl). The aralkyl groups in the aralkyloxycarbonyl groups are aryl-alkyl groups. Examples of the aryl groups of the aryl-alkyl groups include phenyl and naphthyl, which may have the same substituents as those exemplified above with respect to the substituents of the aryl groups of the hydrocarbon group represented by $R^1$ or $R^2$. The alkyl groups in the aryl-alkyl groups are preferably $C_{1-6}$ alkyl groups (e.g., methyl, ethyl, propyl or butyl). Preferred examples of the aralkyl groups, i.e., aryl-alkyl groups, include benzyl, phenethyl, 3-phenylpropyl, (1-naphthyl)methyl and (2-naphthyl)methyl, more preferably, benzyl, phenethyl and the like.

Examples of the optionally substituted aromatic ring groups as the substituents for the ring A include $C_{6-14}$ aromatic hydrocarbon residues such as phenyl, naphthyl and anthryl, and heteroaromatic residues such as pyridyl, furyl, thienyl, imidazolyl and thiazolyl.

The substituent(s) on the ring A are preferably present at the 3- and/or 4-positions of the ring A. When these substituents on the ring A are adjacent to each other, they may bind together to form a ring represented by —$(CH_2)_m$— or —O—$(CH_2)_l$—O— (m represents an integer from 3 to 5, and 1 represents an integer from 1 to 3), inclusive 5-to 7-membered rings formed together with the carbon atoms of the benzene ring.

The ring A is preferably substituted with at least one $C_{1-6}$ alkoxy group, preferably a $C_{1-3}$ alkoxy group, and more preferably a methoxy group, or hydroxy group.

More preferably, the ring A is substituted by 2 alkoxy groups, which may be the same or different, preferably two $C_{1-3}$ alkoxy groups, more preferably 2 methoxy groups. In particular, it is preferred that the ring A is substituted with two methoxy groups at the 3- and 4-positions.

Among the compounds represented by the above formula (I), those wherein n is 1; M is a hydrogen atom, benzoyl, 4-chlorobenzoyl, acetyl, phenylcarbamoyl, ethoxycarbamoyl, phenylsulfonyl or benzyloxycarbonyl; the ring B is a 6-membered nitrogen-containing ring; Y is C-G (G is ethoxycarbonyl); —X—R— is N,N-diethylamino, 1,2,4-triazol-1-yl, 3-(1,2,4-triazol-1-yl)propyl, 2-oxopyrrolidin-1-yl or 1-methylimidazol-2-ylthio; and the ring A is substituted with two methoxy groups at the 3- and 4-positions are particularly preferred.

Specific examples of the compound of the formula (I) are:

ethyl 7-benzoyl-2-(N,N-diethylaminomethyl)-4-(3,4-dimethoxyphenyl)-5,6,7,8-tetrahydrothieno[2,3-b:5,4-c']dipyridine-3-carboxylate, ethyl 7-(4-chlorobenzoyl)-2-(N,N-diethylaminomethyl)-4-(3,4-dimethoxyphenyl)-5,6,7,8-tetrahydrothieno[2,3-b:5,4-c']dipyridine-3-carboxylate, ethyl 2-(N,N-diethylaminomethyl)-4-(3,4-dimethoxyphenyl)-5,6,7,8-tetrahydrothieno[2,3-b:5,4-c']dipyridine-3-carboxylate, ethyl 2-(N,N-diethylaminomethyl)-4-(3,4-dimethoxyphenyl)thieno[2,3-b:5,4-c']dipyridine-3-carboxylate, ethyl 2-(N,N-diethylaminomethyl)-4-(3,4-dimethoxyphenyl)-7-phenylcarbamoyl-5,6,7,8-tetrahydrothieno[2,3-b:5,4-c']dipyridine-3-carboxylate, ethyl 7-acetyl-2-(N,N-diethylaminomethyl)-4-(3,4-dimethoxyphenyl)-5,6,7,8-tetrahydrothieno[2,3-b:5,4-c']dipyridine-3-carboxylate, ethyl 7-(4-chlorobenzoyl)-4-(3,4-dimethoxyphenyl)-5,6,7,8-tetrahydro-2-[3-(1,2,4-triazol-1-yl)propyl]thieno[2,3-b:5,4-c']dipyridine-3-carboxylate, ethyl 7-(4-chlorobenzoyl)-4-(3,4-dimethoxyphenyl)-5,6,7,8-tetrahydro-2-[4-(1,2,4-triazol-1-yl)butyl]thieno[2,3-b:5,4-c']dipyridine-3-carboxylate, and ethyl 4-(4-ethylphenyl)-5,6,7,8-tetrahydro-2-(N,N-diethylaminomethyl)thieno[2,3-b:5,4-c']dipyridine-3-carboxylate.

The salts of the compound of the above formula (I) of the present invention are preferably pharmaceutically acceptable salts, for example, salts with inorganic bases, salts with organic bases, salts with inorganic acids, salts with organic acids and salts with basic or acidic amino acids. The preferred salts with inorganic bases include alkali metal salts such as sodium salt and potassium salt; alkaline earth metal salts such as calcium salt and magnesium salt; and aluminum salt and ammonium salt. The preferred salts with organic bases include salts with trimethylamine, triethylamine, pyridine, picoline, ethanolamine, diethanolamine, triethanolamine, dicyclohexylamine and N,N'-dibenzylethylenediamine. The preferred salts with inorganic acids include salts with hydrochloric acid, hydrobromic acid, nitric acid, sulfuric acid and phosphoric acid. The preferred salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid and p-toluene-sulfonic acid. The preferred salts with basic amino acids include salts with arginine, lysine and ornithine. The preferred salts with acidic amino acids include salts with as-par-tic acid and glutamic acid.

The compounds of the above formula (I) can, for example, be produced as follows:

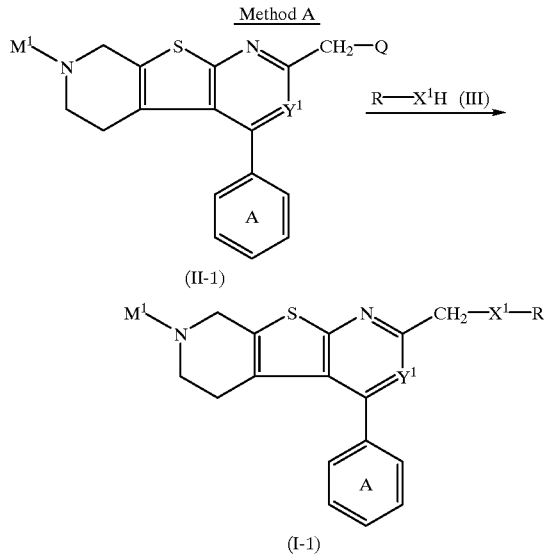

wherein, $M^1$ represents an optionally substituted acyl group, an optionally substituted carbamoyl group, an optionally substituted alkoxycarbonyl group, an optionally substituted sulfonyl group or an optionally substituted thiocarbamoyl group; Q represents a leaving group; $y^1$ represents $C-G^1$ ($G^1$ represents an esterified carboxyl group); $X^1$ represents an oxygen atom or a sulfur atom; the other symbols are as defined above.

In the above formula (II-1), the leaving group represented by Q includes, for example, halogens, preferably chlorine, bromine and iodine, and hydroxy groups activated by esterification, for example, residues of organic sulfonic acids (e.g., p-toluenesulfonyloxy group or methanesulfonyloxy group) or residues of organic phosphoric acids such as diphenylphosphoryloxy group, dibenzylphosphoryloxy group and dimethylphosphoryloxy group. The esterified carboxyl group represented by $G^1$ is, for example, the same groups as those exemplified above with respect to the esterified carboxyl group represented by G. The optionally substituted acyl group, the optionally substituted carbamoyl group, the optionally substituted alkoxycarbonyl group, the optionally substituted sulfonyl group or the optionally substituted thiocarbamoyl group represented by $M^1$ are, for example, the same groups as those exemplified above with respect to the optionally substituted acyl, the optionally substituted carbamoyl group, the optionally substituted alkoxycarbonyl group, the optionally substituted sulfonyl group or the optionally substituted thiocarbamoyl group represented by M, respectively.

In this method, the compound (II-1) is reacted with compound (III) in the presence of a base to obtain the compound (I-1). The reaction of the compounds (II-1) and (III) is carried out in an appropriate solvent. Examples of the solvent are aromatic hydrocarbons such as benzene, toluene and xylene, ethers such as dioxane, tetrahydrofuran and dimethoxyethane, alcohols such as methanol, ethanol and propanol, ethyl acetate, acetonitrile, pyridine, N,N-dimethylformamide (DMF), dimethyl sulfoxide (DMSO), chloroform, dichloromethane, 1,2-dichloroethane, 1,1,2,2-tetrachloroethane, acetone, 2-butanone and mixtures thereof. The reaction of the compounds (II-1) and (III) is carried out in the presence of an appropriate base selected from the group consisting of alkali metal salts such as sodium hydroxide, potassium hydroxide, potassium carbonate, sodium carbonate and sodium hydrogen carbonate, silver carbonate ($Ag_2CO_3$), sodium hydride, potassium hydride, pyridine, and amines such as triethylamine, N,N-dimethylaniline, 1,5-diazabicyclo[4.3.0]non-5-ene, 1,4-diazabicyclo[2.2.2]octane and 1,8-diazabicyclo[5.4.0]undec-7-ene. The amount of the base used is preferably about 1 to 5 mol equivalents per mol equivalent of the compound (II-1). This reaction is normally carried out at −20 to 150° C., preferably about −10 to 100° C.

The thienopyridine derivatives (I-1) thus obtained may be isolated and purified by known means for separation and purification such as concentration, concentration under reduced pressure, solvent extraction, crystallization, recrystallization, redissolution and chromatography.

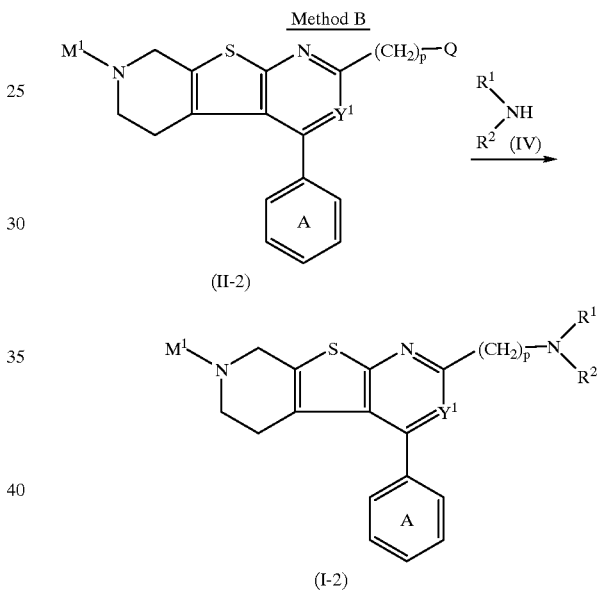

wherein p represents an integer from 1 to 6; and the other symbols are as defined above.

In this method, the compound (II-2) is reacted with the compound (IV) in the presence of a base to obtain the compound (I-2). The reaction of the compounds (II-2) and (IV) is carried out in an appropriate solvent. Examples of the solvent include aromatic hydrocarbons such as benzene, toluene and xylene, ethers such as dioxane, tetrahydrofuran and dimethoxyethane, alcohols such as methanol, ethanol and propanol, ethyl acetate, acetonitrile, pyridine, N,N-dimethylformamide (DMF), dimethyl sulfoxide (DMSO), chloroform, dichloromethane, 1,2-dichloroethane, 1,1,2,2-tetrachloroethane, acetone, 2-butanone and mixtures thereof. The reaction of the compounds (II-2) and (IV) is carried out in the presence of an appropriate base selected from the group consisting of alkali metal salts such as sodium hydroxide, potassium hydroxide, potassium carbonate, sodium carbonate and sodium hydrogen carbonate, pyridine, amines such as triethylamine and N,N-dimethylaniline, sodium hydride and potassium hydride. The amount of the base used is preferably about 1 to 5 mol equivalents per mol equivalent of the compound (II-2). This reaction is normally carried out at −20 to 150° C., preferably about −10 to 100° C. This reaction can also be carried out using the compound (IV) in excess as a base.

The thienopyridine derivatives (I-2) thus obtained may be isolated and purified by known means for separation and purification such as concentration, concentration under reduced pressure, solvent extraction, crystallization, recrystallization, redissolution and chromatography.

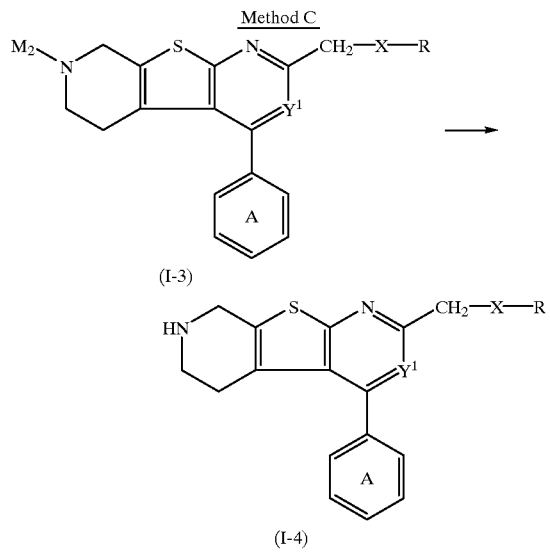

wherein $M^2$ represents an optionally substituted acyl group or an optionally substituted alkoxycarbonyl group; and the other symbols are as defined above.

In the above formula (I-3), the optionally substituted acyl group or the optionally substituted alkoxycarbonyl group represented by $M^2$ is, for example, the same acyl groups or the alkoxycarbonyl groups as those exemplified above with respect to M.

In this method, the compound (I-3) is subjected to hydrolysis in the presence of an acid to obtain the compound (I-4). The hydrolysis of the compound (I-3) is carried out in a hydrated or anhydrous solvent. Examples of the solvent include ethers such as dioxane, tetrahydrofuran and dimethoxyethane, alcohols such as methanol, ethanol, propanol, butanol and 2-methoxyethanol, acetonitrile, N,N-dimethylformamide (DMF), dimethyl sulfoxide (DMSO), acetone, 2-butanone, acetic acid and mixtures thereof. The acid is, for example, hydrochloric acid, sulfuric acid, nitric acid or hydrobromic acid. The amount of the acid used is preferably in excess, specifically about 5 to 50 mol equivalents per mol equivalent of the compound (I-3). This reaction is normally carried out at 30 to 150° C., preferably about 50 to 120° C. The reaction time is normally 1 to 100 hours.

This reaction can also be carried out in an aqueous or anhydrous solvent in the presence of a base. For examples, a preferred solvent includes a mixed solvent of water and an ether such as dioxane, tetrahydrofuran, dimethoxyethane or the like or an alcohol such as methanol, ethanol, propanol, butanol, 2-methoxyethanol or the like. The base used includes, for example, sodium hydroxide, potassium hydroxide, barium hydroxide, lithium hydroxide and the like. The amount of the base used is normally in excess, preferably about 5 to 50 mol equivalents per mol equivalent of the compound (I-3). This reaction is normally carried out at 30 to 150° C., preferably about 50 to 120° C. The reaction time is normally 1 to 100 hours.

The thienopyridine derivatives (I-4) thus obtained may be isolated and purified by known means for separation and purification such as concentration, concentration under reduced pressure, solvent extraction, crystallization, recrystallization, redissolution and chromatography.

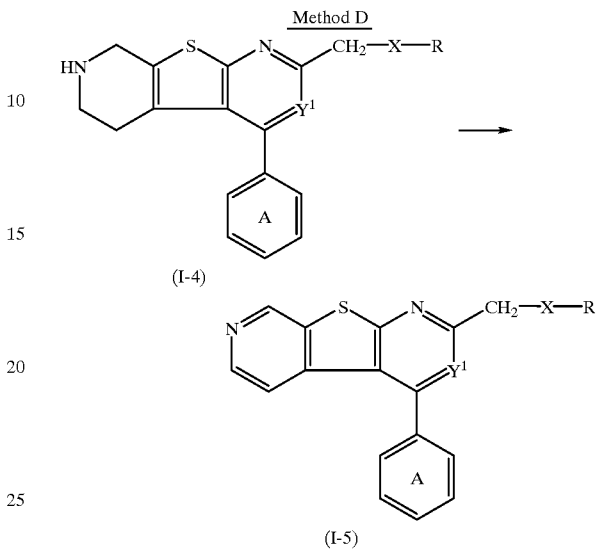

wherein the symbols are as defined above.

In this method, the compound (I-4) is subjected to oxidation reaction to obtain the compound (I-5). This reaction is carried out in the presence of an oxidizing agent in an appropriate solvent. The solvent includes, for example, aromatic hydrocarbons such as benzene, toluene and xylene, ethers such as dioxane, tetrahydrofuran and dimethoxyethane, ethylacetate, chloroform, dichloromethane, 1,2-dichloroethane, 1,1,2,2-tetrachloroethane and mixtures thereof. The oxidizing agent includes, for example, manganese dioxide and nitric acid. The amount of the oxidizing agent used is preferably in excess, specifically about 5 to 50 mol equivalents per mol equivalent of the compound (I-4). This reaction is normally carried out at 30 to 150° C., preferably about 50 to 120° C. The reaction time is normally 1 to 100 hours.

The thienopyridine derivatives (I-5) thus obtained may be isolated and purified by known means for separation and purification such as concentration, concentration under reduced pressure, solvent extraction, crystallization, recrystallization, redissolution and chromatography.

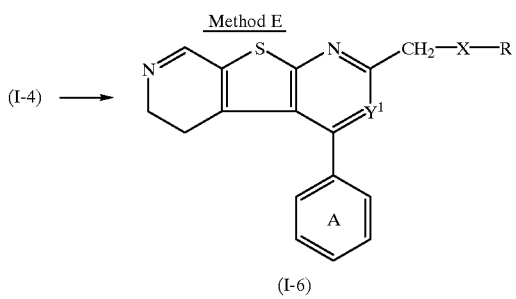

wherein the symbols are as defined above.

In this method, the compound (I-4) is subjected to the same oxidation reaction as in the above method D to obtain the compound (I-6). This reaction is carried out in the same manner as described in the above method D.

The thienopyridine derivatives (I-6) thus obtained may be isolated and purified by known means for separation and purification such as concentration, concentration under reduced pressure, solvent extraction, crystallization, recrystallization, redissolution and chromatography.

Method F

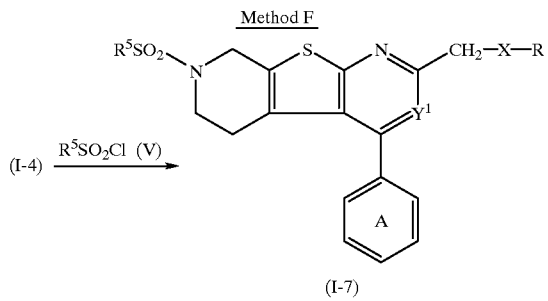

wherein $R^5$ represents an optionally substituted hydrocarbon residue or an optionally substituted heterocyclic group; and the other symbols are as defined above.

In the above formula (V), the optionally substituted hydrocarbon residue or the optionally substituted heterocyclic group represented by $R^5$ include the same groups as those exemplified above with respect to the optionally substituted hydrocarbon residue or the optionally substituted heterocyclic group represented by $R^1$.

In this method, the compound (I-4) is reacted with the compound (V) in the presence of a base to obtain the compound (I-7). The reaction of the compounds (I-4) and (V) is carried out in an appropriate solvent. Examples of the solvent includes aromatic hydrocarbons such as benzene, toluene and xylene, ethers such as dioxane, tetrahydrofuran and dimethoxyethane, ethyl acetate, acetonitrile, pyridine, N,N-dimethylformamide (DMF), dimethyl sulfoxide (DMSO), chloroform, dichloromethane, 1,2-dichloroethane, 1,1,2,2-tetrachloroethane, acetone, 2-butanone and mixtures thereof. The reaction of the compounds (I-4) and (V) is carried out in the presence of an appropriate base selected from the group consisting of alkali metal salts such as sodium hydroxide, potassium hydroxide, potassium carbonate, sodium carbonate and sodium hydrogen carbonate, silver carbonate (Ag$_2$CO$_3$), sodium hydride, potassium hydride, pyridine, and amines such as triethylamine, N,N-dimethylaniline, 1,5-diazabicyclo[4.3.0]non-5-ene, 1,4-diazabicyclo[2.2.2]octane and 1,8-diazabicyclo[5.4.0]undec-7-ene. The amount of the base used is preferably about 1 to 5 mol equivalents per mol equivalent of compound (I-4). This reaction is normally carried out at −20 to 150° C., preferably about −10 to 100° C.

The thienopyridine derivatives (I-7) thus obtained may be isolated and purified by known means for separation and purification such as concentration, concentration under reduced pressure, solvent extraction, crystallization, recrystallization, redissolution and chromatography.

Method G

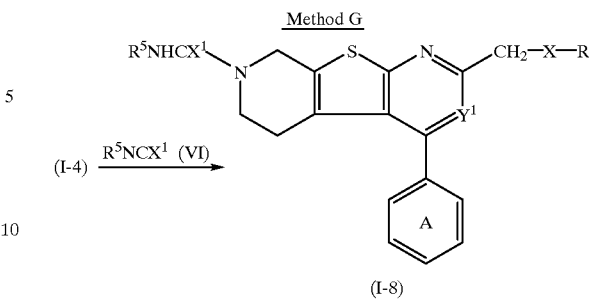

wherein the symbols are as defined above.

In this method, the compounds (I-4) and (VI) are reacted to obtain the compound (I-8). The reaction of the compounds (I-4) and (VI) is carried out in an appropriate solvent. The solvent includes, for example, aromatic hydrocarbons such as benzene, toluene and xylene, ethers such as dioxane, tetrahydrofuran and dimethoxyethane, ethyl acetate, acetonitrile, pyridine, N,N-dimethylformamide (DMF), dimethyl sulfoxide (DMSO), chloroform, dichloromethane, 1,2-dichloroethane, 1,1,2,2-tetrachloroethane, acetone, 2-butanone and mixtures thereof. The amount of the compound (VI) used is preferably about 1 to 5 mol equivalents per mol equivalent of the compound (I-4). This reaction is normally carried out at −50 to 150° C., preferably about −20 to 100° C.

The thienopyridine derivatives (I-8) thus obtained may be isolated and purified by known means for separation and purification such as concentration, concentration under reduced pressure, solvent extraction, crystallization, recrystallization, redissolution and chromatography.

Method H

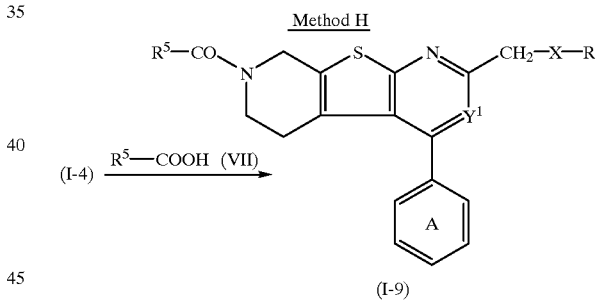

wherein the symbols are as defined above.

In this method, the compound (VII), its reactive derivative at the carboxyl group or its salt is reacted with the compound (I-4) to obtain the compound (I-9). The preferred reactive derivative at the carboxyl group of the compound (VII) includes acid halides, acid anhydrides, activated amides and activated esters. Examples of the preferred reactive derivatives include acid chlorides; acid azides; mixed acid anhydrides such as those with a substituted phosphoric acid such as dialkylphosphoric acid, phenylphosphoric acid, diphenylphosphoric acid, dibenzylphosphoric acid or halogenated phosphoric acid, or with dialkylphosphorous acid, sulfurous acid, thiosulfuric acid or sulfuric acid, or with a sulfonic acid such as methanesulfonic acid, or with an aliphatic carboxylic acid, such as acetic acid, propionic acid, butyric acid, isobutyropivalic acid, pentanoic acid, isopentanoic acid or trichloroacetic acid, or with an aromatic carboxylic acid such as benzoic acid; symmetric acid anhydrides; activated amides with imidazole, 4-substituted imidazole, dimethylpyrazole, triazole or tetrazole; activated esters such as cyanomethyl ester, methoxymethyl ester, dimethyliminomethyl ester, vinyl ester, propargyl ester, p-nitrophenyl ester, trichlorophenyl ester, pentachlorophenyl ester, mesylphenyl. ester, phenylazophenyl ester, phenylthio ester, p-nitrophenyl ester, p-cresylthio ester, carboxymethylthio ester, pyranyl ester, pyridyl ester, piperidyl ester and 8-quinolylthio ester; and esters with N-hydroxy compounds such as N,N-dimethylhydroxylamine, 1-hydroxy-2-(1H)-pyridone, N-hydroxysuccinimide, N-hydroxyphthalimide and 1-hydroxy-1H-benzotriazole. These reactive derivatives can be appropriately chosen according to a particular kind of the compound (VII) used. The preferred salts of the reactive derivatives of the compound (VII) include salts with bases, for example, alkali metal salts such as sodium salt and potassium salt, alkaline earth metal salts such as calcium salt and magnesium salt, ammonium salt, and organic base salts such as trimethylamine salt, triethylamine salt, pyridine salt, picoline salt, dicyclohexylamine salt and N,N-dibenzylethylenediamine salt. This reaction is normally carried out in a commonly used solvent such as water, an alcohol such as methanol or ethanol, acetone, dioxane, acetonitrile, chloroform, methylene chloride, ethylene chloride, tetrahydrofuran, ethyl acetate, N,N-dimethylformamide or pyridine, but can be carried out in any other organic solvent in so far as it does not interfere with the reaction. These commonly used solvents may be used as a mixture with water. When the compound (VIII) is used in the form of its free acid or salt, this reaction is preferably carried out in the presence of a commonly used condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide; N,N'-carbonylbis(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride; diphenylphosphorylazide; thionyl chloride; oxalyl chloride; a lower alkyl haloformate such as ethyl chloroformate or isopropyl chloroformate; triphenylphosphine; 2-ethyl-7-hydroxybenzisoxazolium salt; 2-ethyl-5-(m-sulfophenyl)isoxazolium hydroxide intramolecular salt; N-hydroxybenzotriazole; 1-(p-chlorobenzenesulfonyloxy)-6-chloro-1H-benzotriazole; or so-called Wilsmeier's reagent as prepared by reaction of N,N'-dimethylformamide and thionyl chloride, phosgene, trichloromethyl chloroformate, phosphorus oxychloride or the like. This reaction may also be carried out in the presence of an inorganic or organic base such as alkali metal hydrogen carbonate, tri(lower)alkylamine, pyridine, N-(lower)alkylmorpholine or N,N-di(lower)alkylbenzylamine. Although the reaction temperature is not specifically limited, this reaction is normally carried out under cooling to warming conditions. The N-alkoxycarbonyl compound can be produced according to the same manner as described in the above method H and is carried out by reaction with ClCOOR³ (R³ is as defined above).

The thienopyridine (I-9) thus obtained may be isolated and purified by known means for separation and purification such as concentration, concentration under reduced pressure, solvent extraction, crystallization, recrystallization, redissolution and chromatography.

The starting compound for the production of the compound (I) can, for example, be produced as follows:

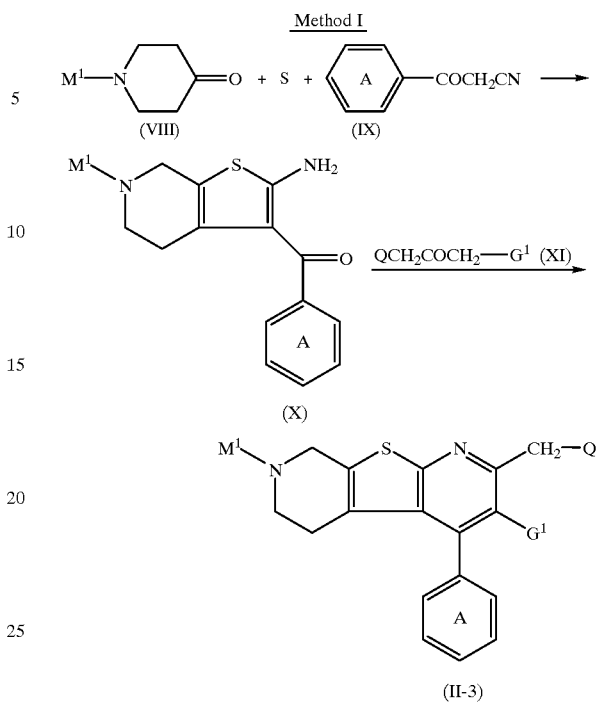

wherein the symbols are as defined above.

The compound (X) is produced by reacting the compounds (VIII) with (IX) and sulfur in a solvent in the presence of a base by the method described in the Journal of Medicinal Chemistry, Vol. 17, p. 624 (1974). The solvent includes, for example, aromatic hydrocarbons such as benzene, toluene and xylene, ethers such as dioxane, tetrahydrofuran and dimethoxyethane, alcohols such as methanol, ethanol and propanol, chloroform, dichloromethane, 1,2-dichloroethane, 1,1,2,2-tetrachloroethane and mixtures thereof. This reaction is carried out in the presence of an appropriate base selected from amines such as triethylamine, diethylaniline, morpholine, piperidine and N,N-dimethylaniline. The amount of the base used is preferably about 1 to 5 mol equivalents per mol equivalent of the compound (VIII). This reaction is normally carried out at −20 to 150° C., preferably about −10 to 100° C. The compounds (X) and (XI) are then reacted to obtain the compound (II-3). The reaction of the compounds (X) and (XI) is carried out in a solvent in the presence of an appropriate acid such as a Lewis acid such as aluminum chloride or zinc chloride, hydrochloric acid, sulfuric acid, trifluoroacetic acid or p-toluenesulfonic acid. The solvent includes, for example, aromatic hydrocarbons such as benzene, toluene and xylene, ethers such as tetrahydrofuran, dioxane and dimethoxyethane, alcohols such as methanol, ethanol and propanol, ethyl acetate, N,N-dimethylformamide (DMF), dimethyl sulfoxide (DMSO), chloroform, dichloromethane, 1,2-dichloroethane, 1,1,2,2-tetrachloroethane and mixtures thereof. The amount of the compound (XI) used is preferably about 1.0 to 2.0 mol equivalents per mol equivalent of the compound (X). The amount of the acid used is preferably about 0.05 to 2.0 mol equivalents per mol equivalent of the compound (X). This reaction is normally carried out at 0 to 200° C., preferably about 20 to 120° C. The reaction time is normally 0.5 to 20 hours, preferably 1 to 10 hours.

The thienopyridine derivative (II-3) thus obtained may be isolated and purified by known means for separation and purification such as concentration, concentration under reduced pressure, solvent extraction, crystallization, recrystallization, redissolution and chromatography.

The above methods A to I provide the production methods of thieno[2,3-b:5,4-c']dipyridine derivatives having the ring B containing a nitrogen atom. These methods can generally be applied to the production of the compounds wherein the ring B is 5-, 6- or 7-membered ring.

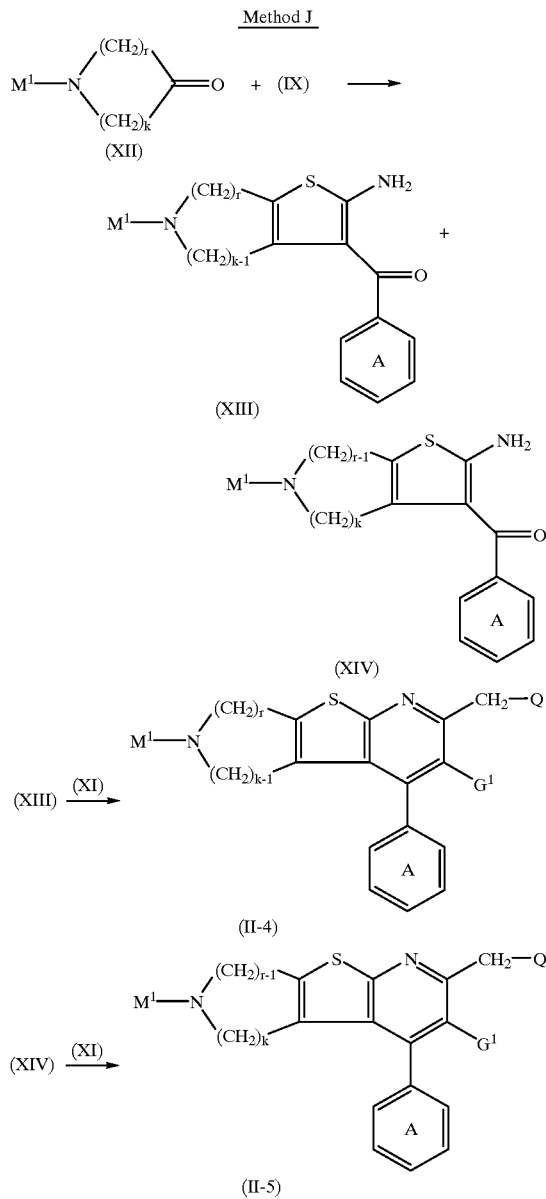

wherein k and r are the same or different and are 1, 2 or 3; and the other symbols are as defined above.

This method is carried out according to the same manner as described in the above method I. In the reaction of the compounds (XII) and (IX), a mixture of the compounds (XIII) and (XIV) is formed. After isolation and purification of the respective compounds (XIII) and (XIV), they are reacted with the compound (XI) to obtain the compounds (II-4) and (II-5), respectively.

The compounds (II-4) and (II-5) produced by this method are used for the reaction with the compound (III) according to the above method A, for the reaction with the compound (IV) according to the above method B, or for removal of the acyl group or alkoxycarbonyl group according to the above method C. Moreover, by using the product resulted from this removal reaction of the acyl group or alkoxycarbonyl group, the compounds having the saturated ring B can be produced according to the above method D; the N-sulfonyl derivative can be produced by a reaction with the compound (V) according to the above method F; the N-carbamoyl or N-thiocarbamoyl compounds can be produced by a reaction with the compound (VI) according to the above method G; and the N-acyl compound can be produced by reaction with the compound (V) according to the above method H.

When the thienopyridine derivatives produced by the methods A to J have isopropoxy group as the substituent of the ring A, the isopropoxy group can be converted into hydroxy group by treatment with titanium tetrachloride. This reaction can be carried out in a solvent such as chloroform, dichloromethane, carbon tetrachloride or the like at −50 to 30° C., preferably −10 to 20° C.

According to another aspect of the present invention, there is provided a compound represented by the formula (I'); or a salt thereof.

In the compound of the formula (I'), examples of X, q and R and the rings A and B include the same symbols and rings as those exemplified above with respect to the compound of the formula (I).

The halogen atom represented by G' includes, for example, chlorine, bromine, iodine or fluorine, preferably chlorine.

The optionally substituted hydrocarbon residue represented by M' includes, for example, the same hydrocarbon residues as those exemplified above with respect to $R^1$ or $R^2$ of the compound of the formula (I), preferably, methyl, ethyl, isopropyl, propyl, butyl, benzyl, phenethyl and 2-, 3- and 4-pyridylmethyl.

The optionally substituted acyl group represented by M' includes, for example, the same acyl groups as those exemplified above with respect to the substituents for the hydrocarbon residue, acyl group, sulfonyl group and heterocyclic group represented by $R^1$ or $R^2$ of the compound of the formula (I), preferably, acetyl and benzoyl.

The optionally substituted carbamoyl group represented by M' includes, for example, that represented by $R^1NHCO$ ($R^1$ is as defined above) as exemplified above with respect to the compound of the formula (I).

The optionally substituted thiocarbamoyl group represented by M' includes, for example, that represented by $R^1NHCS$ ($R^1$ is as defined above) as exemplified above with respect to the compound of the formula (I).

The optionally substituted sulfonyl group represented by M' includes, for example, that represented by $R^1SO_2$ ($R^1$ is as defined above) as exemplified above with respect to the compound of the formula (I).

Among the compounds of the above formula (I'), those wherein n is 1, M' is a hydrogen atom or benzyl; the ring B is a 6-membered ring containing a nitrogen atom, G' is a chlorine atom, —X—R— is 2-oxo-1-pyrrolidinylmethyl, 2-oxo-1-piperidinylmethyl, 2-oxohexamethyleneiminomethyl, N,N-diethylamino, 1,2,4-triazol-1-yl or 1-methylimidazol-2-ylthio, and the ring A is substituted by two methoxy group at the 3- and 4-positions thereof are particularly preferred.

Specific examples of the compound of the formula (I') are:
7-benzyl-3-chloro-4-(3,4-dimethoxyphenyl)-2-(2-oxo-1-piperidinylmethyl)-5,6,7,8-tetrahydrothieno[2,3-b:5,4-c']dipyridine,
7-benzyl-3-chloro-4-(3,4-dimethoxyphenyl)-2-(2-oxohexamethyleneiminomethyl)-5,6,7,8-tetrahydrothieno[2,3-b:5,4-c']dipyridine, 7-benzyl-3-chloro-4-(3,4-dimethoxyphenyl)-2-(2-oxo-1-pyrrolidinylmethyl)-5,6,7,8-tetrahydrothieno[2,3-b:5,4-c']dipyridine, and 7-benzyl-3-chloro-4-(4-hydroxy-3-methoxyphenyl)-2-(2-oxo-1-pyrrolidinylmethyl)-5,6,7,8-tetrahydrothieno[2,3-b:5,4-c']dipyridine.

The salt of the compound of the formula (I') of the present invention is preferably a pharmaceutically acceptable salt and examples thereof include those exemplified above with respect to the compound of the formula (I).

The compound of the above formula (I') can, for example, be produced as follows:

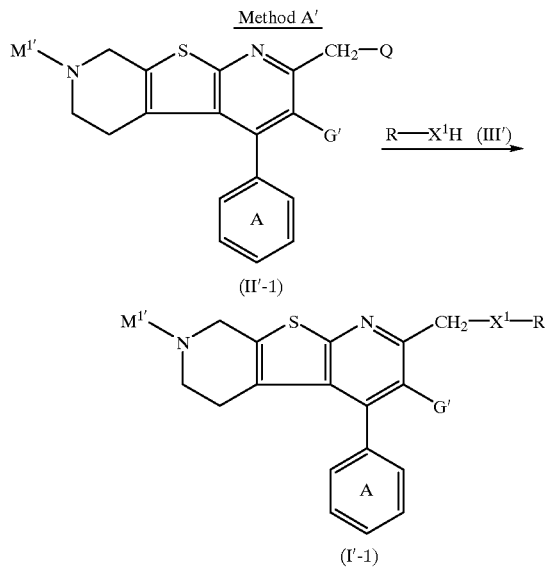

(II'-1)

(I'-1)

wherein $M^{1'}$ represents an optionally substituted hydrocarbon residue, an optionally substituted acyl group, an optionally substituted alkyl group, an optionally substituted carbamoyl group or an optionally substituted thiocarbamoyl group; Q represents a leaving group; $X^1$ represents an oxygen atom or a sulfur atom; and the other symbols are as defined above.

In the above formula (II'-1), the leaving group represented by Q include, for example, halogens, preferably chlorine, bromine and iodine, and hydroxyl groups activated by esterification, for example, organic sulfonic acid residues (e.g., p-toluenesulfonyloxy group, methanesulfonyloxy group) and residues of organic phosphoric acid such as diphenylphosphoryloxy groups, dibenzylphosphoryloxy groups and dimethylphosphoryloxy groups; the optionally substituted hydrocarbon residue, the optionally substituted acyl group the optionally substituted alkyl group, the optionally substituted carbamoyl group or the optionally substituted thiocarbamoyl group each represented by $M^{1'}$ included the same groups as those exemplified above with respect to the optionally substituted hydrocarbon residue, the optionally substituted acyl group, the optionally substituted alkyl group, the optionally substituted carbamoyl group or the optionally substituted thiocarbamoyl group represented by M', respectively.

In this method, the compound (II'-1) is reacted with the compound (III') in the presence of a base to yield compound (I'-1). The reaction of the compounds (II'-1) and (III') is carried out in an appropriate solvent. The solvent is, for example, aromatic hydrocarbons such as benzene, toluene and xylene, ethers such as dioxane, tetrahydrofuran and dimethoxyethane, alcohols such as methanol, ethanol and propanol, ethyl acetate, acetonitrile, pyridine, N,N-dimethylformamide (DMF), dimethyl sulfoxide (DMSO), chloroform, dichloromethane, 1,2-dichloroethane, 1,1,2,2-tetrachloroethane, acetone, 2-butanone and mixtures thereof. The reaction of the compounds (II'-1) and (III') is carried out in the presence of an appropriate base selected from the group consisting of alkali metal salts such as sodium hydroxide, potassium hydroxide, potassium carbonate, sodium carbonate and sodium hydrogen carbonate, silver carbonate ($Ag_2CO_3$), sodium hydride, potassium hydride, pyridine, and amines such as triethylamine, N,N-dimethylaniline, 1,5-diazabicyclo[4.3.0]non-5-ene, 1,4-diazabicyclo[2.2.2]octane and 1,8-diazabicyclo[5.4.0]undec-7-ene. The amount of the base used is preferably about 1 to 5 mol equivalents per mol equivalent of the compound (II'-1). This reaction is normally carried out at -20 to 150° C., preferably about -10 to 100° C.

The thienopyridine derivative (I'-1) thus obtained may be isolated and purified by known means for separation and purification such as concentration, concentration under reduced pressure, solvent extraction, crystallization, recrystallization, redissolution and chromatography.

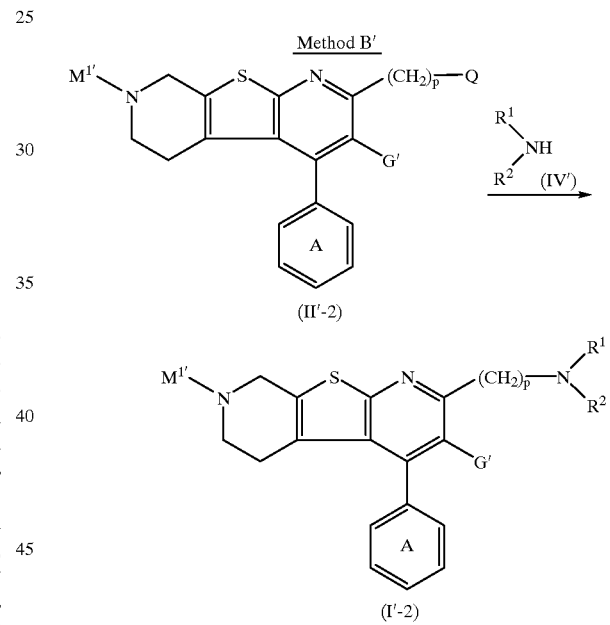

(II'-2)

(I'-2)

wherein p represents an integer from 1 to 6; and the other symbols are as defined above.

In this method, the compound (II'-2) is reacted with the compound (IV') in the presence of a base to yield the compound (I'-2). The reaction of compounds (II'-2) and (IV') is carried out in an appropriate solvent. The solvent is, for example, aromatic hydrocarbons such as benzene, toluene and xylene, ethers such as dioxane, tetrahydrofuran and dimethoxyethane, alcohols such as methanol, ethanol and propanol, ethyl acetate, acetonitrile, pyridine, N,N-dimethylformamide (DMF), dimethyl sulfoxide (DMSO), chloroform, dichloromethane, 1,2-dichloroethane, 1,1,2,2-tetrachloroethane, acetone, 2-butanone and mixtures thereof. The reaction of the compounds (II'-2) and (IV') is carried out in the presence of an appropriate base selected from the group consisting of alkali metal salts such as sodium hydroxide, potassium hydroxide, potassium carbonate, sodium carbonate and sodium hydrogen carbonate, pyridine, amines such as triethylamine and N,N-dimethylaniline, sodium hydride and potassium hydride. The amount of base used is preferably about 1 to 5 mol equivalents per mol equivalent of the compound (II'-2). This reaction is normally carried out at −20 to 150° C., preferably about −10 to 100° C. This reaction can also be carried out using the compound (IV') in excess as a base.

The thienopyridine derivative (I'-2) thus obtained may be isolated and purified by known means for separation and purification such as concentration, concentration under reduced pressure, solvent extraction, crystallization, recrystallization, redissolution and chromatography.

Method C'

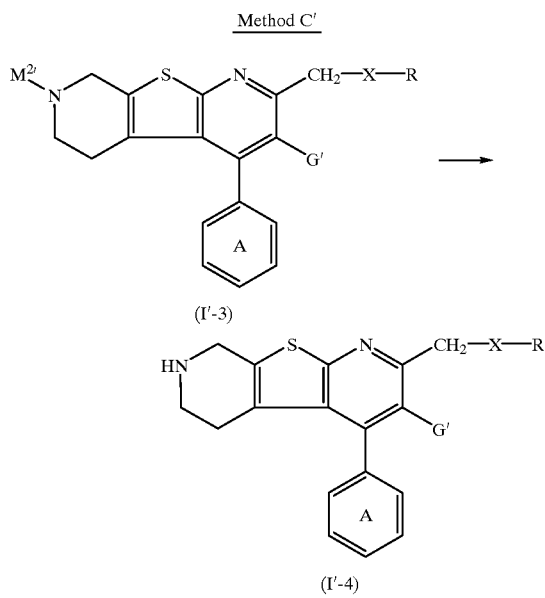

wherein $M^{2'}$ represents an optionally substituted acyl group; and the other symbols are as defined above.

In the formula (I'-3), the optionally substituted acyl group represented by $M^{2'}$ is, for example, the same acyl groups as those exemplified with respect to the optionally substituted acyl group represented by M'.

In this method, the compound (I'-3) is subjected to hydrolysis in the presence of an acid to yield the compound (I'-4). The hydrolysis of the compound (I'-3) is carried out in a hydrated solvent. The solvent is, for example, ethers such as dioxane, tetrahydrofuran and dimethoxyethane, alcohols such as methanol, ethanol, propanol, butanol and 2-methoxyethanol, acetonitrile, N,N-dimethylformamide (DMF), dimethyl sulfoxide (DMSO), acetone, 2-butanone, acetic acid and mixtures thereof. The acid is, for example, hydrochloric acid, sulfuric acid, nitric acid and hydrobromic acid. The amount of the acid used is preferably in excess, specifically about 5 to 50 mol equivalents per mol equivalent of the compound (I'-3). This reaction is normally carried out at 30 to 150° C., preferably about 50 to 120° C. The reaction time is normally 1 to 100 hours.

The thienopyridine derivative (I'-4) thus obtained may be isolated and purified by known means for separation and purification such as concentration, concentration under reduced pressure, solvent extraction, crystallization, recrystallization, redissolution and chromatography.

Method D'

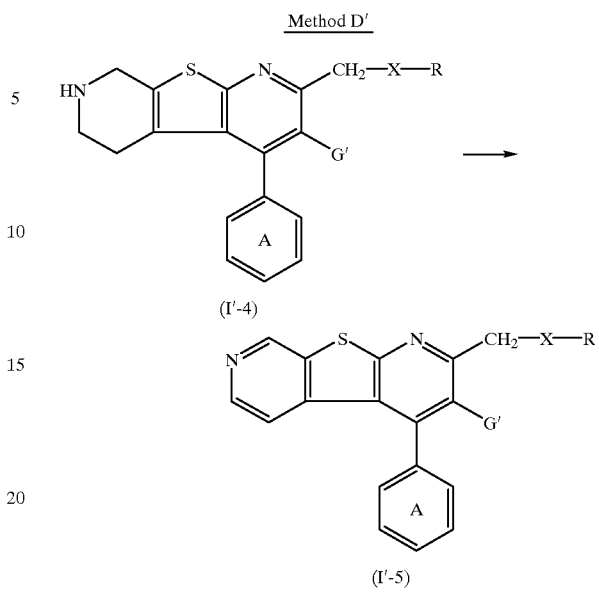

wherein the symbols are as defined above.

In this method, the compound (I'-4) is subjected to oxidation reaction to yield the compound (I'-5). This reaction is carried out in the presence of an oxidizing agent in an appropriate solvent. The solvent is, for example, aromatic hydrocarbons such as benzene, toluene and xylene, ethers such as dioxane, tetrahydrofuran and dimethoxyethane, ethylacetate, chloroform, dichloromethane, 1,2-dichloroethane, 1,1,2,2-tetrachloroethane and mixtures thereof. The oxidizing agent is, for example, manganese dioxide and nitric acid. The amount of the oxidizing agent used is preferably in excess, specifically about 5 to 50 mol equivalents per mol equivalent of the compound (I'-4). This reaction is normally carried out at 30 to 150° C., preferably about 50 to 120° C. The reaction time is normally 1 to 100 hours.

The thienopyridine derivative (I'-5) thus obtained may be isolated and purified by known means for separation and purification such as concentration, concentration under reduced pressure, solvent extraction, crystallization, recrystallization, redissolution and chromatography.

Method E'

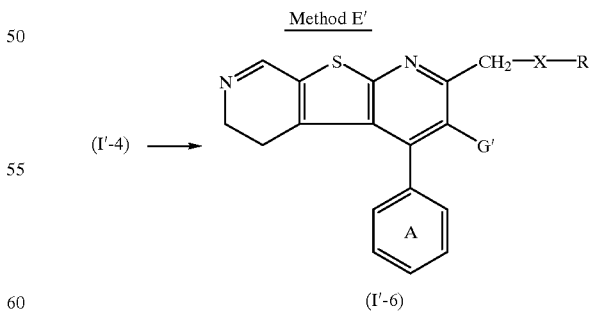

wherein the symbols are as defined above.

In this method, the compound (I'-4) is subjected to the same oxidation reaction as in method D' to yield the compound (I'-6). This reaction is carried out in the same manner as method D'.

The thienopyridine derivative (I'-6) thus obtained may be isolated and purified by known means of separation and purification such as concentration, concentration under reduced pressure, solvent extraction, crystallization, recrystallization, redissolution and chromatography.

Method F'

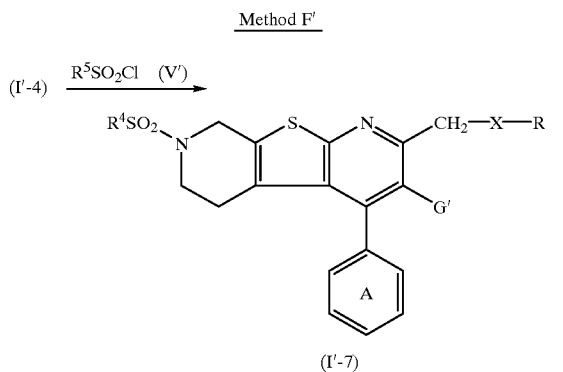

(I'-7)

wherein $R^5$ represents an optionally substituted hydrocarbon residue or an optionally substituted heterocyclic group and the other symbols are as defined above.

In the formula (V'), the optionally substituted hydrocarbon residue or the optionally substituted heterocyclic group represented by $R^5$ is, for example, the same groups as those exemplified above with respect to the optionally substituted hydrocarbon residue or the optionally substituted heterocyclic group represented by $R^1$.

In this method, the compound (I'-4) is reacted with the compound (V') in the presence of a base to yield the compound (I'-7). The reaction of compounds (I'-4) and (V') is carried out in an appropriate solvent. The solvent is, for example, aromatic hydrocarbons such as benzene, toluene and xylene, ethers such as dioxane, tetrahydrofuran and dimethoxyethane, ethyl acetate, acetonitrile, pyridine, N,N-dimethylformamide (DMF), dimethyl sulfoxide (DMSO), chloroform, dichloromethane, 1,2-dichloroethane, 1,1,2,2-tetrachloroethane, acetone, 2-butanone and mixtures thereof. The reaction of the compounds (I'-4) and (V') is carried out in the presence of an appropriate base selected from the group consisting of alkali metal salts such as sodium hydroxide, potassium hydroxide, potassium carbonate, sodium carbonate and sodium hydrogen carbonate, silver carbonate ($Ag_2CO_3$), sodium hydride, potassium hydride, pyridine, and amines such as triethylamine, N,N-dimethylaniline, 1,5-diazabicyclo[4.3.0] non-5-ene, 1,4-diazabicyclo[2.2.2]octane and 1,8-diazabicyclo[5.4.0]undec-7-ene. The amount of base used is preferably about 1 to 5 mol equivalents per mol equivalent of the compound (I'-4). This reaction is normally carried out at −20 to 150° C., preferably about −10 to 100° C.

The thienopyridine derivative (I'-7) thus obtained may be isolated and purified by known means for separation and purification such as concentration, concentration under reduced pressure, solvent extraction, crystallization, recrystallization, redissolution and chromatography.

Method G'

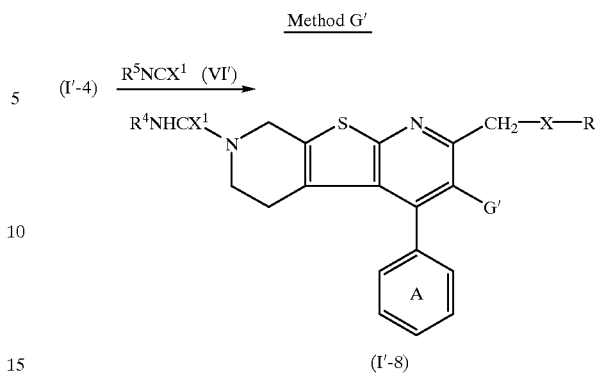

(I'-8)

wherein the symbols are as defined above.

In this method, the compounds (I'-4) and (VI') are reacted to yield the compound (I'-8). The reaction of the compounds (I'-4) and (VI') is carried out in an appropriate solvent. The solvent is, for example, aromatic hydrocarbons such as benzene, toluene and xylene, ethers such as dioxane, tetrahydrofuran and dimethoxyethane, ethyl acetate, acetonitrile, pyridine, N,N-dimethylformamide (DMF), dimethyl sulfoxide (DMSO), chloroform, dichloromethane, 1,2-dichloroethane, 1,1,2,2-tetrachloroethane, acetone, 2-butanone and mixtures thereof. The amount of the compound (VI') used is preferably about 1 to 5 mol equivalents per mol equivalent of the compound (I'-4). This reaction is normally carried out at −50 to 150° C., preferably about −20 to 100° C.

The thienopyridine derivative (I'-8) thus obtained may be isolated and purified by known means for separation and purification such as concentration, concentration under reduced pressure, solvent extraction, crystallization, recrystallization, redissolution and chromatography.

Method H'

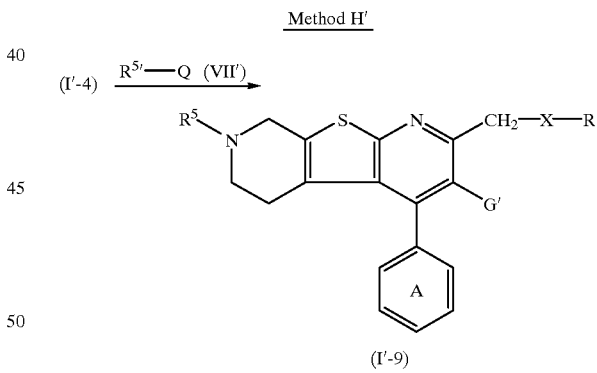

(I'-9)

wherein $R^{5'}$ represents an optionally substituted hydrocarbon residue; the other symbols have the same definitions as those shown above.

In formulas (I'-9) and (VII'), the optionally substituted hydrocarbon residue represented by $R^5$ is, for example, the same groups as those exemplified above with respect to the optionally substituted hydrocarbon residue represented by M'.

In this method, the compound (I'-4) is reacted with the compound (VII') in the presence of a base to yield the compound (I'-9). The reaction of the compounds (I'-4) and (VII') is carried out in an appropriate solvent. The solvent is, for example, aromatic hydrocarbons such as benzene, toluene and xylene, ethers such as dioxane, tetrahydrofuran and dimethoxyethane, alcohols such as methanol, ethanol and propanol, ethyl acetate, acetonitrile, pyridine, N,N-dimethylformamide (DMF), dimethyl sulfoxide (DMSO), chloroform, dichloromethane, 1,2-dichloroethane, 1,1,2,2-tetrachloroethane, acetone, 2-butanone and mixtures thereof. The reaction of the compounds (I'-4) and (VII') is carried out in the presence of an appropriate base selected from the group consisting of alkali metal salts such as sodium hydroxide, potassium hydroxide, potassium carbonate, sodium carbonate and sodium hydrogen carbonate, silver carbonate ($Ag_2CO_3$), sodium hydride, potassium hydride, pyridine, and amines such as triethylamine, N,N-dimethylaniline, 1,5-diazabicyclo[4.3.0]non-5-ene, 1,4-diazabicyclo[2.2.2]octane and 1,8-diazabicyclo[5.4.0]undec-7-ene. The amount of the base used is preferably about 1 to 5 mol equivalents per mol equivalent of the compound (I'-4). This reaction is normally carried out at −20 to 150° C., preferably about −10 to 100° C.

The thienopyridine derivative (I'-9) thus obtained may be isolated and purified by known means for separation and purification such as concentration, concentration under reduced pressure, solvent extraction, crystallization, recrystallization, redissolution and chromatography.

Method I'

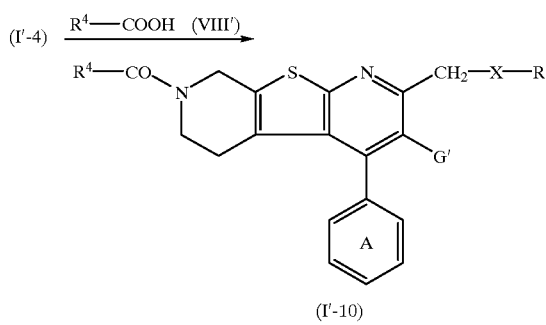

(I'-10)

wherein the symbols are as defined above.

In this method, the compound (VIII'), its reactive derivative at the carboxyl group thereof or a salt thereof is reacted with the compound (I'-4) to yield the compound (I'-10). Preferred reactive derivatives at the carboxyl group of the compound (VIII') include acid halides, acid anhydrides, activated amides and activated esters. Preferred examples thereof are acid chlorides; acid azides; mixed acid anhydrides such as those with a substituted phosphoric acid such as dialkylphosphoric acid, phenylphosphoric acid, diphenylphosphoric acid, dibenzylphosphoric acid or halogenated phosphoric acid, or with dialkylphosphorous acid, sulfurous acid, thiosulfuric acid or sulfuric acid, or with a sulfonic acid such as methanesulfonic acid, or with an aliphatic carboxylic acid, such as acetic acid, propionic acid, butyric acid, isobutyropivalic acid, pivalic acid, pentanoic acid, isopentanoic acid or trichloroacetic acid, or with an aromatic carboxylic acid such as benzoic acid; symmetric acid anhydrides; activated amides with imidazole, 4-substitutional imidazole, dimethylpyrazole, triazole or tetrazole; activated esters such as cyanomethyl ester, methoxymethyl ester, dimethyliminomethyl ester, vinyl ester, propargyl ester, p-nitrophenyl ester, trichlorophenyl ester, pentachlorophenyl ester, mesylphenyl ester, phenylazophenyl ester, phenylthio ester, p-nitrophenyl ester, p-cresylthio ester, carboxymethylthio ester, pyranyl ester, pyridyl ester, piperidyl ester and 8-quinolylthio ester; and esters with N-hydroxy compounds such as N,N-dimethylhydroxylamine, 1-hydroxy-2-(1H)-pyridone, N-hydroxysuccinimide, N-hydroxyphthalimide and 1-hydroxy-1H-benzotriazole. These reactive derivatives can be optionally chosen according to a particular kind of the compound (VIII') used. Preferred salts of the reactive derivatives of the compound (VIII') include salts with bases, for example, alkali metal salts such as sodium salt and potassium salt, alkaline earth metal salts such as calcium salt and magnesium salt, ammonium salt, and organic base salts such as trimethylamine salt, triethylamine salt, pyridine salt, picoline salt, dicyclohexylamine salt and N,N-dibenzylethylenediamine salt. This reaction is normally carried out in a commonly used solvent such as water, an alcohol such as methanol or ethanol, acetone, dioxane, acetonitrile, chloroform, methylene chloride, ethylene chloride, tetrahydrofuran, ethyl acetate, N,N-dimethylformamide or pyridine, but can be carried out in any other organic solvent in so far as it does not interfere with the reaction. These commonly used solvents may be used in mixture with water. When the compound (VIII') is used in the form of free acid or salt thereof, this reaction is preferably carried out in the presence of a commonly used condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide; N,N'-diisopropylcarbodiimide; N-ethyl-N'-(3-dimethylaminopropyl)carbodiimide; N,N'-carbonylbis(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride; diphenylphosphorylazide; thionyl chloride; oxalyl chloride; a lower alkyl haloformate such as ethyl chloroformate or isopropyl chloroformate; triphenylphosphine; 2-ethyl-7-hydroxybenzisoxaolium salt; 2-ethyl-5-(m-sulfophenyl)isoxazolium hydroxide intramolecular salt; N-hydroxybenzotriazole; 1-(p-chlorobenzenesulfonyloxy)-6-chloro-1H-benzotriazole; or so-called Wilsmeier's reagent as prepared by reaction of N,N'-dimethylformamide and thionyl chloride, phosgene, trichloromethyl chloroformate, phosphorus oxychloride or the like. This reaction may also be carried out in the presence of an inorganic or organic base such as alkali metal hydrogen carbonate, tri(lower)alkylamine, pyridine, N-(lower)alkylmorpholine or N,N-di(lower)alkylbenzylamine. Although the reaction temperature is not specifically limited, this reaction is normally carried out under cooling to warming conditions.

The thienopyridine derivative (I'-10) thus obtained may be isolated and purified by known means for separation and purification such as concentration, concentration under reduced pressure, solvent extraction, crystallization, recrystallization, redissolution and chromatography.

The starting compound for the production of the compound (I') can, for example, be produced as follows:

Method J'

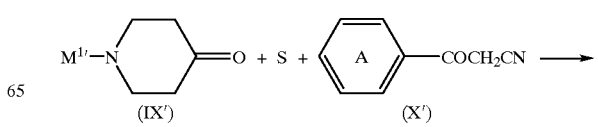

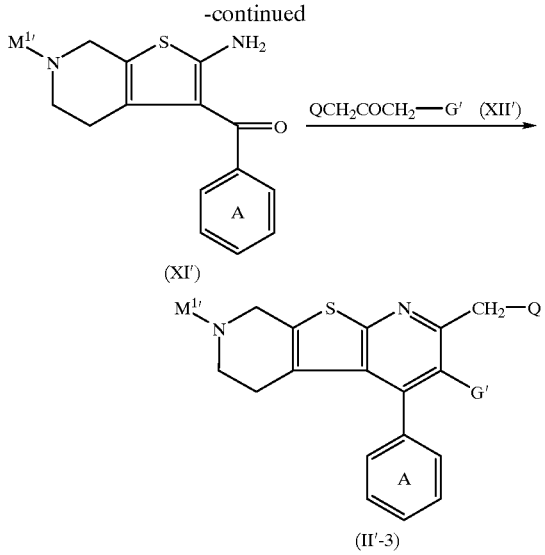

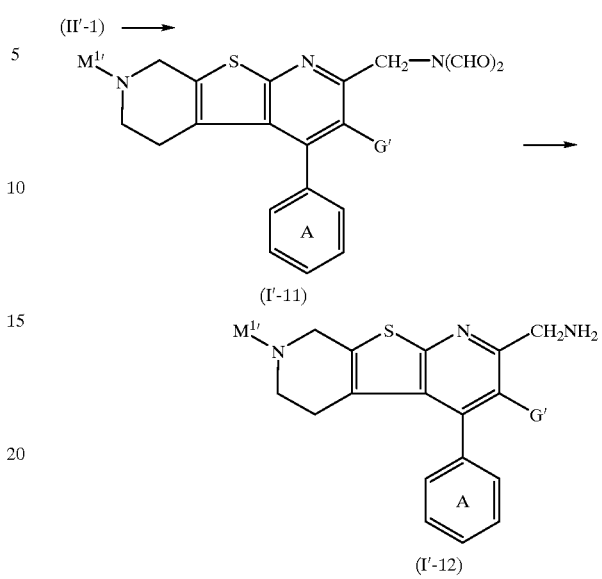

wherein the symbols are as defined above.

The compound (XI') is produced by reacting the compounds (IX') and (X') and sulfur in a solvent in the presence of a base by the method described in the Journal of Medicinal Chemistry, Vol. 17, p. 624 (1974). The solvent is, for example, aromatic hydrocarbons such as benzene, toluene and xylene, ethers such as dioxane, tetrahydrofuran and dimethoxyethane, alcohols such as methanol, ethanol and propanol, chloroform, dichloromethane, 1,2-dichloroethane, 1,1,2,2-tetrachloroethane and mixtures thereof. This reaction is carried out in the presence of an appropriate base selected from amines such as triethylamine, diethylaniline, morpholine, piperidine and N,N-dimethylaniline. The amount of base used is preferably about 1 to 5 mol equivalents per mol equivalent of the compound (IX'). This reaction is normally carried out at −20 to 150° C., preferably about −10 to 100° C. The compounds (XI') and (XII') are then reacted to yield the compound (II'-3). The reaction of the compounds (XI') and (XII') is carried out in a solvent in the presence of an appropriate acid such as a Lewis acid such as aluminum chloride or zinc chloride, hydrochloric acid, sulfuric acid, trifluoroacetic acid or p-toluenesulfonic acid. The solvent is, for example, aromatic hydrocarbons such as benzene, toluene and xylene, ethers such as tetrahydrofuran, dioxane and dimethoxyethane, alcohols such as methanol, ethanol and propanol, ethyl acetate, N,N-dimethylformamide (DMF), dimethyl sulfoxide (DMSO), chloroform, dichloromethane, 1,2-dichloroethane, 1,1,2,2-tetrachloroethane and mixtures thereof. The amount of the compound (XII') used is preferably about 1.0 to 2.0 mol equivalents per mol equivalent of the compound (XI'). The amount of the acid used is preferably about 0.05 to 2.0 mol equivalents per mol equivalent of the compound (XI'). This reaction is normally carried out at 0 to 200° C., preferably about 20 to 120° C. The reaction time is normally 0.5 to 20 hours, preferably 1 to 10 hours.

The thienopyridine derivative (II'-3) thus obtained may be isolated and purified by known means for separation and purification such as concentration, concentration under reduced pressure, solvent extraction, crystallization, recrystallization, redissolution and chromatography.

wherein the symbols are as defined above.

In this method, the compound (II'-1) is reacted with sodium salt of diformylimide to form the formylamino compound (I'-11) and then it is reacted with an acid to produce the amino compound (I'-12). The reaction of the compounds (II'-1) and sodium salt of diformylimide is carried out according to the same manner as the above method A'. The compound (I'-11) can be converted into the compound (I'-12) according to the same manner as the above method C'. From the resultant compound (I'-12), the sulfonylamino compound can be produced according to the above method F' and the acylamino compound can be produced according to the above method I'.

When the thienopyridine derivative produced by the above methods A' to K' has isopropoxy group as a substituent of the ring A, the isopropoxy group can be converted into hydroxyl group by treatment with titanium tetrachloride. This reaction can be carried out in a solvent such as chloroform, dichloromethane, carbon tetrachloride or the like at −50 to 30° C., preferably, −10 to 20° C.

The compound of the formula (A) of the present invention, that is, the compound of the formula (I) or (I'), can be administered orally or parenterally, as formulated with a pharmaceutically acceptable carrier, in the form of solid preparations such as tablets, capsules, granules and powders, or liquid preparations such as syrups and injectable preparations.

Pharmaceutically acceptable carriers include various organic or inorganic carrier substances commonly used as pharmaceutical materials including excipients, lubricants, binders and disintegrants for solid preparations, and solvents, dissolution aids, suspending agents, isotonizing agents, buffers and soothing agents for liquid preparations. Other pharmaceutical additives such as preservatives, antioxidants, coloring agents and sweetening agents may be used as necessary.

Preferred excipients include lactose, sucrose, D-mannitol, starch, crystalline cellulose and light silicic anhydride.

Preferred lubricants include magnesium stearate, calcium stearate, talc and colloidal silica.

Preferred binders include binding cellulose, sucrose, D-mannitol, dextrin, hydroxypropyl cellulose, hydroxypropylmethyl cellulose and polyvinylpyrrolidone.

Preferred disintegrants include starch, carboxymethyl cellulose, carboxymethyl cellulose calcium, croscarmellose sodium and carboxymethyl starch sodium.

Preferred solvents include water for injection, alcohol, propylene glycol, macrogol, sesame oil and corn oil.

Preferred dissolution aids include polyethylene glycol, propylene glycol, D-mannitol, benzyl benzoate, ethanol, tris-aminomethane, cholesterol, triethanolamine, sodium carbonate and sodium citrate.

Preferred suspending agents include surfactants such as stearyltriethanolamine, sodium lauryl sulfate, laurylaminopropionic acid, lecithin, benzalkonium chloride, benzethonium chloride and monostearic glycerol; and hydrophilic polymers such as polyvinyl alcohol, polyvinylpyrrolidone, carboxymethyl cellulose sodium, methyl cellulose, hydroxymethyl cellulose, hydroxyethyl cellulose and hydroxypropyl cellulose.

Preferred isotonizing agents include sodium chloride, glycerol and D-mannitol.

Preferred buffers include buffer solutions of phosphates, acetates, carbonates and citrates.

Preferred soothing agents include benzyl alcohol.

Preferred preservatives include p-oxybenzoic acid esters, chlorobutanol, benzyl alcohol, phenethyl alcohol, dehydroacetic acid and sorbic acid.

Preferred antioxidants include sulfites and ascorbic acid.

The compounds of the formula (I) or (I') or salts thereof as provided by the present invention exhibit anti-inflammatory activity and have been confirmed to have excellent anti-arthritic activity in an experimental model of adjuvant arthritis showing arthritic symptoms similar to those in human rheumatoid arthritis. In addition, the compounds of the present invention have excellent bone resorption inhibitory activity and are useful for preventing or treating born destruction accompanying arthritis, osteoporosis and the like. Further, the compounds of the present invention have an activity for inhibiting production of immunocytokines [e.g., interleukin-2 ((IL-2), interferon-γ (IFN-γ)] and are useful for preventing or treating immune-related diseases including autoimmune disease of humans and other mammals. Moreover, the compounds of the present invention are of low toxicity.

Therefore, the compounds of the present invention can be used for preventing and treating any arthritis showing inflammatory symptoms in the joint of mammals including humans (e.g., humans, horses, bovines, swines, dogs, cats), bone destruction and osteoporosis.

Examples of immune-related diseases include systemic lupus erythematosus, inflammatory bowel disease (idiopathic ulcerative colitis, Crohn's disease), multiple sclerosis, psoriasis, chronic hepatitis, bladder carcinoma, breast cancer, cancer of the uterine cervix, chronic lymphocytic leukemia, chronic mylogenous leukemia, carcinoma of the colon and rectum, colonic cancer, rectal cancer, *Helicobacter pylori* bacterial infectious disease, Hodgkin's disease, insulin dependent diabetes mellitus, malignant melanoma, multiple myeloma, non-Hodgkin's lymphoma, non-small cell lung cancer, ovarian cancer, peptic ulcer, prostatic cancer, septic shock, tuberculosis, sterility, arteriosclerosis, Behcet's disease, asthma, atopic dermatitis, nephritis, systemic fungal infection, acute bacterial meningitis, acute myocardial infarction, acute pancreatitis, acute viral encephalitis, adult respiratory distress syndrome, bacterial pneumonia, chronic pancreatitis, herpes simplex virus infection, varicellazoster viral infectious disease, AIDS, human papilloma viral infectious disease, influenza, invasive staphylococcal infectious disease, peripheral vessel disease, sepsis, interstitial hepatic disease, regional ileitis and multiple sclerosis. In particular, the compounds of the present invention can be used for preventing or treating systemic lupus erythematosus, chronic hepatitis, interstitial hepatic disease, asthma, psoriasis, idiopathic ulcerative colitis, Crohn's disease, regional ileitis or multiple sclerosis. The compounds of the present invention can be used for preventing rejection after organ transplantation.

Although the dose of the compound of the formula (I) or (I') used in the present invention varies according to particular route of administration and symptoms of the subject patient to be treated, it can be chosen over the range from 5 mg to 1,000 mg for oral administration or from 1 mg to 100 mg for parenteral administration as a daily dose for an adult person and this can be administered 1 to 3 times per day.

The following test examples illustrate the pharmacological activity of the compound of the formula (I) or (I') of the present invention or salts thereof.

TEST EXAMPLE 1A

Activity on Rat Adjuvant Arthritis

Male Lewis rats (7 weeks old, Clea Japan) were sensitized by intracutaneous injection of 0.05 ml of Freund's complete adjuvant (0.5% dead tubercle bacillus cell suspension in liquid paraffin) at the right hind paw. The test drug (6.25 mg/kg), in a suspension in 0.5% methyl cellulose, was administered once daily for 14 days starting just before sensitization (day 0). At the days 0 and 14, the left hind paw volume and body weight of the animals were measured using a plethysmometer (manufactured by Ugo Basile Company, Italy) and an electronic balance (EB-3200D, manufactured by Shimadzu Corporation, Japan), respectively, and paw swelling suppression rate (%) and body weight gain rate (%), relative to non-sensitized rats, were determined.

The results, expressed in mean ± S.E. for each group (N=6), were compared and statistically analyzed by Dunnet method. Level of significance was set below 5%. As shown in Table 1, the compound of the present invention was effective in relieving systemic symptoms as assessed by paw edema suppression and body weight gain.

TABLE 1

| Compound (Ex. No.) | Edema inhibitory rate (%) | Body weight[1] gain rate (%) |
| --- | --- | --- |
| 1A | 49 | 15 |
| 7A | 84** | 26** |
| 15A | 60** | 9 |

[1] $\dfrac{\text{(Drug administered rats)} - \text{(Sensitized control rats)}}{\text{(Normal control rats)} - \text{(Sensitized control rats)}} \times 100$

**p < 0.01 vs control

TEST EXAMPLE 2A

Bone Resorption Inhibitory Activity

The measurement of bone resorption inhibitory activity was carried out according to the method of Raisz [J. Clin. Invest., 44, 103–116 (1965)]. Namely, 50 μCi of $^{45}$Ca (radioisotope of calcium in $CaCl_2$ solution) was subcutaneously injected into a Sprague-Dawley rat of 18th day of pregnancy. On the next day, the abdomen was opened and a fetal rat was taken out sterilely. The left and right humeri (radii and ulnae) were removed from the body under a dissection microscope and connective tissues and cartilages were removed as much as possible. Thus, bone culture samples were prepared. The bone was incubated in a medium (0.6 ml) of $BCJ_b$ medium (Fitton-Jackson modification: GIBCO Laboratories, U.S.A.) containing 2 mg/ml of bovine serum albumin at 37° C. for 24 hours in an atmosphere of 5% of $CO_2$ in air. The bones were cultured for an additional 2 days in the above medium containing a final concentration of 10 μM of the compound. The ratio (%) of $^{45}Ca$ released from the bone into the medium was calculated according to the following equation.

$$\text{The ratio of } ^{45}\text{Ca released from the bone into the medium (\%)} = \frac{^{45}\text{Ca counts in the medium}}{^{45}\text{Ca counts in the medium} + ^{45}\text{Ca counts in the bone}} \times 100$$

The bones from the same litter were cultured for 2 days the same manner without addition of the compound, and used as the control. The mean ± standard deviation of the values for five bones of each group was calculated. The ratio (%) of this value to the control value was calculated. The results are shown in Table 2 (In the tables hereinafter, Ex. No. indicates Example No.).

TABLE 2

| Compound (Ex. No.) | Bone resorption inhibitory activity ($^{45}$Ca release) (% based on the control value) |
| --- | --- |
| 2A | 62** |
| 5A | 72* |
| 12A | 77* |
| 27A | 74* |
| 28A | 67*** |
| 33A | 72** |

*; p < 0.05
**; p < 0.02
****; p < 0.01 vs control (Student's t-test)

TEST EXAMPLE 1B

Activity on Rat Adjuvant Arthritis

Male Lewis rats (7 weeks old, Clea Japan) were sensitized by intracutaneous injection of 0.05 ml of Freund's complete adjuvant (0.5% dead tubercle bacillus cell suspension in liquid paraffin) at the right hind paw. The test drug (6.25 mg/kg or 3.13 mg/kg), in a suspension in 0.5% methyl cellulose, was administered once daily for 14 days starting just before sensitization (day 0). At the days 0 and 14, the left hind paw volume and body weight of the animals were measured using a plethysmometer (manufactured by Ugo Basile Company, Italy) and an electronic balance (EB-3200D, manufactured by Shimadzu Corporation, Japan), respectively, and paw swelling suppression rate (%) and body weight gain rate (%), relative to non-sensitized rats, were determined.

The results, expressed in mean ± S.E. for each group (N=6), were compared and statistically analyzed by Dunnet method. Level of significance was set below 5%. As shown in Table 3, the compound of the present invention was effective in relieving systemic symptoms as assessed by paw edema suppression and body weight gain.

TABLE 3

| Compound (Ex. No.) | Dose (mg/kg) | Edema inhibitory rate (%) | Body weight[1] gain rate (%) |
| --- | --- | --- | --- |
| 28B | 6.25 | 78** | 19** |
| 29B | 3.13 | 69** | 12 |

[1] $\frac{\text{(Drug administered rats)} - \text{(Sensitized control rats)}}{\text{(Normal control rats)} - \text{(Sensitized control rats)}} \times 100$

**p < 0.01 vs control

TEST EXAMPLE 2B

Bone Resorption Inhibitory Activity

The measurement of bone resorption inhibitory activity was carried out according to the method of Raisz [J. Clin. Invest., 44, 103–116 (1965)]. Namely, 50 μCi of $^{45}Ca$ (radioisotope of calcium in $CaCl_2$ solution) was subcutaneously injected into a Sprague-Dawlay rat of 18th day of pregnancy. On the next day, the abdomen was opened and a fetal rat was taken out sterilely. The left and right humeri (radii and ulnae) were removed from the body under a dissection microscope and connective tissues and cartilages were removed as much as possible. Thus, bone culture samples were prepared. The bone was incubated in a medium (0.6 ml) of $BCJ_b$ medium (Fitton-Jackson modification: GIBCO Laboratories, U.S.A.) containing 2 mg/ml of bovine serum albumin at 37° C. for 24 hours in an atmosphere of 5% of $CO_2$ in air. The bones were cultured for an additional 2 days in the above medium containing a final concentration of 10 μM of the compound. The ratio (%) of $^{45}Ca$ released from the bone into the medium was calculated according to the following equation.

$$\text{The ratio of } ^{45}\text{Ca released from the bone into the medium (\%)} = \frac{^{45}\text{Ca counts in the medium}}{^{45}\text{Ca counts in the medium} + ^{45}\text{Ca counts in the bone}} \times 100$$

The bones from the same litter were cultured for 2 days the same manner without addition of the compound, and used as the control. The mean ± standard deviation of the values for five bones of each group was calculated. The ratio (%) of this value to the control value was calculated. The results are shown in Table 4 (In the tables hereinafter, Ex. No. indicates Example No.).

TABLE 4

| Compound (Ex. No.) | Bone resorption inhibitory inhibitory activity ($^{45}$Ca release) (% based on the control value) |
| --- | --- |
| 24B | 44** |
| 25B | 52** |
| 28B | 47** |

**; p < 0.01 vs control (Student's t-test)

The following reference examples and examples further illustrate the production of the compounds of the formulas (I) and (I') in detail, but are not to be construed to limit the scope of the present invention.

A. PRODUCTION OF THE COMPOUNDS OF FORMULA (I)

REFERENCE EXAMPLE 1A

A mixture of ω-cyano-3,4-dimethoxyacetophenone (10.54 g), sulfur (1.77 g), 1-(4-chlorobenzoyl)-4-piperidone (13.1 g), morpholine (4.67 ml) and ethanol (100 ml) was stirred under refluxing conditions for 2 hours. The reaction mixture was poured over ice-water; the separating crystal was collected by filtration and recrystallized from ethanol to yield 2-amino-6-(4-chlorobenzoyl)-3-(3,4-dimethoxybenzoyl)-4,5,6,7-tetrahydrothieno[2,3-c]pyridine (21.33 g, 91%) as light-yellow needle crystals having a melting point of 138 to 140° C.

REFERENCE EXAMPLES 2A and 3A

In the same manner as in Reference Example 1A, the compounds listed in Table 5 were obtained.

TABLE 5

| Ref. Ex. No. | A | Melting point (° C.) | Recrystallizing solvent |
|---|---|---|---|
| 2A | 3,4-dimethoxyphenyl (OCH₃, OCH₃) | 143–145 | Ethanol |
| 3A | 4-chlorophenyl (Cl) | 88–89 | Ethyl acetate-Hexane |

REFERENCE EXAMPLE 4A

A mixture of 2-amino-6-(4-chlorobenzoyl)-3-(3,4-dimethoxybenzoyl)-4,5,6,7-tetrahydrothieno[2,3-c]pyridine (20.55 g), ethyl 4-chloroacetoacetate (8.17 g), hydrochloric acid-ethanol (23%, 7.34 g) and ethanol (80 ml) was stirred under refluxing conditions for 2.5 hours. The separating crystal was collected by filtration and recrystallized from ethyl acetate to yield ethyl 7-(4-chlorobenzoyl)-2-chloromethyl-4-(3,4-dimethoxyphenyl)-5,6,7,8-tetrahydrothieno[2,3-b:5,4-c']dipyridine-3-carboxylate (for structural formula, see below) (12.38 g, 47%) as a light-yellow crystal having a melting point of 132 to 133° C.

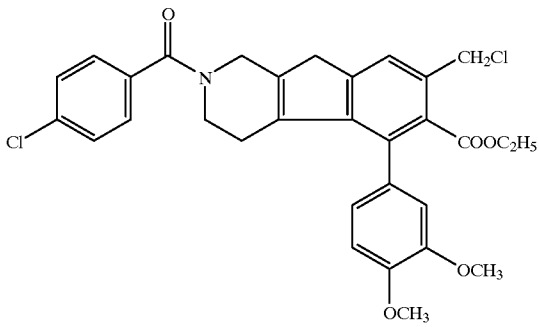

REFERENCE EXAMPLES 5A AND 6A

In the same manner as in Reference Example 4A, the compounds listed in Table 6 were obtained.

TABLE 6

| Ref. Ex. No. | A | Melting point (° C.) | Recrystallizing solvent |
|---|---|---|---|
| 5A | 3,4-dimethoxyphenyl (OCH₃, OCH₃) | 94–95[1) | Ethanol |
| 6A | 4-chlorophenyl (Cl) | 195–197 | Ethyl acetate-Hexane |

[1)]Amorphous solid. NMR (δ ppm in CDCl₃): 1.02 (3H, t, J = 6.8 Hz), 2.03–2.18 (2H, broad), 3.38–3.73 (2H, broad), 3.87 (3H, s), 3.95 (3H, s), 4.07 (2H, q, J = 6.8 Hz), 4.65–5.10 (2H, broad), 4.87 (2H, s), 6.81–6.94 (3H, m), 7.43 (5H, m).

REFERENCE EXAMPLE 7A

In the same manner as in Reference Example 1A, ω-cyano-3,4-dimethoxyacetophenone, 1-benzyloxycarbonyl-3-pyrrolidone and sulfur were reacted to yield 2-amino-5-benzyloxycarbonyl-3-(3,4-dimethoxybenzoyl)-4,6-dihydrothieno[2,3-c]pyrrole, which was then recrystallized from ethanol to yield a light-yellow prismatic crystal having a melting point of 195 to 196° C.

REFERENCE EXAMPLE 8A

A mixture of the compound (1.0 g) obtained in Reference Example 7A, ethyl 4-chloroacetoacetate (3.4 g), p-toluenesulfonic acid monohydrate (0.607 g) and benzene (300 ml) was heated under refluxing conditions for 5 hours while removing water produced, the reaction mixture was washed successively with water, an aqueous saturated solution of sodium bicarbonate and water, dried (MgSO$_4$), and concentrated under reduced pressure. The residue was subjected to silica gel column chromatography and eluted with ethyl acetate-hexane (1:1, v/v) to yield ethyl 2-benzyloxycarbonyl-6-chloromethyl-8-(3,4-dimethoxyphenyl)-2,3-dihydro-1H-pyrrolo[3',4':4,5]thieno[2,3-b]pyridine-7-carboxylate (having the following structure) (5.7 g, 63%), which was then recrystallized to yield colorless prismatic crystals having a melting point of 137 to 138° C.

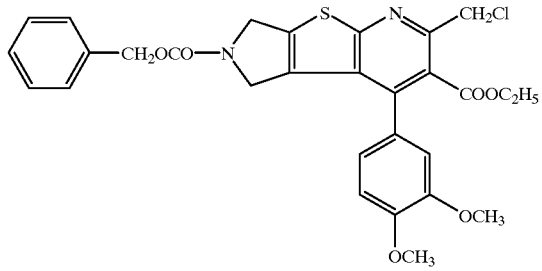

REFERENCE EXAMPLE 9A

In the same manner as in Reference Example 1A, ω-cyano-3,4-methylenedioxyacetophenone, 1-benzoyl-4-piperidone and sulfur were reacted to yield 2-amino-6-benzoyl-3-(3,4-methylenedioxybenzoyl)-4,5,6,7-tetrahydrothieno[2,3-c]pyridine, which was then recrystallized from chloroform-hexane to yield light-yellow prismatic crystals having a melting point of 211 to 212° C.

REFERENCE EXAMPLE 10A

In the same manner as in Reference Example 4A, the compound obtained in Reference Example 9A and ethyl 4-chloroacetoacetate were reacted to yield ethyl 7-benzoyl-2-chloromethyl-4-(3,4-methylenedioxyphenyl)-5,6,7,8-tetrahydrothieno[2,3-b:5,4-c']dipyridne-3-carboxylate, which was then recrystallized from ethyl acetate-hexane to yield colorless prismatic crystals having a melting point of 185 to 186° C.

REFERENCE EXAMPLES 11A–13A

In the same manner as in Reference Example 1A, the compounds listed in Table 7 were obtained.

TABLE 7

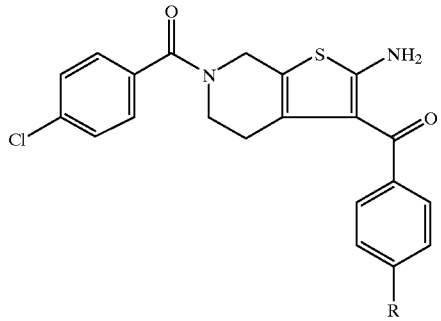

| Reference Example No. | R | Melting point (° C.) | Recrystallizing solvent |
|---|---|---|---|
| 11A | C$_2$H$_5$ | 70–72 | Ethyl acetate-Hexane |
| 12A | C$_3$H$_7$ | 85–87 | Ethyl acetate-Hexane |
| 13A | (CH$_3$)$_2$CH | 55–57 | Ethyl acetate-Hexane |

REFERENCE EXAMPLES 14A–16A

In the same manner as that in Reference Example 4A, the compounds listed in Table 8 were obtained.

TABLE 8

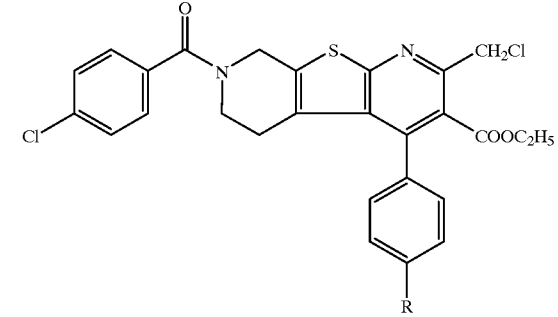

| Reference Example No. | R | Melting point (° C.) | Recrystallizing solvent |
|---|---|---|---|
| 14A | C$_2$H$_5$ | 205 | Ethyl acetate-Ethanol |
| 15A | C$_3$H$_7$ | 196–197 | Ethyl acetate-Hexane |
| 16A | (CH$_3$)$_2$CH | 209–210 | Ethyl acetate-Hexane |

REFERENCE EXAMPLE 17A

In the same manner as in Reference Example 1A, ω-cyano-4-isopropoxy-3-methoxyacetophenone, 1-(4-chlorobenzoyl)-4-piperidone and sulfur were reacted to yield 2-amino-6-(4-chlorobenzoyl)-3-(4-isopropoxy-3-methoxybenzoyl)-4,5,6,7-tetrahydrothieno[2,3-c]pyridine, which was recrystallized from ethyl acetate-hexane to yield light-yellow prismatic crystals having a melting point of 118 to 119° C.

REFERENCE EXAMPLE 18A

In the same manner as in Reference Example 4A, the compound obtained in Reference Example 17A and ethyl 4-chloroacetoacetate were reacted to yield ethyl 7-(4-chlorobenzoyl)-2-chloromethyl-4-(4-isopropoxy-3-methoxyphenyl)-4,5,6,7-tetrahydrothieno[2,3-b:5,4-c']dipyridne-3-carboxylate, which was then recrystallized from ethyl acetate to yield light-yellow needle crystals having a melting point of 135 to 136° C.

REFERENCE EXAMPLE 19A

A solution of ethyl 3,4-dimethoxybenzoate (17.8 g) and acetonitrile (7.0 g) in toluene (30 ml) was added dropwise to a suspension of oily sodium hydride (60%, 6.8 g) in toluene (170 ml) and N,N-dimethylformamide (DMF) (17 ml) at 100° C. After addition, the suspension was stirred at 100° C. for 3 hours, the reaction mixture was poured over ice-water and the organic layer was separated. The aqueous layer was acidified with 2N hydrochloric acid and extracted with ethyl acetate. The ethyl acetate layer was washed with water, dried (MgSO$_4$) and dried under reduced pressure to yield ω-cyano-3,4-dimethoxyacetophenone (1.4 g, 80%), which was then recrystallized from ethyl acetate to yield colorless needle crystals having a melting point of 141 to 142° C.

REFERENCE EXAMPLES 20A–25A

In the same manner as in Reference Example 19A, the compounds listed in Table 9 were obtained.

TABLE 9

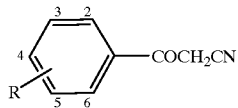

| Reference Example No. | R | Melting point (° C.) | Recrystallizing solvent |
|---|---|---|---|
| 20A | 4-C$_2$H$_5$ | —[1] | Ethyl acetate-Hexane |
| 21A | C$_3$H$_7$ | —[2] | Ethyl acetate-Hexane |
| 22A | (CH$_3$)$_2$CH | —[3] | Ethyl acetate-Hexane |
| 23A | 3-CH$_3$O, 4-(CH$_3$)$_2$CHO | 114–115 | Ethyl acetate-Hexane |
| 24A | 4-Cl | —[4] | Ethyl acetate-Hexane |
| 25A | 3,4-OCH$_2$O | 135–136 | Ethyl acetate-Hexane |

[1]NMR (δ ppm in CDCl$_3$): 1.25(3H, t, J=7.0Hz), 2.70(2H, q, J=7.0Hz), 4.08(2H, s), 7.33(2H, d, J=8.0Hz), 7.84(2H, d, J=8.0Hz)
[2]NMR(δ ppm in CDCl$_3$): 0.95(3H, t, J=7.4Hz), 1.67(2H, m), 2.67(2H, q, J=7.4Hz), 4.07(2H, s), 7.32(2H, d, J=8.2Hz), 7.84(2H, d, J=8.2Hz)
[3]NMR(δ ppm in CDCl$_3$): 1.28(6H, d, J=7.0Hz), 2.99(1H, m), 4.08(2H, s), 7.37(2H, d, J=8.6Hz), 7.86(2H, d, J=8.6Hz)
[4]NMR(δ ppm in CDCl$_3$): 4.06(2H, s), 7.51(2H, d, J=8.8Hz), 7.87(2H, d, J=8.8Hz)

REFERENCE EXAMPLE 26A

A mixture of 1-benzyloxycarbonyl-3-piperidone (9.1 g), ω-cyano-3,4-dimethoxyacetophenone (8.0 g), sulfur (1.3 g), morpholine (3.6 ml) and ethanol (150 ml) was heated under refluxing conditions for 3 hours. The reaction mixture was concentrated under reduced pressure, to the residue was added ethyl acetate, the insoluble was filtered off, and the filtrate was washed with water, dried (MgSO$_4$) and concentrated under reduced pressure. The residue was subjected to silica gel column chromatography and eluted with ethyl acetate-hexane (2:3, v/v) to yield 2-amino-7-benzyloxycarbonyl-3-(3,4-dimethoxybenzoyl)-4,5,6,7-tetrahydrothieno[2,3-b]pyridine (2.76 g, 16%) as light-yellow prismatic crystals having a melting point of 177 to 178° C.

REFERENCE EXAMPLE 27A

From the fraction subsequently eluted in the column chromatography of Reference Example 26A, 2-amino-5-benzyloxycarbonyl-3-(3,4-dimethoxybenzoyl)-4,5,6,7-tetrahy-drothieno[3,2-c]pyridine (6.50 g, 37%) as a light-yellow powder.

NMR (δ ppm in CDCl$_3$): 2.6–2.7 (2H, m), 3.72 (2H, t, J=5.8 Hz), 3.8–4.1 (8H, m), 5.07 (2H, s), 6.2–6.4 (1H, m), 6.7–7.5 (9H, m).

REFERENCE EXAMPLE 28A

In the same manner as in Reference Example 26A, ω-cyano-3,4-dimethoxyacetophenone, 1-(4-chlorobenzoyl)-3-piperidone and sulfur were reacted to yield 2-amino-5-(4-chlorobenzoyl)-3-(3,4-dimethoxybenzoyl)-4,5,6,7-tetrahydro-thieno[3,2-c]pyridine as powder.

NMR (δ ppm in CDCl$_3$): 2.6–2.8 (2H, m), 3.4–4.0 (4H, m), 3.93 (6H, s), 6.2–7.5 (9H, m)

REFERENCE EXAMPLE 29A

In the same manner as in Reference Example 4A, the compound obtained in Reference Example 28A and ethyl 4-chloroacetoacetate were reacted to yield ethyl 6-(4-chlorobenzoyl)-2-chloromethyl-4-(3,4-dimethoxyphenyl)-5,6,7,8-tetrahydrothieno[2,3-b:4,5-c']dipyridine-3-carboxylate as powder. NMR (δ ppm in CDCl$_3$): 0.98 (3H, t, J=7.2 Hz), 2.9–3.2 (2H, m), 3.6–4.2 (6H, m), 3.98 (6H, s), 4.85 (2H, s), 6.5–7.5 (7H, m)

REFERENCE EXAMPLE 30A

In the same manner as in Reference Example 4A, the compound obtained in Reference Example 26A and ethyl 4-chloroacetoacetate were reacted to yield ethyl 8-benzyloxycarbonyl-2-chloromethyl-4-(3,4-dimethoxyphenyl)-6,7,8-tetrahydrothieno[2,3-b:5,4-b']dipyridine-3-carboxylate, which was recrystallized from ethyl acetate-hexane to yield colorless prismatic crystals having a melting point of 178 to 179° C.

REFERENCE EXAMPLE 31A

In the same manner as in Reference Example 4A, the compound obtained in Reference Example 27A and ethyl 4-chloroacetoacetate were reacted to yield ethyl 6-benzyloxycarbonyl-2-chloromethyl-4-(3,4-dimethoxyphenyl)-5,6,7,8-tetrahydrothieno[2,3-b:4,5-c']dipyridine-3-carboxylate, which was then recrystallized from ethyl acetate-hexane to yield colorless prismatic crystals having a melting point of 125 to 126° C.

EXAMPLE 1A

A mixture of the compound obtained in Reference Example 5A (0.80 g), diethylamine (0.64 g) and dichloromethane (25 ml) was stirred under refluxing conditions for 4 hours. The reaction mixture was washed with water and dried (MgSO$_4$), after which the solvent was distilled off. The residue was subjected to silica gel column chromatography and eluted with ethyl acetate-hexane (2:1, v/v) to yield ethyl 7-benzoyl-2-(N,N-diethylaminomethyl)-4-(3,4-dimethoxyphenyl)-5,6,7,8-tetrahydrothieno[2,3-b:5,4-c'] dipyridine-3-carboxylate (for structural formula, see below) (0.60 g, 70%) as amorphous solid having a melting point of 86 to 87° C.

NMR (δ ppm in CDCl3): 0.93 (3H, t, J=7.2 Hz), 0.95 (6H, t, J=7.0 Hz), 1.95–2.16 (2H, broad), 2.00–2.18 (2H, m), 2.54 (4H, q, J=7.0 Hz), 3.36–3.70 (2H, broad), 3.86 (3H, s), 3.91 (2H, s), 3.93 (2H, q, J=7.2 Hz), 4.62–4.73 (1H, broad), 4.73–5.16 (1H, broad), 6.81–6.92 (3H, m), 7.43 (5H, s).

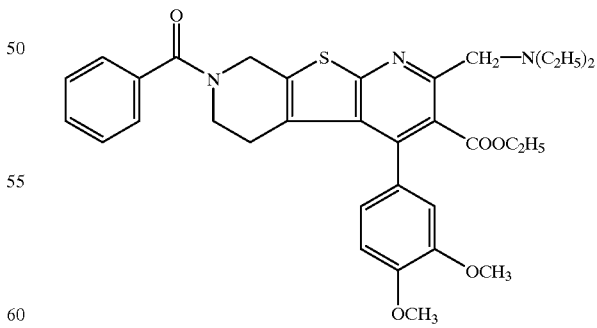

EXAMPLE 2A

The compound obtained in Reference Example 4A was subjected to the same reaction as that in Example 1A to yield ethyl 7-(4-chlorobenzoyl)-2-(N,N-diethylaminomethyl)-4-

(3,4-dimethoxyphenyl)-5,6,7,8-tetrahydrothieno[2,3-b:5,4-c']dipyridine-3-carboxylate (for structural formula, see below) as amorphous solid having a melting point of 96 to 98° C.

NMR (δ ppm in CDCl3): 0.93 (3H, t, J=7.4 Hz), 0.95 (6H, t, J=7.0 Hz), 2.09 (2H, broad), 2.54 (4H, q, J=7.0 Hz), 3.86 (3H, s), 3.94 (2H, q, J=7.0 Hz), 3.95 (3H, s), 4.73 (1H, s), 4.96 (1H, s), 6.81–6.93 (3H, s), 7.40 (4H, s).

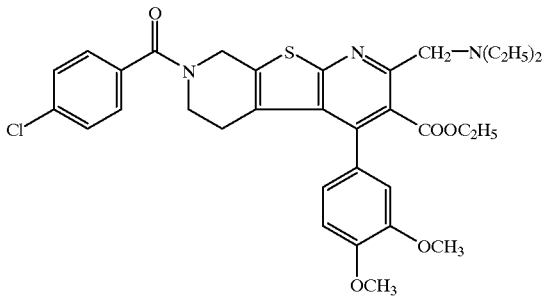

EXAMPLE 3A

A mixture of the compound obtained in Reference Example 4A (1.16 g), ethyl isonipecotate (0.40 g), potassium carbonate (0.50 g) and N,N-dimethylformamide (10 ml) was stirred at room temperature for 3 hours, after which it was poured over water and extracted with ethyl acetate. The ethyl acetate layer was washed with water and dried (MgSO4), after which the solvent was distilled off. The residue was subjected to silica gel column chromatography and eluted with ethyl acetate-hexane (1:1, v/v) to yield ethyl 7-(4-chlorobenzoyl)-4-(3,4-dimethoxyphenyl)-2-(4-ethoxycarbonylpiperidinomethyl)-5,6,7,8-tetrahydrothieno-[2,3-b:5,4-c']dipyridine-3-carboxylate (for structural formula, see below) (0.70 g, 50%) as an amorphous solid having a melting point of 99 to 101° C.

NMR (δ ppm in CDCl3): 0.95 (3H, t, J=7.2 Hz), 1.23 (3H, t, J=7.2 Hz), 1.50–1.90 (4H, m), 2.00–2.36 (5H, m), 2.75–2.88 (2H, m), 3.50 (2H, broad s), 3.84 (2H, s), 3.871 (3H, s), 3.95 (3H, s), 4.10 (2H, q, J=7.2 Hz), 4.73 (1H, broad), 4.98 (1H, broad), 6.81–6.95 (3H, m), 7.33–7.44 (4H, m).

EXAMPLE 4A

A mixture of the compound obtained in Reference Example 6A (6.49 g), diethylamine (2.71 g) and tetrahydrofuran (50 ml) was stirred under refluxing conditions for 17 hours, after which the reaction mixture was poured over water and extracted with ethyl acetate. The ethyl acetate layer was washed with water and dried (MgSO4), after which the solvent was distilled off to yield ethyl 7-benzoyl-4-(4-chlorophenyl)-2-(N,N-diethylaminomethyl)-5,6,7,8-tetrahydrothieno[2,3-b:5,4-c']dipyridine-3-carboxylate (for structural formula, see below) (5.81 g, 84%), which was then recrystallized from ethyl acetate-hexane to yield a colorless needle crystal having a melting point of 177 to 178° C.

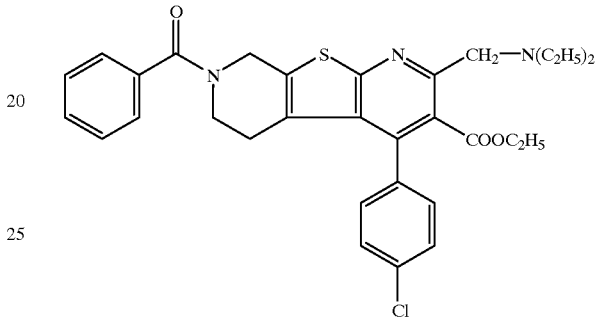

EXAMPLE 5A

A mixture of the compound obtained in Example 1A (4.02 g) and 3N HCl (12 ml) was stirred at 80° C. for 13.5 hours. After the reaction mixture was alkalinized with 1N NaOH, it was extracted with ethyl acetate. The ethyl acetate layer was washed with water and dried (MgSO4), after which the solvent was distilled off. The residue was subjected to silica gel column chromatography and eluted with chloroform-methanol (30:1, v/v) to yield ethyl 2-(N,N-diethylaminomethyl)-4-(3,4-dimethoxyphenyl)-5,6,7,8-tetrahydrothieno-[2,3-b:5,4-c']dipyridine-3-carboxylate (for structural formula, see below) (2.30 g, 70%) as an amorphous solid having a melting point of 72 to 75° C.

NMR (δ ppm in CDCl3): 0.94 (3H, t, J=7.6 Hz), 0.96 (3H, t, J=7.2 Hz), 1.95–2.15 (2H, m), 2.54 (4H, q, J=7.2 Hz), 2.91 (2H, t, J=5.8 Hz), 3.86 (3H, s), 3.92 (2H, s), 3.94 (3H, s), 3.95 (2H, q, J=7.6 Hz), 4.11 (2H, s), 6.82–6.87 (3H, m).

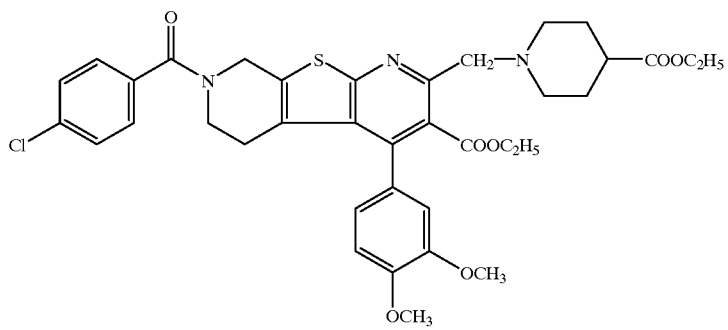

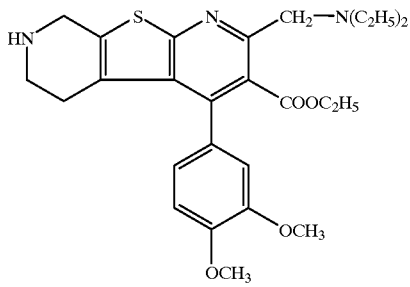

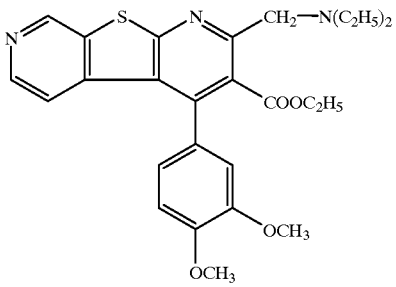

EXAMPLE 6A

A mixture of the compound obtained in Example 4A (2.09 g) and concentrated hydrochloric acid (8 ml)-water (16 ml) was stirred at 90° C. for 4 hours. After the reaction mixture was alkalinized with 1N NaOH, it was extracted with ethyl acetate. The ethyl acetate layer was washed with water and dried (MgSO$_4$), after which the solvent was distilled off. The residual solid was recrystallized from ethyl acetate-hexane to yield ethyl 4-(4-chlorophenyl)-2-(N,N-diethylaminomethyl)-5,6,7,8-tetrahydrothieno[2,3-b:5,4-c'] dipyridine-3-carboxylate (for structural formula, see below) (1.34 g, 79%) as colorless needle crystals having a melting point of 104 to 106° C.

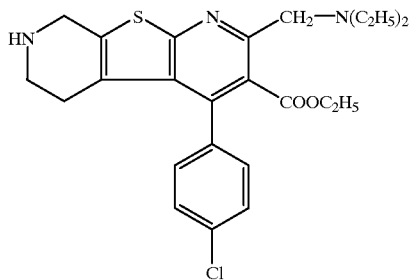

EXAMPLE 7A

A mixture of the compound obtained in Example 5A (10.16 g), activated manganese dioxide (30.93 g) and toluene (200 ml) was stirred under refluxing conditions for 11.5 hours. The reaction mixture was filtered; the filtrate was concentrated under reduced pressure. The residue was subjected to silica gel column chromatography and eluted with ethyl acetate-hexane-methanol (20:20:1, v/v) to yield ethyl 2-(N,N-diethylaminomethyl)-4-(3,4-dimethoxyphenyl) thieno[2,3-b:5,4-c']dipyridine-3-carboxylate (for structural formula, see below) (3.1 g, 31%), which was then recrystallized from ethyl acetate to yield colorless needle crystals having a melting point of 163 to 165° C.

EXAMPLE 8A

From the fraction subsequently eluted in the column chromatography of Example 7A, ethyl 2-(N,N-diethylaminom-ethyl)-4-(3,4-dimethoxyphenyl)-5,6-dihydrothieno[2,3-b:5,4-c']dipyridine-3-carboxylate (for structural formula, see below) (3.1 g, 31%) was obtained, which had a melting point of 118 to 120° C.

NMR (δ ppm in CDCl3): 0.95 (3H, t, J=7.2 Hz), 0.96 (6H, t, J=7.2 Hz), 2.08 (2H, t, J=8.0 Hz), 2.55 (4H, q, J=7.2 Hz), 3.63 (2H, dt, J=8.0 & 2.2 Hz), 3.87 (3H, s), 3.95 (2H, s), 3.96 (2H, q, J=7.2 Hz), 6.78–6.88 (2H, m), 6.93 (1H, d, J=8.0 Hz), 8.36 (1H, t, J=2.2 Hz).

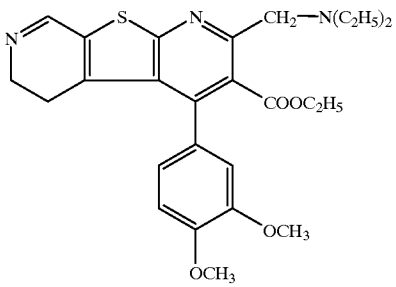

EXAMPLE 9A

A mixture of the compound obtained in Example 5A (0.96 g), benzenesulfonyl chloride (0.43 g), triethylamine (0.42 ml) and tetrahydrofuran (20 ml) was stirred at room temperature for 14 hours. The reaction mixture was poured over water and extracted with ethyl acetate. The ethyl acetate layer was washed with water and dried (MgSO$_4$), after which the solvent was distilled off. The residue was subjected to silica gel column chromatography and eluted with ethyl acetate-hexane-methanol (20:20:1, v/v) to yield ethyl 7-benzenesulfonyl-2-(N,N-diethylaminomethyl)-4-(3,4-dimethoxyphenyl)-5,6,7,8-tetrahydrothieno[2,3-b:5,4-c'] dipyridine-3-carboxylate (for structural formula, see below) (0.96 g, 76%), which was then recrystallized from ethyl acetate-hexane to yield colorless needle crystals having a melting point of 161 to 162° C.

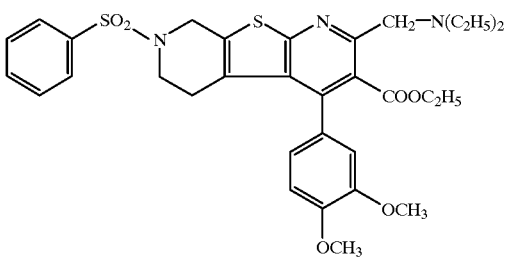

EXAMPLE 10A

In the same manner as in Example 9A, ethyl 2-(N,N-diethylaminomethyl)-4-(3,4-dimethoxyphenyl)-7-methanesulfonyl-5,6,7,8-tetrahydrothieno[2,3-b:5,4-c']dipyridine-3-carboxylate (for structural formula, see below) was obtained, which was then recrystallized from ethyl acetate-hexane to yield colorless needle crystals having a melting point of 147 to 148° C.

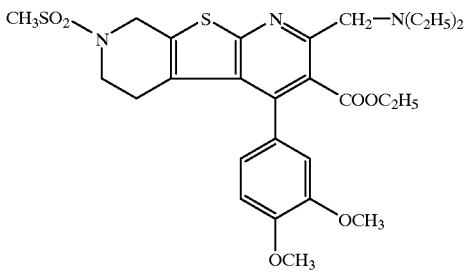

EXAMPLE 11A

A mixture of the compound obtained in Example 5A (1.0 g), phenyl isothiocyanate (0.31 g) and tetrahydrofuran (20 ml) was stirred at room temperature for 14 hours, after which it was concentrated under reduced pressure. The residue was subjected to silica gel column chromatography and eluted with ethyl acetate-hexane-methanol (20:20:1, v/v) to yield ethyl 2-(N,N-diethylaminomethyl)-4-(3,4-dimethoxyphenyl)-7-phenylthiocarbamoyl-5,6,7,8-tetrahydrothieno[2,3-b:5,4-c']dipyridine-3-carboxylate (for structural formula, see below) (1.03 g, 80%), which was then recrystallized from ethyl acetate-hexane to yield colorless crystals having a melting point of 104 to 106° C.

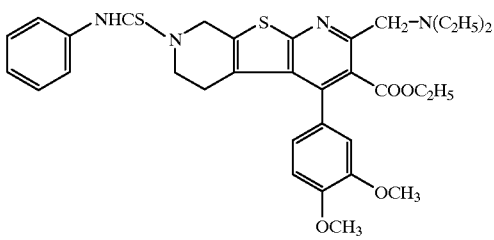

EXAMPLE 12A

A mixture of the compound obtained in Example 5A (1.0 g), phenyl isocyanate (0.27 g) and tetrahydrofuran (20 ml) was stirred at room temperature for 3 hours, after which it was concentrated under reduced pressure. The residue was subjected to silica gel column chromatography and eluted with ethyl acetate-hexane-methanol (20:20:1, v/v) to yield ethyl 2-(N,N-diethylaminomethyl)-4-(3,4-dimethoxyphenyl)-7-phenylcarbamoyl-5,6,7,8-tetrahydrothieno[2,3-b:5,4-c']dipyridine-3-carboxylate (for structural formula, see below) (1.10 g, 88%), which was then recrystallized from ethyl acetate-hexane to yield colorless prismatic crystals having a melting point of 154 to 155° C.

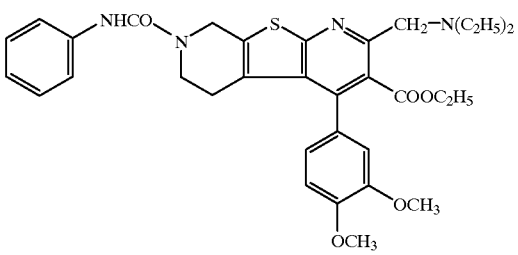

EXAMPLE 13A

A mixture of the compound obtained in Example 5A (1.22 g), methyl isocyanate (0.17 g) and tetrahydrofuran (20 ml) was stirred at room temperature for 5 hours, after which it was concentrated under reduced pressure. The residue was subjected to silica gel column chromatography and eluted with ethyl acetate-hexane-methanol (20:20:1, v/v) to yield ethyl 2-(N,N-diethylaminomethyl)-4-(3,4-dimethoxyphenyl)-7-methylcarbamoyl-5,6,7,8-tetrahydrothieno[2,3-b:5,4-c']dipyridine-3-carboxylate (for structural formula, see below), (0.30 g, 22%), which was then recrystallized from ethyl acetate-hexane to yield colorless prismatic crystals having a melting point of 153 to 155° C.

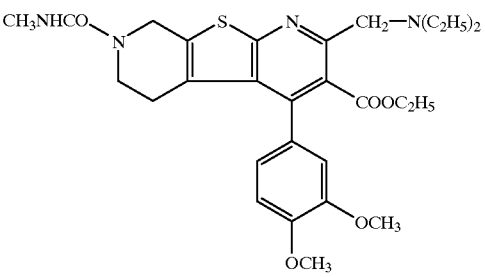

EXAMPLE 14A

A mixture of the compound obtained in Example 5A (1.12 g), ethyl chlorocarbonate (0.35 g), potassium carbonate (0.47 g) and tetrahydrofuran (20 ml) was stirred at room temperature for 3 hours. The reaction mixture was poured over water and extracted with ethyl acetate; the ethyl acetate layer was washed with water and dried (MgSO$_4$), after which the solvent was distilled off. The residue was subjected to silica gel column chromatography and eluted with ethyl acetate-hexane (1:1, v/v) to yield ethyl 2-(N,N-diethylaminomethyl)-4-(3,4-dimethoxyphenyl)-7-ethoxycarbonyl-5,6,7,8-tetrahydrothieno[2,3-b:5,4-c']dipyridine-3-carboxylate (for structural formula, see below) (0.89 g, 56%), which was then recrystallized from ethyl acetate-hexane to yield colorless prismatic crystals having a melting point of 119 to 120° C.

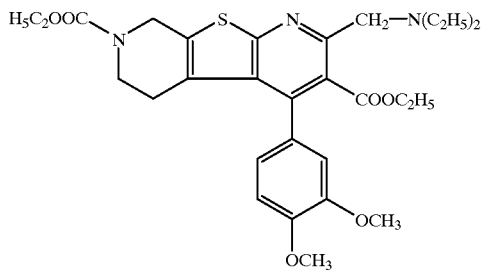

EXAMPLE 15A

A mixture of the compound obtained in Example 5A (2.00 g), acetyl chloride (0.19 g), triethylamine (0.37 ml) and tetrahydrofuran (10 ml) was stirred under ice cooling conditions for 3 hours. The reaction mixture was poured over water and extracted with ethyl acetate. The ethyl acetate layer was washed with water and dried (MgSO$_4$), after which the solvent was distilled off. The residue was subjected to silica gel column chromatography and eluted with chloroform-methanol (100:1, v/v) to yield ethyl 7-acetyl-2-(N,N-diethylaminomethyl)-4-(3,4-dimethoxyphenyl)-5,6,7,8-tetrahydrothieno[2,3-b:5,4-c']dipyridine-3-carboxylate (for structural formula, see below) (0.65 g, 60%) as an amorphous solid having a melting point of 72 to 75° C.

NMR (δ ppm in CDCl3): 0.94 (3H, t, J=7.6 Hz), 0.96 (6H, t, J=7.2 Hz), 1.95–2.15 (2H, m), 2.54 (4H, q, J 7.2 Hz), 2.91 (2H, t, J=5.8 Hz), 3.86 (3H, s), 3.92 (2H, s), 3.94 (3H, s), 3.95 (2H, q, J=7.6 Hz), 4.11 (2H, s), 6.82–6.87 (3H, m).

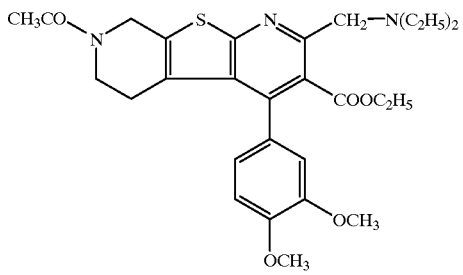

EXAMPLE 16A

A mixture of the compound (3.3 g) obtained in Reference Example 8A, diethylamine (2.2 g) and tetrahydrofuran (70 ml) was heated under refluxing conditions for 6 hours and concentrated under reduced pressure. To the residue was added ethyl acetate, the mixture was washed with water, dried (MgSO$_4$) and concentrated under reduced pressure. The residue was subjected to silica gel column chromatography and eluted with ethyl acetate-hexane (1:1, v/v) to yield ethyl 2-benzyloxycarbonyl-8-(3,4-dimethoxyphenyl)-6-diethylaminomethyl-2,3-dihydro-1H-pyrrolo[3',4':4,5]-thieno[2,3-b]pyridine-7-carboxylate (2.42 g, 69%), which was then recrystallized from isopropyl ether to yield colorless prismatic crystals having a melting point of 142 to 143° C.

EXAMPLE 17A

A mixture of the compound (1.9 g) obtained in Reference Example 8A, 1H-1,2,4-triazole (0.347 g), potassium carbonate (0.463 g) and acetone (50 ml) was heated under refluxing conditions for 6 hours and concentrated under reduced pressure. To the residue was added ethyl acetate, the mixture was washed with water, dried (MgSO$_4$) and concentrated under reduced pressure. The residue was subjected to silica gel column chromatography and eluted with ethyl acetate-methanol (6:1, v/v) to yield ethyl 2-benzyloxycarbonyl-8-(3,4-dimethoxyphenyl)-2,3-dihydro-6-(1,2,4-triazol-1-ylmethyl)-1H-pyrrolo[3',4':4,5]thieno[2,3-b]pyridine-7-carboxylate (0.96 g, 48%), which was then recrystallized from ethyl acetate-hexane to yield colorless prismatic crystals having a melting point of 166 to 167° C.

EXAMPLE 18A

From the fraction subsequently eluted in the column chromatography of Example 17A, ethyl 2-benzyloxycarbonyl-8-(3,4-dimethoxyphenyl)-2,3-dihydro-6-(1,2,4-triazol-4-ylmethyl)-1H-pyrrolo[3',41:4,5]thieno[2,3-b]pyridine-7-carboxylate (0.218 g, 11%) was obtained as colorless powder.

EXAMPLE 19A

Oily sodium hydride (60%, 0.504 g) was added to a solution of 2-pyrrolidone (1.0 g) in N,N-dimethylformamide (60 ml) and the mixture was stirred at room temperature for 20 minutes. Then, the compound (4.5 g) obtained in Reference Example 10A was added thereto, the mixture was stirred at 60° C. for 20 minutes, the reaction mixture was poured over water and the precipitated solid was filtered. This crystal was subjected to silica gel column chromatography and eluted with ethyl acetate-hexane (1:1, v/v) to yield ethyl 7-benzoyl-4-(3,4-methylenedioxy-phenyl)-2-(2-oxo-1-pyrrolidinylmethyl)-5,6,7,8-tetrahydrothieno[2,3-b:5,4-c'] dipyridine-3-carboxylate (0.93 g, 19%), which was then recrystallized from ethyl acetate-hexane to yield light-yellow prismatic crystals having a melting point of 270 to 271° C.

EXAMPLE 20A

In the same manner as in Example 17A, the compound obtained in Reference Example 5A and 1H-1,2,4-triazole were reacted to yield ethyl 7-benzoyl-4-(3,4-dimethoxyphenyl)-5,6,7,8-tetrahydro-2-(1,2,4-triazol-1-ylmethyl)thieno[2,3-b:5,4-c']dipyridine-3-carboxylate, which was then recrystallized from ethyl acetate-hexane to yield colorless prismatic crystals having a melting point of 193 to 194° C.

EXAMPLE 21A

Lithium aluminum hydride (0.164 g) was added to a solution of the compound (5.0 g) obtained in Example 20A in tetrahydrofuran (50 ml), the mixture was stirred at room temperature for 2 hours. Water was added to the reaction mixture and the mixture was extracted with ethyl acetate. The ethyl acetate layer was washed with water, dried (MgSO$_4$) and concentrated under reduced pressure. The residue was subjected to silica gel column chromatography and eluted with chloroform-methanol (50:1, v/v) to yield ethyl 4-(3,4-dimethoxyphenyl)-5,6,7,8-tetrahydro-2-(1,2,4-triazol-1-ylmethyl)thieno[2,3-b:5,4-c']dipyridine-3-carboxylate (3.08 g, 75%), which was then recrystallized from ethyl acetate-hexane to yield colorless prismatic crystals having a melting point of 164 to 165° C.

EXAMPLE 22A

The compound obtained in Example 21A was treated as in Example 7A to yield ethyl 4-(3,4-dimethoxyphenyl)-2-(1,2, 4-triazol-ylmethyl)thieno[2,3-b:5,4-c']dipyridine-3-carboxylate, which was then recrystallized from ethyl acetate to yield colorless prismatic crystals having a melting point of 172 to 174° C.

EXAMPLE 23A

The compound obtained in Reference Example 2A and ethyl 5-(1-methylimidazol-2-yl)-3-oxypentanoate were treated as in Reference Example 4A to yield ethyl 7-benzoyl-4-(3,4-dimethoxyphenyl)-5,6,7,8-tetrahydro-2-[2-(1-methylimidazol-2-yl)ethyl]thieno[2,3-b:5,4-c']dipyridine-3-carboxylate, which was then recrystallized from ethyl acetate to yield colorless prismatic crystals having a melting point of 170 to 17 ° C.

EXAMPLE 24A

The compound obtained in Reference Example 2A and ethyl 3-oxo-5-(1-trityl-1,2,3-triazol-4-yl)pentanoate were treated as in Reference Example 4A to yield ethyl 7-benzoyl-4-(3,4-dimethoxyphenyl)-5,6,7,8-tetrahydro-2-[2-(1,2,3-triazol-4-yl)ethyl]thieno[2,3-b:5,4-c']dipyridine-3-carboxylate, which was then recrystallized from ethyl acetate to yield colorless prismatic crystals having a melting point of 184 to 185° C.

EXAMPLE 25A

In the same manner as in Example 17A, the compound obtained in Reference Example 5A and hydroxylamine hydrochloride were reacted to yield ethyl 7-benzoyl-4-(3,4-dimethoxyphenyl)-2-(N-hydroxy-N-methylaminomethyl)-5,6,7,8-tetrahydrothieno[2,3-b:5,4-c']dipyridine-3-carboxylate, which was then recrystallized from ethyl acetate-hexane to yield colorless prismatic crystals having a melting point of 129 to 130° C.

EXAMPLE 26A

The compound obtained in Reference Example 1A and ethyl 3-oxo-5-(1,2,4-triazol-1-yl)pentanoate were treated as in Reference Example 4A to yield ethyl 7-(4-chlorobenzoyl)-4-(3,4-dimethoxyphenyl) -5,6,7,8-tetrahydro-2-[2-(1,2,4-triazol-1-yl)ethyl]thieno[2,3-b:5,4-c']dipyridine-3-carboxylate, which was then recrystallized from ethyl acetate to yield colorless prismatic crystals having a melting point of 195 to 197° C.

EXAMPLE 27A

The compound obtained in Reference Example 1A and ethyl 3-oxo-6-(1,2,4-triazol-1-yl)hexanoate were treated as in Reference Example 4A to yield ethyl 7-(4-chlorobenzoyl)-4-(3,4-dimethoxyphenyl)-5,6,7,8-tetrahydro-2-[3-(1,2,4-triazol-1-yl]propyl]thieno[2,3-b:5,4-c']dipyridine-3-carboxylate, which was then recrystallized from ethyl acetate to yield colorless prismatic crystals having a melting point of 114 to 116° C.

EXAMPLE 28A

The compound obtained in Reference Example 1A and ethyl 3-oxo-7-(1,2,4-triazol-1-yl)heptanoate were treated as in Reference Example 4A to yield ethyl 7-(4-chlorobenzoyl)-4- (3,4-dimethoxyphenyl) -5,6,7,8-tetrahydro-2-[4-(1,2,4-triazol-1-yl]butyl]thieno[2,3-b:5,4-c' ]dipyridine-3-carboxylate, which was then recrystallized from ethyl acetate to yield colorless prismatic crystals having a melting point of 165 to 166° C.

EXAMPLE 29A

A mixture of the compound (5.99 g) obtained in Example 27A, 4N KOH (24 ml) and ethanol (30 ml) was stirred under refluxing conditions for 1 hour. The reaction mixture was poured over water and the mixture was extracted with ethyl acetate. The ethyl acetate layer was washed with water, dried ($MgSO_4$) and concentrated under reduced pressure. The residue was dissolved in toluene (80 ml), activated manganese dioxide (3.25 g) was added thereto and the mixture was heated under refluxing conditions for 14.5 hours. The insoluble was filtered off, and the filtrate was concentrated under reduced pressure. The residue was subjected to silica gel column chromatography and eluted with ethyl acetate-hexane-methanol (10:10:1, v/v/v) to yield ethyl 4-(3,4-dimethoxyphenyl)-2-[3-(1,2,4-triazol-1-yl)propyl]thieno[2,3-b:5,4-c']dipyridine-3-carboxylate (1.54 g, 33%), which was then recrystallized from ethyl acetate-hexane to yield colorless prismatic crystals having a melting point of 127 to 129° C.

EXAMPLE 30A

The compound obtained in Example 28A was treated as in Example 29A to yield ethyl 4-(3,4-dimethoxyphenyl)-2-[4-(1,2,4-triazol-1-yl)butyl]thieno[2,3-b:5,4,-c']dipyridine-3-carboxylate, which was then recrystallized from ethyl acetate-hexane to yield colorless prismatic crystals having a melting point of 118 to 119° C.

EXAMPLE 31A

A mixture of the compound (0.3 g) obtained in Example 16A and HBr-acetic acid (25%, 0.804 g) was stirred at room temperature for 50 minutes and concentrated under reduced pressure. Ethyl ether was added to the residue and the solid was filtered. This solid was dissolved in dichloromethane, the solution was washed successively with an aqueous saturated solution of sodium bicarbonate and water, dried ($MgSO_4$) and concentrated under reduced pressure to yield ethyl 8-(3,4-dimethoxyphenyl)-6-diethyl-aminomethyl-2,3-dihydro-1H-pyrrolo[3',4':4,5]thieno[2,3-b]pyridine-7-carboxylate (0.21 g, 90%) as powder.

NMR ($\delta$ ppm in $CDCl_3$): 0.94 (3H, t, J=7.4 Hz), 1.01 (6H, t, J=7.0 Hz), 2.62 (4H, q, J=7.0 Hz), 3.51–3.75 (2H, m), 3.87 (3H, s), 3.89–4.06 (7H, m), 4.29–4.41 (2H, m), 6.78–6.88 (2H, m), 6.92 (1H, d, J=8.8 Hz)

EXAMPLE 32A

The compound obtained in Example 31A was treated as in Example 15A to yield ethyl 2-acetyl-8-(3,4-dimethoxyphenyl)-6-diethylaminomethyl-2,3-dihydro-1H-pyrrolo[3',4':4,5]thieno[2,3-b]pyridine-7-carboxylate, which was then recrystallized from ethyl acetate-hexane to yield a colorless prismatic crystal having a melting point of 123 to 124° C.

EXAMPLES 33A–35A

In the same manner as in Example 6A, the compounds listed in Table 10 were obtained.

TABLE 10

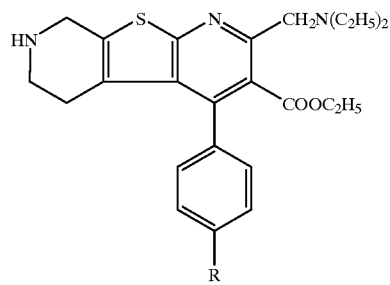

| Example No. | R | Melting point (° C.) | Recrystallizing solvent |
|---|---|---|---|
| 33A | C$_2$H$_5$ | 107–108 | Ethyl acetate-Isopropyl ether |
| 34A | C$_3$H$_7$ | 75–79 | Ethyl acetate-Isopropyl ether |
| 35A | (CH$_3$)$_2$CH | 155–157 | Ethyl acetate-Isopropyl ether |

EXAMPLES 36A–38A

In the same manner as in Example 12A, the compounds listed in Table 11 were obtained.

TABLE 11

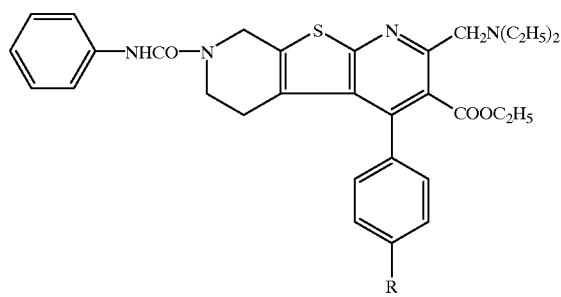

| Example No. | R | Melting point (° C.) | Recrystallizing solvent |
|---|---|---|---|
| 36A | C$_2$H$_5$ | 112–114 | Ethyl acetate-Isopropyl ether |
| 37A | C$_3$H$_7$ | 116–118 | Ethyl acetate-Hexane |
| 38A | (CH$_3$)$_2$CH | 167–168 | Ethyl acetate-Hexane |

EXAMPLES 39A–41A

In the same manner as in Example 14A, the compounds listed in Table 12 were obtained.

TABLE 12

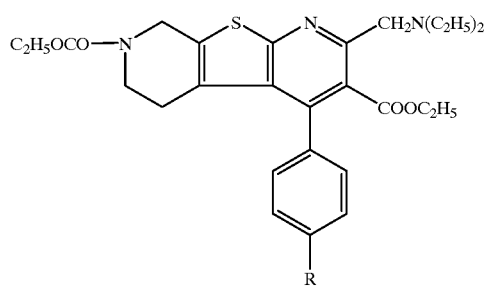

| Example No. | R | Melting point (° C.) | Recrystallizing solvent |
|---|---|---|---|
| 39A | C$_2$H$_5$ | 97–99 | Isopropyl ether-Hexane |
| 40A | C$_3$H$_7$ | 99–100 | Isopropyl ether-Hexane |
| 41A | (CH$_3$)$_2$CH | 139–140 | Ethyl acetate-Isopropyl ether |

EXAMPLES 42A–44A

In the same manner as in Example 9A, the compounds listed in Table 13 were obtained.

TABLE 13

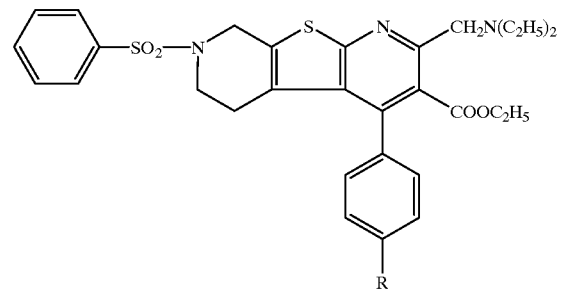

| Example No. | R | Melting point (° C.) | Recrystallizing solvent |
|---|---|---|---|
| 42A | C$_2$H$_5$ | 140–141 | Ethyl acetate-Hexane |
| 43A | C$_3$H$_7$ | 133–135 | Ethyl acetate-Hexane |
| 44A | (CH$_3$)$_2$CH | 155–156 | Ethyl acetate-Ethyl ether |

EXAMPLES 45A–46A

In the same manner as in Example 7A, the compounds listed in Table 14 were obtained.

TABLE 14

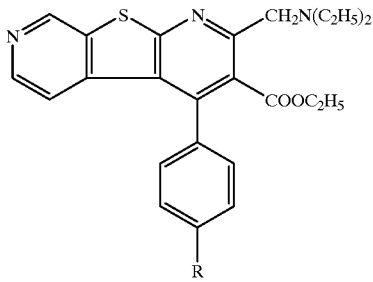

| Example No. | R | Melting point (° C.) | Recrystallizing solvent |
|---|---|---|---|
| 45A | $C_3H_7$ | 175–176 | Ethyl acetate-Isopropyl ether |
| 46A | $(CH_3)_2CH$ | 153–155 | Ethyl acetate |

EXAMPLE 47A

The compound obtained in Example 21A was treated as in Example 7A to yield ethyl 4-(3,4-dimethoxyphenyl)-2-(1,2,4-triazol-1-ylmethyl)thieno[2,3-b:5,4-c']dipyridine-3-carboxylate, which was then recrystallized from ethyl acetate to yield colorless prismatic crystals having a melting point of 172 to 174° C.

EXAMPLE 48A

In the same manner as in Example 16A, the compound obtained in Reference Example 18A and diethylamine were reacted to yield ethyl 7-(4-chlorobenzoyl)-2-diethylaminomethyl-4-(4-isopropoxy-3-methoxyphenyl)-5,6,7,8-tetrahydrothieno[2,3-b:5,4-c']dipyridine-3-carboxylate, which was then recrystallized from ethyl acetate-hexane to yield colorless prismatic crystals.

NMR (δ ppm in CDCl$_3$): 0.92 (3H, t, J=7.2 Hz), 0.99 (6H, t, J=7.2 Hz), 1.40 (3H, d, J=6.2 Hz), 1.43 (3H, d, J=6.2 Hz), 2.13 (2H, br s), 2.53 (4H, q, J=7.2 Hz), 3.49 (2H, br s), 3.89 (3H, s), 3.94 (2H, q, J=7.2 Hz), 4.62 (1H, m), 4.72 (1H, br s), 4.96 (1H, br s), 6.78–6.82 (2H, m), 6.94 (1H, d, J=8.4 Hz), 7.49 (4H, s)

EXAMPLE 49A

A mixture of the compound (8.9 g) obtained in Example 48A, 4N KOH (18 ml) and ethanol (150 ml) was stirred under refluxing conditions for 5 hours. The reaction mixture was poured over water and the mixture was extracted with ethyl acetate. The ethyl acetate layer was washed with water, dried (MgSO$_4$) and concentrated under reduced pressure. The residue was subjected to silica gel column chromatography and eluted with ethyl acetate-hexane (4:1, v/v) to yield ethyl 2-diethylaminomethyl-4-(4-isopropoxy-3-methoxyphenyl)-5,6,7,8-tetrahydrothieno[2,3-b:5,4-c']dipyridine-3-carboxylate (6.5 g, 88%), which was then recrystallized from ethyl acetate-hexane to yield colorless prismatic crystals.

NMR (δ ppm in CDCl$_3$): 0.91 (3H, t, J=7.0 Hz), 0.92 (3H, t, J=7.0 Hz), 0.95 (3H, t, J=7.2 Hz), 1.39 (3H, d, J=6.2 Hz), 1.42 (3H, d, J=6.2 Hz), 1.96–2.06 (4H, q, J=7.0 Hz), 2.91 (2H, t, J=5.8 Hz), 3.83 (3H, s), 3.91 (2H, s), 3.93 (2H, q, J=7.2 Hz), 4.10 (2H, s), 4.60 (1H, m), 6.78–6.82 (2H, m), 6.91 (1H, d, J=8.6 Hz)

EXAMPLE 50A

The compound obtained in Example 49A was treated as in Example 7A to yield ethyl 2-diethylaminomethyl-4-(4-isopropoxy-3-methoxyphenyl)thieno[2,3-b:5,4-c']dipyridine-3-carboxylate as an oil.

NMR (δ ppm in CDCl$_3$): 0.95 (3H, t, J=7.2 Hz), 0.98 (6H, t, J=7.0 Hz), 1.44 (3H, d, J=6.0 Hz), 1.49 (3H, d, J=6.0 Hz), 2.58 (4H, q, J=7.0 Hz), 3.82 (3H, s), 3.99 (2H, q, J=7.2 Hz), 4.00 (2H, s), 4.69 (1H, m), 6.81 (1H, dd, J=5.6 & 0.8 Hz), 6.89–6.98 (2H, m), 7.07 (1H, d, J=8.6 Hz), 8.33 (1H, d, J=5.6 Hz), 9.13 (1H, d, J=0.8 Hz)

EXAMPLE 51A

Titanium tetrachloride (0.85 ml) was added dropwise to a solution of the compound (1.0 g) obtained in Example 50A in dichloromethane (35 ml) under ice-cooling, and the mixture was stirred at 0° C. for 1.5 hours. The reaction mixture was poured over ice-water, and the mixture was extracted with dichloromethane. The dichloromethane layer was washed successively with an aqueous saturated solution of sodium bicarbonate and water, dried (MgSO$_4$) and concentrated under reduced pressure. The residue was subjected to silica gel column chromatography and eluted with ethyl acetate-chloroform (1:1, v/v) to yield ethyl 2-diethylaminomethyl-4-(4-hydroxy-3-methoxyphenyl)thieno[2,3-b:5,4-c']dipyridine-3-carboxylate (0.41 g, 44%), which was then recrystallized from ethyl acetate to yield colorless prismatic crystals having a melting point of 179 to 181° C.

EXAMPLE 52A

In the same manner as in Example 17A, the compound obtained in Reference Example 5A and 1-methylhydantoin were reacted to yield ethyl 7-benzoyl-4-(3,4-dimethoxyphenyl)-2-(l-methylhydantoin-3-ylmethyl)-5,6,7,8-tetrahydrothieno[2,3-b:5,4-c']dipyridine-3-carboxylate, which was then recrystallized from ethyl acetate to yield colorless prismatic crystals having a melting point of 185 to 187 ° C.

EXAMPLE 53A

In the same manner as in Example 16A, the compound obtained in Reference Example 29A and diethylamine were reacted to yield ethyl 6-(4-chlorobenzoyl)-2-diethylaminomethyl-4-(3,4-dimethoxyphenyl)-5,6,7,8-tetrahydrothieno[2,3-b:4,5-c']dipyridine-3-carboxylate, which was then recrystallized from ethyl acetate-hexane to yield colorless prismatic crystals having a melting point of 91 to 92° C.

EXAMPLE 54A

A mixture of the compound (1.8 g) obtained in Example 53A, a solution of potassium hydroxide (0.6 g) in water (10 ml) and ethanol (20 ml) was heated under refluxing conditions for 5 hours, poured over water and extracted with ethyl acetate. The ethyl acetate layer was washed with water, dried (MgSO$_4$) and concentrated under reduced pressure to yield ethyl 2-diethylaminomethyl-4-(3,4-dimethoxyphenyl)-5,6,7,8-tetrahydrothieno[2,3-b:4,5-c']dipyridine-3-carboxylate as an oil.

NMR (δ ppm in CDCl$_3$): 0.93 (3H, t, J=7.2 Hz), 0.95 (6H, t, J=7.2 Hz), 2.54 (4H, q, J=7.2 Hz), 2.7–3.3 (6H, m), 3.85

(3H, s), 3.91 (2H, s), 3.92 (2H, q, J=7.2 Hz), 3.93 (3H, s), 6.7–7.0 (3H, m)

EXAMPLE 55A

In the same manner as in Example 7A, the compound obtained in Example 54A and activated manganese dioxide were reacted to yield ethyl 2-diethylaminomethyl-4-(3,4-dimethoxyphenyl)thieno[2,3-b:4,5-c']dipyridine-3-carboxylate, which was then recrystallized from ethyl acetate-hexane to yield colorless prismatic crystals having a melting point of 141 to 142° C.

EXAMPLE 56A

In the same manner as in Example 17A, the compound obtained in Reference Example 30A and 1H-1,2,4-triazole were reacted to yield ethyl 8-benzyloxycarbonyl-4-(3,4-dimethoxyphenyl)-5,6,7,8-tetrahydro-2-(1,2,4-triazol-1-ylmethyl)thieno[2,3-b:5,4-b']dipyridine-3-carboxylate, which was then recrystallized from ethyl acetate-chloroform as colorless prismatic crystals having a melting point of 184 to 185° C.

EXAMPLE 57A

From the fraction subsequently eluted in the column chromatography of Example 56, ethyl 8-benzyloxycarbonyl-4-(2,3-dimethoxyphenyl)-5,6,7,8-tetrahydro-2-(1,2,4-triazol-1-ylmethyl)thieno[2,3-b:5,4-b']dipyridine-3-carboxylate was obtained, which was then recrystallized from ethyl acetate-chloroform to yield colorless prismatic crystals having a melting point of 184 to 185° C.

EXAMPLE 58A

In the same manner as in Example 16A, the compound obtained in Reference Example 30A and diethylamine were reacted to yield ethyl 8-benzyloxycarbonyl-2-diethylaminomethyl-4-(3,4-dimethoxyphenyl)-5,6,7,8-tetrahydrothieno[2,3-b:5,4-b']dipyridine-3-carboxylate, which was then recrystallized from ethyl acetate-hexane to yield colorless prismatic crystals having a melting point of 138 to 139° C.

EXAMPLE 59A

In the same manner as in Example 17A, the compound obtained in Example 31A and 1H-1,2,4-triazole were reacted to yield ethyl 6-benzyloxycarbonyl-4-(3,4-dimethoxyphenyl)-5,6,7,8-tetrahydro-2-(1,2,4-triazol-1-ylmethyl)thieno[2,3-b:4,5-c']dipyridine-3-carboxylate, which was then recrystallized from ethyl acetate-hexane to yield colorless prismatic crystals having a melting point of 169 to 170° C.

EXAMPLE 60A

From the fraction subsequently eluted in the column chromatography of Example 59A, ethyl 6-benzyloxycarbonyl-4-(3,4-dimethoxyphenyl)-5,6,7,8-tetrahydro-2-(1,2,4-triazol-4-ylmethyl)thieno[2,3-b:4,5-c'] dipyridine-3-carboxylate, which was then recrystallized from ethyl acetate-hexane to yield colorless prismatic crystals having a melting point of 181 to 182° C.

EXAMPLE 61A

A mixture of the compound (0.6 g) obtained in Example 58, Raney nickel (1.0 g) and ethanol (30 ml) was subjected to catalytic hydrogenation at room temperature and 1 atmospheric pressure. The catalyst was filtered off and the filtrate was concentrated under reduced pressure to yield ethyl 2-diethylaminomethyl-4-(3,4-dimethoxyphenyl)-5,6,7,8-tetrahydrothieno[2,3-b:5,4-b']dipyridine-3-carboxylate as an oil.

NMR (δ ppm in CDCl$_3$): 0.90–0.99 (9H, m), 1.65–1.72 (2H, m), 1.86–1.89 (2H, m), 2.53 (4H, q, J=7.2 Hz), 3.27–3.30 (2H, m), 3.84 (2H, s), 3.87 (3H, s), 3.92 (2H, q, J=7.0 Hz), 3.93 (3H, s), 6.83–6.86 (3H, m)

EXAMPLE 62A

From the compound obtained in Example 56A in the same manner as in Example 31A, ethyl 4-(3,4-dimethoxyphenyl)-5,6,7,8-tetrahydro-2-(1,2,4-triazol-1-ylmethyl)thieno[2,3-b:5,4-b']dipyridine-3-carboxylate was obtained as an oil.

NMR (δ ppm in CDCl$_3$): 0.89 (3H, t, J=7.0 Hz), 1.68–1.74 (2H, m), 1.86–1.92 (2H, m), 3.27–3.30 (2H, m), 3.85 (3H, s), 3.93 (3H, s), 3.94 (2H, q, J=7.0 Hz), 5.54 (2H, d, J=1.8 Hz), 6.79–6.89 (3H, m), 7.91 (1H, s), 8.21 (1H, s)

EXAMPLE 63A

From the compound obtained in Example 59A in the same manner as in Example 31A, ethyl 4-(3,4-dimethoxyphenyl)-5,6,7,8-tetrahydro-2-(1,2,4-triazol-1-ylmethyl)thieno[2,3-b:4,5-c']dipyridine-3-carboxylate was obtained as colorless powder having a melting point of 180 to 181° C.

NMR (δ ppm in CDCl$_3$): 0.88 (3H, t, J=7.0 Hz), 2.91 (2H, t, J=5.3 Hz), 3.11 (2H, t, J=5.3 Hz), 3.21–3.22 (2H, m), 3.84 (3H, s), 3.93 (3H, s), 3.95 (2H, q, J=7.0 Hz), 5.66 (2H, s), 6.77–6.91 (3H, m), 7.93 (1H, s), 8.26 (1H, s)

EXAMPLE 64A

In the same manner as in Example 7A, the compound obtained in Example 61A and activated manganese dioxide were reacted to yield ethyl 2-diethylaminomethyl-4-(3,4-dimethoxyphenyl)thieno[2,3-b:5,4-b']dipyridine-3-carboxylate, which was then recrystallized from ethyl acetate-hexane to yield colorless prismatic crystals having a melting point of 156 to 157° C.

EXAMPLE 65A

In the same manner as in Example 7A, the compound obtained in Example 62A and activated manganese dioxide were reacted to yield ethyl 4-(3,4-dimethoxyphenyl)-2-(1,2,4-triazol-1-ylmethyl)thieno[2,3-b:5,4-b']dipyridine-3-carboxylate, which was then recrystallized from ethyl acetate-hexane to yield colorless prismatic crystals having a melting point of 180 to 182° C.

EXAMPLE 66A

In the same manner as in Example 7A, the compound obtained in Example 63A and activated manganese dioxide were reacted to yield ethyl 4-(3,4-dimethoxyphenyl)-2-(1,2,4-triazol-1-ylmethyl)thieno[2,3-b:4,5-c']dipyridine-3-carboxylate, which was then recrystallized from ethyl acetate-hexane to yield colorless prismatic crystals having a melting point of 166 to 167° C.

B. PRODUCTION OF THE COMPOUND OF THE FORMULA (I')

REFERENCE EXAMPLE 1B

A solution of ethyl 3,4-dimethoxybenzoate (17.8 g) and acetonitrile (7.0 g) in toluene (30 ml) was added drop by drop at 100° C. to a suspension of oily sodium hydride (60%, 6.8 g) in toluene (170 ml) and N,N-dimethylformamide (DMF) (17 ml). After dropwise addition, this mixture was further stirred at 100° C. for 3 hours. The reaction mixture was poured over ice-water to separate the organic layer. The water layer was acidified with 2 N hydrochloric acid and extracted with ethyl acetate. The ethyl acetate layer was washed with water and dried (MgSO$_4$), after which the solvent was distilled off under reduced pressure to yield ω-cyano-3,4-dimethoxyacetophenone (14.0 g, 80%), which was then recrystallized from ethyl acetate to yield colorless needle crystals having a melting point of 141 to 142° C.

REFERENCE EXAMPLE 2B

A mixture of ω-cyano-3,4-dimethoxyacetophenone (10.0 g), sulfur (1.7 g), 1-benzyl-4-piperidone (10.1 g), morpholine (4.7 g) and ethanol (50 ml) was stirred under refluxing conditions for 2 hours. The reaction mixture was poured over ice-water, sequentially washed with 2 N HCl and 1 N KOH in that order and dried (MgSO$_4$), after which the solvent was distilled off. The residue was subjected to silica gel column chromatography and eluted with chloroform-ethyl acetate (20:1, v/v) to yield 2-amino-6-benzyl-3-(3,4-dimethoxybenzoyl)-4,5,6,7-tetrahydrothieno[2,3-c]pyridine (8.4 g, 42%), which was then recrystallized from ethanol to yield yellow prismatic crystals having a melting point of 149 to 150° C.

REFERENCE EXAMPLE 3B

A mixture of 2-amino-6-benzyl-3-(3,4-dimethoxybenzoyl)-4,5,6,7-tetrahydrothieno[2,3-c]pyridine (10.0 g), 1,3-dichloroacetone (3.4 g), concentrated sulfuric acid (2.6 g) and acetic acid (200 ml) was stirred at 90° C. for 4 hours. After the reaction mixture was concentrated under reduced pressure, the residue was alkalinized with 2 N NaOH and then extracted with dichloromethane. The dichloromethane layer was washed with water and dried (MgSO$_4$), after which the solvent was distilled off. The residue was subjected to silica gel column chromatography and eluted with ethyl acetate-hexane (1:1, v/v) to yield 7-benzyl-3-chloro-2-chloromethyl-4-(3,4,-dimethoxyphenyl)-5,6,7,8-tetrahydrothieno-[2,3-b:5,4-c']dipyridine (for structural formula, see below) (3.5 g, 29%), which was then recrystallized from ethyl acetate-hexane to yield colorless prismatic crystals having a melting point of 171 to 172° C.

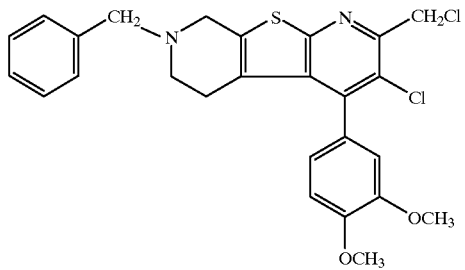

REFERENCE EXAMPLE 4B

In the same manner as in Example 2B, ω-cyano-3,4-dimethoxyacetophenone, 1-benzoyl-4-piperidone and sulfur were reacted to yield 2-amino-6-benzoyl-3-(3,4-dimethoxybenzoyl)-4,5,6,7-tetrahydrothieno[2,3-c]pyridine, which was then recrystallized from ethanol to yield light-yellow prismatic crystals having a melting point of 143 to 145° C.

REFERENCE EXAMPLE 5B

A mixture of the compound (1.0 g) obtained in Reference Example 4B, 1,3-dichloroacetone (0.331 g), p-toluenesulfonic acid monohydrate (0.045 g) and benzene (15 ml) was heated under refluxing conditions for 6 hours and concentrated under reduced pressure. Ethyl acetate was added to the residue and the mixture was washed successively with water, an aqueous saturated solution of sodium bicarbonate and water, dried (MgSO$_4$) and concentrated under reduced pressure. The residue was subjected to silica gel column chromatography and eluted with ethyl acetate-hexane (3:2, v/v) to yield 7-benzoyl-3-chloro-2-chloromethyl-4-(3,4-dimethoxyphenyl)-5,6,7,8-tetrahydrothieno[2,3-b:5,4-c']dipyridine (0.484 g, 40%), which was then recrystallized from ethyl acetate-hexane to yield colorless prismatic crystals having a melting point of 208 to 209° C.

REFERENCE EXAMPLE 6B

In the same manner as in Reference Example 1B, ethyl 2,3-dimethoxybenzoate and acetonitrile were reacted to yield ω-cyano-2,3-dimethoxyacetophenone, which was then recrystallized from ethyl acetate-hexane to yield colorless needle crystals having a melting point of 94 to 95° C.

REFERENCE EXAMPLE 7B

In the same manner as in Reference Example 2B, ω-cyano-2,3-dimethoxyacetophenone, 1-benzyl-4-piperidone and sulfur were reacted to yield 2-amino-6-benzyl-3-(2,3-dimethoxybenzoyl)-4,5,6,7-tetrahydrothieno[2,3-c]pyridine, which was then recrystallized from ethyl acetate-hexane to yield light-yellow prismatic crystals having a melting point of 172 to 173° C.

REFERENCE EXAMPLE 8B

In the same manner as in Reference Example 5B, the compound obtained in Reference Example 7B and 1,3-dichloroacetone were reacted to yield 7-benzyl-3-chloro-2-chloromethyl-4-(2,3-dimethoxyphenyl)-5,6,7,8-tetrahydrothieno[2,3-b:5,4-c']dipyridine, which was then recrystallized from ethyl acetate-hexane to yield colorless prismatic crystals having a melting point of 137 to 138° C.

REFERENCE EXAMPLE 9B

In the same manner as in Reference Example 1B, ethyl 4-isopropoxy-3-methoxybenzoate and acetonitrile were reacted to yield ω-cyano-4-isopropoxy-3-methoxyacetophenone, which was then recrystallized from ethyl acetate-hexane to yield colorless needle crystals having a melting point of 114 to 115° C.

REFERENCE EXAMPLE 10B

In the same manner as in Reference Example 2B, ω-cyano-4-isopropoxy-3-methoxyacetophenone, 1-benzoyl- 4-piperidone and sulfur were reacted to yield 2-amino-6-benzoyl-3-(4-isopropoxy-3-methoxybenzoyl)-4,5,6,7-tetrahydrothieno[2,3-c]pyridine, which was then recrystallized from ethyl acetate-hexane to yield yellow prismatic crystals having a melting point of 158 to 160° C.

REFERENCE EXAMPLE 11B

In the same manner as in Reference Example 5B, the compound obtained in Reference Example 10B and 1,3- dichloroacetone were reacted to yield 7-benzoyl-3-chloro-2-chloromethyl-4-(4-isopropoxy-3-methoxyphenyl)-5,6,7,8-tetrahydrothieno[2,3-b:5,4-c']dipyridine as an oil.

NMR (δ ppm in CDCl₃): 1.41 (6H, d, J=6.0 Hz), 2.09–2.35 (2H, m), 3.30–3.81 (2H, m), 3.89 (3H, s), 4.30–4.70 (3H, m), 4.96 (2H, s), 6.78 (1H, d, J=1.8 Hz), 6.80 (1H, dd, J=8.0 & 1.8 Hz), 6.97 (1H, d, J=8.0 Hz), 7.35–7.55 (5H, m)

REFERENCE EXAMPLE 12B

In the same manner as in Reference Example 2B, ω-cyano-4-isopropoxy-3-methoxyacetophenone, 1-benzyl-4-piperidone and sulfur were reacted to yield 2-amino-6-benzyl-3-(4-isopropoxy-3-methoxybenzoyl)-4,5,6,7-tetrahydrothieno[2,3-c]pyridine, which was then recrystallized from ethyl acetate-hexane to yield yellow prismatic crystals having a melting point of 113 to 114° C.

REFERENCE EXAMPLE 13B

In the same manner as in Reference Example 5B, the compound obtained Reference Example 12B and 1,3-dichloroacetophenone were reacted to yield 7-benzyl-3-chloro-2-chloromethyl-4-(4-isopropoxy-3-methoxyphenyl)-5,6,7,8-tetrahydrothieno[2,3-b:5,4-c']dipyridine, which was then recrystallized from ethyl acetate-hexane to yield light-yellow prismatic crystals having a melting point 173 to 174° C.

EXAMPLE 1B

A mixture of the compound obtained in Reference Example 3B (1.5 g), an aqueous solution of ethylamine (70%, 4.8 g) and N,N-dimethylformamide (50 ml) was stirred at room temperature for 3 days, after which it was concentrated under reduced pressure. After water was poured, the residue was extracted with ethyl acetate. The ethyl acetate layer was washed with water and dried (MgSO₄), after which the solvent was distilled off. The residue was subjected to silica gel column chromatography and eluted with ethyl acetate to yield 7-benzyl-3-chloro-4-(3,4,-dimethoxyphenyl)-2-ethylaminomethyl-5,6,7,8-tetrahydrothieno[2,3-b:5,4-c']dipyridine (for structural formula, see below) (0.5 g, 33%), which was then recrystallized from ethanol to yield colorless prismatic crystals having a melting point of 135 to 136° C.

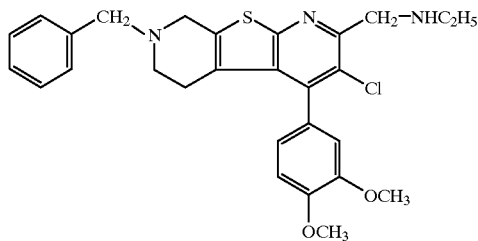

EXAMPLE 2B

A mixture of the compound obtained in Reference Example 3B (1.5 g), diethylamine (1.1 g) and tetrahydrofuran (50 ml) was stirred under refluxing conditions for 10 hours, after which it was concentrated under reduced pressure. After water was poured, the residue was extracted with ethyl acetate. The ethyl acetate layer was washed with water and dried (MgSO₄), after which the solvent was distilled off. The residue was subjected to silica gel column chromatography and eluted with ethyl acetate to yield 7-benzyl-3-chloro-2-(N,N-diethylaminomethyl)-4-(3,4-dimethoxyphenyl)-5,6,7,8-tetrahydrothieno[2,3-b:5,4-c']dipyridine (for structural formula, see below) (0.5 g, 33%), which was then recrystallized from ethyl acetate-hexane to yield colorless needle crystals having a melting point of 150 to 151° C.

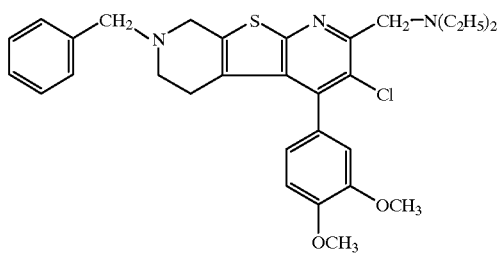

EXAMPLE 3B

A mixture of the compound (1.0 g) obtained in Reference Example 3B, tert-butylamine (2.9 g), potassium carbonate (0.276 g) and acetone (30 ml) was stirred at room temperature for 2 days and concentrated under reduced pressure. Ethyl acetate was added to the residue, the mixture was washed with water, dried (MgSO₄) and concentrated under reduced pressure. The residue was subjected to silica gel column chromatography and eluted with ethyl acetate to yield 7-benzyl-2-(tert-butylaminomethyl)-3-chloro-4-(3,4-dimethoxyphenyl)-5,6,7,8-tetrahydrothieno[2,3-b:5,4-c']dipyridine (0.68 g, 64%), which was then recrystallized from isopropyl ether to yield colorless prismatic crystals having a melting point of 134 to 135° C.

EXAMPLE 4B

In the same manner as in Example 3B, the compound obtained in Reference Example 3B and tert-amylamine were reacted to yield 2-(tert-amylaminomethyl)-7-benzyl-3-chloro-4-(3,4-dimethoxyphenyl)-5,6,7,8-tetrahydrothieno[2,3-b:5,4-c']dipyridine, which was then recrystallized from isopropyl ether to yield colorless prismatic crystals having a melting point of 128 to 129° C.

EXAMPLE 5B

In the same manner as in Example 3B, the compound obtained in Reference Example 3B and cyclopropylamine were reacted to yield 7-benzyl-3-chloro-2-(cyclopropylaminomethyl)-4-(3,4-dimethoxyphenyl)-5,6,7,8-tetrahydrothieno[2,3-b:5,4-c']dipyridine, which was then recrystallized from isopropyl ether to yield colorless prismatic crystals having a melting point of 131 to 132° C.

EXAMPLE 6B

Oily sodium hydride (60%, 0.125 g) was added to a solution of 2-hydroxypyridine (0.297 g) in N,N-dimethylformamide (20 ml) and the mixture was stirred at room temperature for 15 minutes. Then, the compound (1.2 g) obtained in Reference Example 3B was added thereto, the mixture was stirred at 80° C. for 30 minutes, after which the reaction mixture was poured over water and extracted with ethyl acetate. The ethyl acetate layer was washed with water, dried (MgSO₄) and concentrated under reduced pressure. The residue was subjected to silica gel column chromatography and eluted with ethyl acetate-hexane (2:1, v/v) to yield 7-benzyl-3-chloro-4-(3,4-dimethoxyphenyl)-2-(2-pyridyloxymethyl)-5,6,7,8-tetrahydrothieno [2,3-b:5,4-c'] dipyridine (0.13 g, 10%), which was then recrystallized from ethyl acetate-hexane to yield light-yellow prismatic crystal having a melting point of 165 to 167° C.

EXAMPLE 7B

From the fraction subsequently eluted in the column chromatography of Example 6B, 7-benzyl-3-chloro-4-(3,4-dimethoxyphenyl)-2-(1,2-dihydro-2-oxopyridin-1-ylmethyl)-5,6,7,8-tetrahydrothieno[2,3-b:5,4-c']dipyridine (1.0 g, 75%) was obtained as colorless powder.

EXAMPLE 8B

In the same manner as in Example 2B, the compound obtained in Reference Example 5B and tert-butylamine were reacted to yield 7-benzoyl-2-(tert-butylaminomethyl)-3-chloro-4-(3,4-dimethoxyphenyl)-5,6,7,8-tetrahydrothieno [2,3-b:5,4-c']dipyridine having a melting point of 204 to 205° C.

EXAMPLE 9B

In the same manner as in Example 2B, the compound obtained in Reference Example 11B and tert-butylamine were reacted to yield 7-benzoyl-2-(tert-butylaminomethyl)-3-chloro-4-(4-isopropoxy-3-methoxyphenyl)-5,6,7,8-tetrahydrothieno[2,3-b:5,4-c']dipyridine having a melting point of 165 to 166° C.

EXAMPLE 10B

The compound (3.0 g) obtained in Example 8B, an aqueous solution of potassium hydroxide (4N, 6.8 ml) and 2-methoxyethanol (50 ml) were stirred at 100° C. for 10 hours, after which it was concentrated under reduced pressure. Water was poured over the residue and extracted with dichloromethane. The dichloromethane layer was washed with water, dried ($MgSO_4$) and concentrated under reduced pressure. The residue was subjected to silica gel column chromatography and eluted with ethyl acetate to yield 2-(tert-butylaminomethyl)-4-chloro-4-(3,4-dimethoxyphenyl)-5,6,7,8-tetrahydrothieno[2,3-b:5,4-c'] dipyridine (1.25 g, 51%), which was then recrystallized from ethyl acetate-hexane to yield colorless prismatic crystals having a melting point of 162 to 163° C.

EXAMPLE 11B

The compound obtained in Example 9B was subjected to the same manner as in Example 10B to yield 2-(tert-butylaminomethyl)-3-chloro-4-(4-isopropoxy-3-methoxyphenyl)-5,6,7,8-tetrahydrothieno[2,3-b:5,4-c'] dipyridine, which was then recrystallized from ethyl acetate-hexane to yield light-yellow prismatic crystals having a melting point of 157 to 158° C.

EXAMPLE 12B

In the same manner as in Example 3B, the compound obtained in Reference Example 8B and piperidine were reacted to yield 7-benzyl-3-chloro-4-(2,3-dimethoxyphenyl)-5,6,7,8-tetrahydro-2-piperidinomethylthieno[2,3-b:5,4-c']dipyridine, which was then treated with ethanolic hydrochloride to yield the hydrochloride as colorless powder having a melting point of 173 to 174° C.

EXAMPLE 13B

In the same manner as in Example 3B, the compound obtained in Reference Example 8B and morpholine were reacted to yield 7-benzyl-3-chloro-4-(2,3-dimethoxyphenyl)-2-morpholinomethyl-5,6,7,8-tetrahydrothieno[2,3-b:5,4-c']dipyridine, which was then treated with ethanolic hydrochloride to yield the hydrochloride as light-yellow powder having a melting point of 176 to 177° C.

EXAMPLE 14B

In the same manner as in Example 2B, the compound obtained in Reference Example 3B and N-acetylpiperazine were reacted to yield 2-(4-acetylpiperazin-1-ylmethyl)-7-benzyl-3-chloro-4-(3,4-dimethoxyphenyl)- 5,6,7,8-tetrahydrothieno[2,3-b:5,4-c']dipyridine, which was then recrystallized from ethyl acetate-hexane to yield colorless needle crystals having a melting point of 183 to 184° C.

EXAMPLE 15B

A mixture of the compound (1.0 g) obtained in Reference Example 3B, pyrrolidine (0.284 g) and ethanol (30 ml) was heated under refluxing conditions for 3 hours and concentrated under reduced pressure. Ethyl acetate was added to the residue, which was washed with water, dried ($MgSO_4$) and concentrated under reduced pressure. The residue was subjected to silica gel column chromatography and eluted with ethyl acetate-hexane (2:1, v/v) to yield 7-benzyl-3-chloro-4-(3,4-dimethoxyphenyl)-2-(1-pyrrolidinylmethyl)-5,6,7,8-tetrahydrothieno[2,3-b:5,4-c')dipyridine (0.65 g, 61%), which was then recrystallized from ethyl acetate-hexane to yield colorless prismatic crystals having a melting point of 157 to 158° C.

EXAMPLE 16B

A mixture of the compound (3.0 g) obtained in Reference Example 3B, sodium diformamide [$NaN(CHO)_2$] (0.856 g) and N,N-dimethylformamide (40 ml) was stirred at 80° C. for 3 hours. The reaction mixture was poured over water and extracted with ethyl acetate. The ethyl acetate layer was washed with water, dried ($MgSO_4$) and concentrated under reduced pressure. The residue was subjected to silica gel column chromatography and eluted with ethyl acetate-hexane (1:1, v/v) to yield 7-benzyl-3-chloro-2-(diformylaminomethyl)-4-(3,4-dimethoxyphenyl)-5,6,7,8-tetrahydrothienot2,3b:5,4-c']dipyridine (1.0 g, 31%) as colorless powder.

Elemental Analysis for $C_{28}H_{26}N_3O_4SCl•½H_2O$: Calcd: C, 61.70; H, 4.99; N, 7.71; Found: C, 61.94; H, 5.30; N, 7.35.

EXAMPLE 17B

From the fraction subsequently eluted in the column chromatography of Example 16B, 7-benzyl-3-chloro-4-(3,4-dimethoxyphenyl)-2-formylaminomethyl-5,6,7,8-tetrahydrothieno[2,3-b:5,4-c']dipyridine (0.7 g, 23%) as colorless powder.

Elemental Analysis for $C_{27}H_{26}N_3O_3SCl•¼H_2O$: Calcd: C, 63.27; H, 5.21; N, 8.20; Found: C, 63.27; H, 5.54; N, 7.85.

EXAMPLE 18B

A mixture of the compound (0.9 g) obtained in Example 16B and ethanolic hydrochloride (5%, 6 ml) was heated under refluxing conditions for 1 hour and concentrated under reduced pressure. The residue was made basic with 2N NaOH, after which it was extracted with dichloromethane. The dichloromethane layer was washed with water, dried (MgSO$_4$) and concentrated under reduced pressure. The residue was subjected to silica gel column chromatography and eluted with ethyl acetate-ethanol (5:1, v/v) to yield 2-aminomethyl-7-benzyl-3-chloro-4-(3,4-dimethoxyphenyl)-5,6,7,8-tetrahydrothieno[2,3-b: 5,4-c']dipyridine (0.59 g, 81%) as colorless powder.

EXAMPLE 19B

Benzenesulfonyl chloride (0.156 g) was added to a mixture of the compound (0.35 g) obtained in Example 18B, triethylamine (0.096 g) and dichloromethane (8 ml) under ice-cooling, the mixture was stirred for 1 hour, the reaction mixture was washed successively with water, an aqueous saturated solution of sodium bicarbonate and water, dried (MgSO$_4$) and concentrated under reduced pressure. The residue was subjected to silica gel column chromatography and eluted with ethyl acetate-hexane (1:1, v/v) to yield 7-benzyl-3-chloro-4-(3,4-dimethoxyphenyl)-2-phenylsulfonylaminomethyl-5,6,7,8-tetrahydrothieno[2,3-b:5,4-c']dipyridine (0.25 g, 55%), which was then recrystallized from ethyl acetate-hexane to yield colorless prismatic crystals having a melting point of 153 to 154° C.

EXAMPLE 20B

N-hydroxybenotriazole (HOBt) (0.427 g) and 1-ethyl-3-(3-dimethylaminopropyl)carbodiimide (WSC) (0.535 g) were added to an ice-cooled mixture of the compound (1.0 g) obtained in Example 18B, (1,2,4-triazol-1-yl)acetic acid (0.325 g) and N,N-dimethylformamide (DMF) (20 ml), the mixture was stirred at room temperature for 8 hours, poured over water and extracted with ethyl acetate. The ethyl acetate layer was washed with water, dried (MgSO$_4$) and concentrated under reduced pressure. The residue was subjected to silica gel column chromatography and eluted with ethyl acetate-methanol (20:1, v/v) to yield 7-benzyl-3-chloro-4-(3,4-dimethoxyphenyl)-5,6,7,8-tetrahydro-2-(1,2,4-triazol-1-ylacetylaminomethyl)thieno[2,3-b:5,4-c']dipyridine (0.55 g, 50%), which was then recrystallized from ethyl acetate-hexane to yield a colorless powder having a melting point of 101 to 102° C.

EXAMPLE 21B

A mixture of the compound (0.3 g) obtained in Example 18B, acetic anhydride (0.142 g) and pyridine (2.5 ml) was stirred at room temperature for 1 hour and concentrated under reduced pressure. Ethyl acetate was added to the residue, which was washed with water, dried (MgSO$_4$) and concentrated under reduced pressure. The residue was subjected to silica gel column chromatography and eluted with ethyl acetate to yield 2-acetylaminomethyl-7-benzyl-3-chloro-4-(3,4-dimethoxyphenyl)-5,6,7,8-tetrahydrothieno[2,3-b:5,4-c']dipyridine as an oil, which was then treated with ethanolic hydrochloride to yield the hydrochloride which was recrystallized from dichloromethane-ethyl ether to yield light-yellow powder having a melting point of 172 to 174° C.

EXAMPLE 22B

Nicotinoyl chloride hydrochloride (0.18 g) was added to a solution of the compound (0.29 g) obtained in Example 18B in pyridine (4 ml), the mixture was stirred at room temperature for 1 hour, poured over water and extracted with ethyl acetate. The ethyl acetate layer was washed with water, dried (MgSO$_4$) and concentrated under reduced pressure. The residue was subjected to silica gel column chromatography and eluted with ethyl acetate to yield 7-benzyl-3-chloro-4-(3,4-dimethoxyphenyl)-2-(nicotinoylaminomethyl)-5,6,7,8-tetrahydrothieno[2,3-b:5,4-c']dipyridine (0.2 g, 51%), which was then recrystallized from ethyl acetate-hexane to yield colorless prismatic crystals having a melting point of 124 to 125° C.

EXAMPLE 23B

Oily sodium hydride (60%, 0.394 g) was added to a solution of 2-pyrrolidone (0.839 g) in N,N-dimethylformamide (50 ml), and the mixture was stirred at room temperature for 20 minutes. Then, the compound (4.0 g) obtained in Reference Example 11B was added thereto, the mixture was stirred at 60° C. for 20 minutes, the reaction mixture was poured over water and the precipitated solid was filtered. This crystal was subjected to silica gel column chromatography and eluted with ethyl acetate-hexane (4:3, v/v) to yield 7-benzyl-3-chloro-4-(4-isopropoxy-3-methoxyphenyl)-2-(2-oxo-1-pyrrolidinylmethyl)-5,6,7,8-tetrahydrothieno[2,3-b:5,4-c']dipyridine (0.72 g, 17%), which was then recrystallized from ethyl acetate-hexane to yield colorless prismatic crystals having a melting point of 140 to 141° C.

EXAMPLE 24B

In the same manner as in Example 23B, the compound obtained in Reference Example 3B and 2-piperidone were reacted to yield 7-benzyl-3-chloro-4-(3,4-dimethoxyphenyl)-2-(2-oxo-1-piperidinylmethyl)-5,6,7,8-tetrahydrothieno[2,3-b:5,4-c']dipyridine, which was then recrystallized from ethanol-isopropyl ether to yield light-yellow prismatic crystals having a melting point of 113 to 114° C.

EXAMPLE 25B

In the same manner as in Example 23B, the compound obtained in Reference Example 3B and ε-caprolactam were reacted to yield 7-benzyl-3-chloro-4-(3,4-dimethoxyphenyl)-2-(2-oxohexamethyleneiminomethyl)-5,6,7,8-tetrahydrothieno[2,3-b:5,4-c']dipyridine, which was then recrystallized from ethyl acetate-hexane to yield light-yellow prismatic crystals having a melting point of 113 to 114° C.

EXAMPLE 26B

A mixture of the compound (2.5 g) obtained in Reference Example 3B, 1H-1,2,4-triazole (0.414 g), potassium carbonate (0.691 g) and acetone (50 ml) was stirred under refluxing conditions for 10 hours and concentrated under reduced pressure. Ethyl acetate was added to the residue, which was washed with water, dried (MgSO$_4$) and concentrated under reduced pressure. The residue was subjected to silica gel column chromatography and eluted with ethyl acetate to yield 7-benzyl-3-chloro-4-(3,4-dimethoxyphenyl)-5,6,7,8-tetrahydro-2-(1,2,4-triazol-1-ylmethyl)thieno[2,3-b:5,4-c']dipyridine (1.93 g, 73%), which was then recrystallized from ethyl acetate-hexane to yield colorless prismatic crystals having a melting point of 165 to 166° C.

EXAMPLE 27B

From the fraction subsequently eluted in the column chromatography of Example 26B, 7-benzyl-3-chloro-4-(3, 4-dimethoxyphenyl)-5,6,7,8-tetrahydro-2-(1,2,4-triazol-4-ylmethyl)thieno[2,3-b:5,4-c']dipyridine (0.22 g, 8%), which was then recrystallized from ethyl acetate-hexane to yield colorless prismatic crystals having a melting point of 176 to 177° C.

EXAMPLE 28B

Oily sodium hydride (60%, 0.088 g) was added to a solution of 2-pyrrolidone (0.204 g) in N,N-dimethylformamide (15 ml) and the mixture was stirred at room temperature for 15 minutes. Then, the compound (1.0 g) obtained in Reference Example 3B was added thereto, after which it was stirred at 90° C. for 20 minutes and the reaction mixture was poured over water and extracted with ethyl acetate. The ethyl acetate layer was washed with water, dried (MgSO$_4$) and concentrated under reduced pressure. The residue was subjected to silica gel column chromatography and eluted with ethyl acetate to yield 7-benzyl-3-chloro-4-(3,4-dimethoxyphenyl)-2-(2-oxo-1-pyrrolidinylmethyl)-5,6,7,8-tetrahydrothieno[2,3-b:5,4-c'] dipyridine (0.21 g, 19%), which was then recrystallized from ethyl acetate-hexane as colorless prismatic crystals having a melting point of 139 to 140° C.

EXAMPLE 29B

A solution of titanium tetrachloride (6.3 g) in dichloromethane (10 ml) was added dropwise to a solution of the compound (3.8 g) obtained in Example 23B in dichloromethane (75 ml) under ice-cooling, and the mixture was stirred at 0° C. for 1.5 hours. The reaction mixture was poured over ice-aqueous saturated solution of sodium bicarbonate and the insoluble was filtered off, the organic layer was washed with water, dried (MgSO$_4$) and concentrated under reduced pressure. The residue was subjected to silica gel column chromatography and eluted with ethyl acetate-hexane (7:3, v/v) to yield 7-benzyl-3-chloro-4-(4-hydroxy-3-methoxyphenyl)-2-(2-oxo-1-pyrrolidinylmethyl)-5,6,7,8-tetrahydrothieno[2,3-b:5,4-c']dipyridine (0.89 g, 25%), which was then recrystallized as colorless prismatic crystals having a melting point of 190 to 191° C.

EXAMPLE 30B

In the same manner as in Example 28B, the compound obtained in Reference Example 3 and 4-hydroxy-2-oxopyrrolidine were reacted to yield 7-benzyl-3-chloro-4-(3,4-dimethoxyphenyl)-2-(4-hydroxy-2-oxopyrrolidin-1-ylmethyl)-5,6,7,8-tetrahydrothieno[2,3-b:5,4-c']dipyridine as an amorphous solid.

NMR (δ ppm in CDCl$_3$): 1.90–2.15 (2H, m), 2.40–2.68 (3H, m), 2.82 (1H, dd, J=17.6 & 5.4 Hz), 3.50 (1H, dd, J=10.6 & 4.0 Hz), 3.66 (2H, s), 3.71 (2H, s), 3.87 (3H, s), 3.96 (3H, s), 4.45–4.65 (2H, s), 5.15 (1H, d, J=16.6 & 3.6 Hz), 6.68–6.85(2H, m), 6.95(1H, dd, J=7.8 & 2.0 Hz), 7.20–7.48 (5H, m)

EXAMPLE 31B

In the same manner as in Example 28B, the compound obtained in Reference Example 3B and 5-methyl-2-oxopyrrolidine were reacted to yield 7-benzyl-3-chloro-4-(3,4-dimethoxyphenyl)-2-(5-methyl-2-oxopyrrolidin-1-ylmethyl)-5,6,7,8-tetrahydrothieno[2,3-b:5,4-c']dipyridine as amorphous solid.

NMR (δ ppm in CDCl$_3$): 1.22 (3H, d, J=6.2 Hz), 1.94–2.08 (2H, m), 2.20–2.63 (6H, m), 3.65 (2H, s), 3.70 (2H, s), 3.78–4.05 (7H, m), 4.42 (1H, d, J=16.8 Hz), 5.24 (1H, d, J=16.8 Hz), 6.73 (1H, d, J=1.8 Hz), 6.77 (1H, dd, J=8.0 & 1.8 Hz), 6.94 (1H, d, J=8.0 Hz), 7.20–7.42 (5H, m)

EXAMPLE 32B

In the same manner as in Example 28B, the compound obtained in Reference Example 3B and 3-oxo-1-phenylpyrazoline were reacted to yield 7-benzyl-3-chloro-4-(3,4-dimethoxyphenyl)-2-(1-phenyl-2-pyrazolin-3-yloxymethyl)-5,6,7,8-tetrahydrothieno[2,3-b:5,4-c'] dipyridine, which was then recrystallized from ethyl acetate-hexane to yield colorless prismatic crystals having a melting point of 157 to 158° C.

EXAMPLE 33B

From the fraction subsequently eluted in the column chromatography of Example 32B, 7-benzyl-3-chloro-4-(3,4-dimethoxyphenyl)-2-(3-oxo-phenylpyrazolidin-2-ylmethyl)-5,6,7,8-tetrahydrothieno[2,3-b:5,4-c'] dipyridine as amorphous solid.

NMR (δ ppm in CDCl$_3$): 1.90–2.10 (2H, m), 2.57 (2H, t, J=5.8 Hz), 2.71 (2H, t, J=7.6 Hz), 3.66 (2H, s), 3.71 (2H, s), 3.85 (3H, s), 3.94 (3H, s), 4.17 (2H, t, J=7.6 Hz), 4.98 (2H, s), 6.68 (1H, d, J=1.8 Hz), 6.75 (1H, dd, J=8.3 & 1.8 Hz), 6.93 (1H, d, J=8.2 Hz), 6.98–7.15 (3H, m), 7.25–7.50 (5H, m)

EXAMPLE 34B

In the same manner as in Example 28B, the compound obtained in Reference Example 3B and 3-methyl-5-oxo-2-pyrazoline were reacted to yield 7-benzyl-3-chloro-4-(3,4-dimethoxyphenyl)-2-(3-methyl-5-oxo-2-pyrazolin-1-ylmethyl)-5,6,7,8-tetrahydrothieno[2,3-b:5,4-c']dipyridine as amorphous solid.

NMR (δ ppm in CDCl$_3$): 1.82–2.08 (2H, m), 2.25 (3H, s), 2.50–2.63 (2H, m), 3.66 (2H, s), 3.71 (2H, s), 3.87 (3H, s), 3.95 (3H, s), 5.30–5.62 (3H, m), 6.70–6.85 (2H, m), 6.94 (1H, d, J=7.88 Hz), 7.20–7.43 (5H, m)

EXAMPLE 35B

A mixture of the compound obtained in Reference Example 3B (1.0 g), succinimide (0.238 g), potassium carbonate (0.276 g) and N,N-dimethylformamide (10 ml) was stirred at 100° C. for 1 hour, poured into water and extracted with ethyl acetate. The ethyl acetate extract was washed with water, dried (MgSO$_4$) and concentrated in vacuo. The residue was chromatographed on SiO$_2$ with ethyl acetate-hexane (1:1, v/v) to give 7-benzyl-3-chloro-2-(2,5-dioxopyrrolidin-1-ylmethyl)-4-(3,4-dimethoxyphenyl)-5,6,7,8-tetrahydrothieno[2,3-b:5,4-c']dipyridien (0.65 g, 58%) as crystals. Recrystallization from ethanol-hexane gave pale yellow prisms, m.p. 128–130° C.

EXAMPLE 36B

A mixture of the compound obtained in Example 28B (3.0 g), palladium on carbon (5%, 5.0 g), nitrobenzene (1.3 g) and xylene (100 ml) was stirred under reflux for 4 hours and the insoluble solid was filtered off. The filtrate was concentrated in vacuo and the residue was chromatographed on SiO$_2$ with ethyl acetate to give 3-chloro-4-(3,4-dimethoxyphenyl)-2-(2-oxopyrrolidin-1-ylmethyl)thieno[2,3-b:5,4-c']dipyridine (0.25 g, 10%) as crystals. Recrystallization from ethyl acetate-hexane give colorless prisms, m.p. 228–230° C.

As described hereinabove, the present invention provides the novel thienopyridine derivative having excellent anti-inflammatory activity and the thienopyridine derivative is useful for an anti-inflammatory drug, especially as a drug for treating arthritis, particularly chronic rheumatoid arthritis. The novel thienopyridine derivative also exhibit excellent bone resorption inhibitory activity and is useful as a drug for preventing or treating bone destruction and osteoporosis. In addition, the novel thienopyridine derivative is useful for a drug for preventing or treating immune-related diseases.

What is claimed is:

1. A compound represented by the formula (I'):

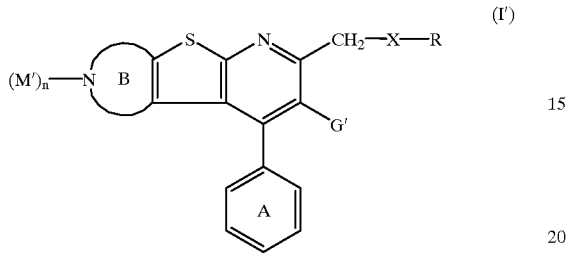

wherein G' represents a halogen atom;
M' represents
  a hydrogen atom,
  a hydrocarbon group which is unsubstituted or substituted by halogen, amino, acyl, hydroxy, alkoxy, alkenyloxy, alkynyloxy, aralkyloxy, acyloxy, aryloxy, a hydrocarbon group, thio, alkylthio, alkenylthio, alkynylthio, aralkylthio, acylthio, arylthio, carboxyl, alkyloxycarbonyl, alkenyloxycarbonyl, alkynyloxycarbonyl, aralkyloxycarbonyl, acyloxycarbonyl, or aryloxycarbonyl,
  an acyl group which is unsubstituted or substituted by halogen, amino, acyl, hydroxy, alkoxy, alkenyloxy, alkynyloxy, aralkyloxy, acyloxy, aryloxy, a hydrocarbon group, thio, alkylthio, alkenylthio, alkynylthio, aralkylthio, acylthio, arylthio, carboxyl, alkyloxycarbonyl, alkenyloxycarbonyl, alkynyloxycarbonyl, aralkyloxycarbonyl, acyloxycarbonyl, or aryloxycarbonyl,
  a carbamoyl group, which is unsubstituted or substituted by a hydrocarbon group, halogen, amino, acyl, hydroxy, alkoxy, alkenyloxy, alkynyloxy, aralkyloxy, acyloxy, aryloxy, thio, alkylthio, alkenylthio, alkynylthio, aralkylthio, acylthio, arylthio, carboxyl, alkyloxycarbonyl, alkenyloxycarbonyl, alkynyloxycarbonyl, aralkyloxycarbonyl, acyloxycarbonyl, or aryloxycarbonyl,
  a thiocarbamoyl group which is unsubstituted or substituted by a hydrocarbon group, halogen, amino, acyl, hydroxy, alkoxy, alkenyloxy, alkynyloxy, aralkyloxy, acyloxy, aryloxy, thio, alkylthio, alkenylthio, alkynylthio, aralkylthio, acylthio, arylthio, carboxyl, alkyloxycarbonyl, alkenyloxycarbonyl, alkynyloxycarbonyl, aralkyloxycarbonyl, acyloxycarbonyl, or aryloxycarbonyl, or
  a sulfonyl group which is unsubstituted or substituted by a hydrocarbon group, halogen, amino, acyl, hydroxy, alkoxy, alkenyloxy, alkynyloxy, aralkyloxy, acyloxy, aryloxy, thio, alkylthio, alkenylthio, alkynylthio, aralkylthio, acylthio, arylthio, carboxyl, alkyloxycarbonyl, alkenyloxycarbonyl, alkynyloxycarbonyl, aralkyloxycarbonyl, acyloxycarbonyl, or aryloxycarbonyl;

n is 0 or 1;
R represents
  a 5- to 7-membered heterocyclic ring containing one sulfur atom, nitrogen atom, or oxygen atom which is unsubstituted or substituted by a hydrocarbon group, halogen, amino, acyl, hydroxy, alkoxy, alkenyloxy, alkynyloxy, aralkyloxy, acyloxy, aryloxy, thio, alkylthio, alkenylthio, alkynylthio, aralkylthio, acylthio, arylthio, carboxyl, oxo, alkyloxycarbonyl, alkenyloxycarbonyl, alkynyloxycarbonyl, aralkyloxycarbonyl, acyloxycarbonyl, or aryloxycarbonyl, or
  an amino group represented by —N(R$^1$)(R$^2$) in which R$^1$ and R$^2$ are the same or different and are a hydrogen atom; a hydrocarbon group which is unsubstituted or substituted by halogen, amino, acyl, hydroxy, alkoxy, alkenyloxy, alkynyloxy, aralkyloxy, acyloxy, aryloxy, a hydrocarbon group, thio, alkylthio, alkenylthio, alkynylthio, aralkylthio, acylthio, arylthio, carboxyl, alkyloxycarbonyl, alkenyloxycarbonyl, alkynyloxycarbonyl, aralkyloxycarbonyl, acyloxycarbonyl, or aryloxycarbonyl; an acyl group; a sulfonyl group; or a 5- to 7-membered heterocyclic ring containing one sulfur atom, nitrogen atom, or oxygen atom which is unsubstituted or substituted by a hydrocarbon group, halogen, amino, acyl, hydroxy, alkoxy, alkenyloxy, alkynyloxy, aralkyloxy, acyloxy, aryloxy, thio, alkylthio, alkenylthio, alkynylthio, aralkylthio, acylthio, arylthio, carboxyl, alkyloxycarbonyl, alkenyloxycarbonyl, alkynyloxycarbonyl, aralkyloxycarbonyl, acyloxycarbonyl, or aryloxycarbonyl; or R$^1$ and R$^2$ may bind to each other to form a 5- to 7-membered heterocyclic ring containing one nitrogen atom, which is unsubstituted or substituted by a hydrocarbon group, halogen, amino, acyl, hydroxy, alkoxy, alkenyloxy, alkynyloxy, aralkyloxy, acyloxy, aryloxy, thio, alkylthio, alkenylthio, alkynylthio, aralkylthio, acylthio, arylthio, carboxyl, oxo, alkyloxycarbonyl, alkenyloxycarbonyl, alkynyloxycarbonyl, aralkyloxycarbonyl, acyloxycarbonyl, or aryloxycarbonyl;
X is (—CH$_2$—)$_q$ and q is an integer from 0 to 5;
the ring A is unsubstituted or substituted by
  a halogen atom,
  a nitro group,
  an alkyl group,
  a hydroxy group which is unprotected or protected by a protecting group,
  a thiol group which is unprotected or protected by a protecting group,
  an amino group which is unsubstituted or substituted by alkyl, alkenyl, alkynyl, aryl, or acyl,
  an acyl group,
  a carboxyl group,
  an alkyloxycarbonyl group,
  an alkenyloxycarbonyl group,
  an alkynyloxycarbonyl group,
  an aralkyloxycarbonyl group,
  an acyloxycarbonyl group,
  an aryloxycarbonyl group,
  an aromatic hydrocarbon group, or
  a heteroaryl selected from the group consisting of pyridyl, furyl, thienyl, imidazolyl, and thiazolyl;
the ring B represents a 6-membered ring containing a nitrogen atom; or a pharmaceutically acceptable salt thereof.

2. The compound of claim 1, wherein the substituent for the ring A is a $C_{1-6}$ alkoxy group or a hydroxy group.

3. The compound of claim 2, wherein the ring A has one methoxy group.

4. The compound of claim 1, wherein q is 0.

5. The compound of claim 1, wherein G' is a chlorine atom.

6. The compound of claim 1, wherein R is substituted by oxo.

7. A process for making the compound of claim 1, comprising (a) reacting a compound of the formula (II'-1):

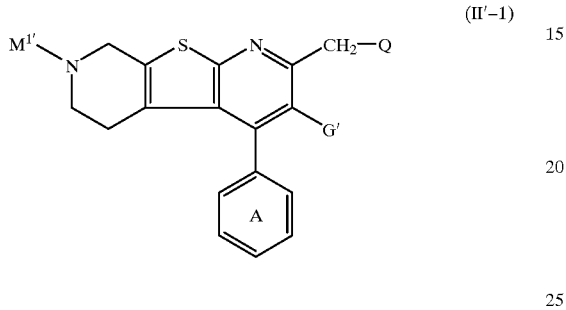

(II'-1)

wherein $M^{1'}$ is
  a hydrocarbon group which is unsubstituted or substituted by halogen, amino, acyl, hydroxy, alkoxy, alkenyloxy, alkynyloxy, aralkyloxy, acyloxy, aryloxy, a hydrocarbon group, thio, alkylthio, alkenylthio, alkynylthio, aralkylthio, acylthio, arylthio, carboxyl, alkyloxycarbonyl, alkenyloxycarbonyl, alkynyloxycarbonyl, aralkyloxycarbonyl, acyloxycarbonyl, or aryloxycarbonyl,
  an acyl group which is unsubstituted or substituted by halogen, amino, acyl, hydroxy, alkoxy, alkenyloxy, alkynyloxy, aralkyloxy, acyloxy, aryloxy, a hydrocarbon group, thio, alkylthio, alkenylthio, alkynylthio, aralkylthio, acylthio, arylthio, carboxyl, alkyloxycarbonyl, alkenyloxycarbonyl, alkynyloxycarbonyl, aralkyloxycarbonyl, acyloxycarbonyl, or aryloxycarbonyl,
  a carbamoyl group, which is unsubstituted or substituted by a hydrocarbon group, halogen, amino, acyl, hydroxy, alkoxy, alkenyloxy, alkynyloxy, aralkyloxy, acyloxy, aryloxy, thio, alkylthio, alkenylthio, alkynylthio, aralkylthio, acylthio, arylthio, carboxyl, alkyloxycarbonyl, alkenyloxycarbonyl, alkynyloxycarbonyl, aralkyloxycarbonyl, acyloxycarbonyl, or aryloxycarbonyl,
  a thiocarbamoyl group which is unsubstituted or substituted by a hydrocarbon group, halogen, amino, acyl, hydroxy, alkoxy, alkenyloxy, alkynyloxy, aralkyloxy, acyloxy, aryloxy, thio, alkylthio, alkenylthio, alkynylthio, aralkylthio, acylthio, arylthio, carboxyl, alkyloxycarbonyl, alkenyloxycarbonyl, alkynyloxycarbonyl, aralkyloxycarbonyl, acyloxycarbonyl, or aryloxycarbonyl;

Q is a leaving group;
$X^1$ is an oxygen atom or a sulfur atom;
G' and the ring A are as defined in claim 1,
with a compound of the formula (III'):

R—$X^1$H        (III')

wherein R is as defined in claim 1, in the presence of a base;

or (b) reacting a compound of the formula (II'-2):

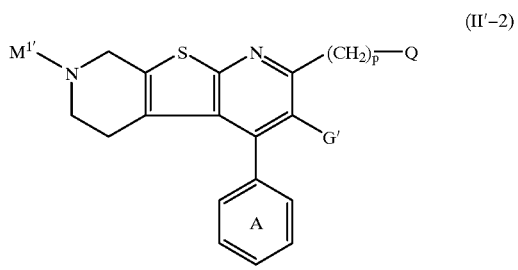

(II'-2)

wherein p is 1 to 6; and the other symbols are as defined in claim 1, with a compound of the formula (IV'):

(IV')

wherein $R^1$ and $R^2$ are as defined in claim 1, in the presence of a base; or (c) hydrolyzing a compound of the formula (I'-3):

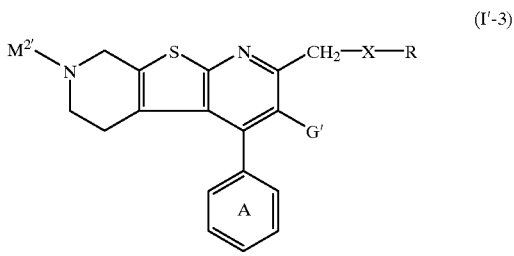

(I'-3)

wherein $M^{2'}$ is an acyl group which is unsubstituted or substituted by halogen, amino, acyl, hydroxy, alkoxy, alkenyloxy, alkynyloxy, aralkyloxy, acyloxy, aryloxy, a hydrocarbon group, thio, alkylthio, alkenylthio, alkynylthio, aralkylthio, acylthio, arylthio, carboxyl, alkyloxycarbonyl, alkenyloxycarbonyl, alkynyloxycarbonyl, aralkyloxycarbonyl, acyloxycarbonyl, or aryloxycarbonyl; and the other symbols are as defined in claim 1, in the presence of an acid; or (d) oxidizing a compound of the formula (I'-4):

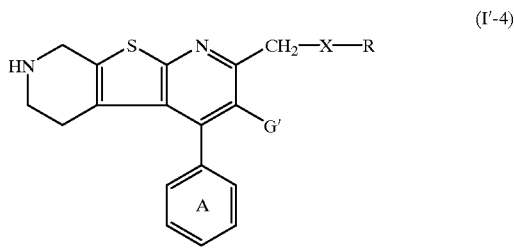

(I'-4)

wherein the symbols are as defined in claim 1; or (e) reacting a compound of the formula (I'-4) with a compound of the formula (V'):

$R^5SO_2Cl$  (V')

wherein $R^5$ is
a hydrocarbon group which is unsubstituted or substituted by halogen, amino, acyl, hydroxy, alkoxy, alkenyloxy, alkynyloxy, aralkyloxy, acyloxy, aryloxy, a hydrocarbon group, thio, alkylthio, alkenylthio, alkynylthio, aralkylthio, acylthio, arylthio, carboxyl, alkyloxycarbonyl, alkenyloxycarbonyl, alkynyloxycarbonyl, aralkyloxycarbonyl, acyloxycarbonyl, or aryloxycarbonyl, or a 5- to 7-membered heterocyclic ring containing one sulfur atom, nitrogen atom, or oxygen atom which is unsubstituted or substituted by a hydrocarbon group, halogen, amino, acyl, hydroxy, alkoxy, alkenyloxy, alkynyloxy, aralkyloxy, acyloxy, aryloxy, thio, alkylthio, alkenylthio, alkynylthio, aralkylthio, acylthio, arylthio, carboxyl, oxo, alkyloxycarbonyl, alkenyloxycarbonyl, alkynyloxycarbonyl, aralkyloxycarbonyl, acyloxycarbonyl, or aryloxycarbonyl, in the presence of a base; or (f) reacting a compound of the formula (I'-4) with a compound of the formula (VI'):

$R^5NCX^1$  (VI')

wherein the symbols are as defined above; or (g) reacting a compound of the formula (I'-4) with a compound of the formula (VII'):

$R^{5'}$—Q  (VII')

wherein $R^5$ is a hydrocarbon group which is unsubstituted or substituted by halogen, amino, acyl, hydroxy, alkoxy, alkenyloxy, alkynyloxy, aralkyloxy, acyloxy, aryloxy, a hydrocarbon group, thio, alkylthio, alkenylthio, alkynylthio, aralkylthio, acylthio, arylthio, carboxyl, alkyloxycarbonyl, alkenyloxycarbonyl, alkynyloxycarbonyl, aralkyloxycarbonyl, acyloxycarbonyl, or aryloxycarbonyl, and Q is as defined above; or (h) reacting a compound of the formula (I'-4) with a compound of the formula (VIII'):

$R^5$—COOH  (VIII')

wherein $R^5$ is as defined above; or (i) reacting a compound of the formulas (IX') and (X'):

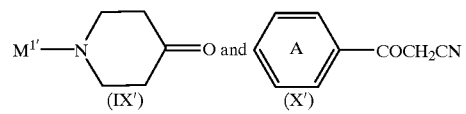

wherein the symbols are as defined above, and sulfur to obtain a compound of the formula (XI'):

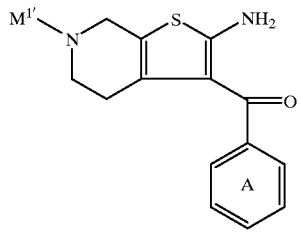

(XI')

wherein the symbols are as defined above, and then reacting the resultant compound of the formula (XI') with a compound of the formula (XII'):

$QCH_2COCH_2$—G'  (XII')

wherein the symbols are as defined above.

8. A pharmaceutical composition comprising a pharmaceutically effective amount of a compound of claim 1 or a pharmaceutically acceptable salt thereof and a pharmaceutically acceptable carrier or excipient.

9. A method for treating inflammatory disease in a mammal which comprises administering an effective amount of the pharmaceutical composition of claim 8 to said mammal in need thereof.

10. A method for treating arthritis in a mammal which comprises administering an effective amount of the pharmaceutical composition of claim 8 to said mammal in need thereof.

11. A method for treating rheumatism in a mammal which comprises administering an effective amount of the pharmaceutical composition of claim 8 to said mammal in need thereof.

12. A method for treating rheumatoid arthritis in a mammal which comprises administering an effective amount of the pharmaceutical composition of claim 8 to said mammal in need thereof.

13. A method for inhibiting bone resorption in a mammal which comprises administering an effective amount of the pharmaceutical composition of claim 8 to said mammal in need thereof.

14. A method for treating osteoporosis in a mammal which comprises administering an effective amount of the pharmaceutical composition of claim 8 to said mammal in need thereof.

15. A method for inhibiting the production of cytokines in a mammal which comprises administering an effective amount of the pharmaceutical composition of claim 8 to said mammal in need thereof.

16. A method for treating autoimmune disease in a mammal which comprises administering an effective amount of the pharmaceutical composition of claim 8 to said mammal in need thereof.

17. A method for treating rejection after organ transplantation in a mammal which comprises administering an effective amount of the pharmaceutical composition of claim 8 to said mammal in need thereof.

* * * * *